(12) United States Patent
Reinders et al.

(10) Patent No.: US 9,572,509 B2
(45) Date of Patent: *Feb. 21, 2017

(54) SYSTEMS AND METHODS FOR ACTIVATING TRANSDUCERS

(71) Applicant: Kardium Inc., Burnaby (CA)

(72) Inventors: Daniel Martin Reinders, Richmond (CA); Daniel Robert Weinkam, Coquitlam (CA); Roxanne Wai Tak Louie, Vancouver (CA); Danai Bisalputra, New Westminster (CA)

(73) Assignee: KARDIUM INC., Burnaby (CA)

(*) Notice: Subject to any disclaimer, the term of this patent is extended or adjusted under 35 U.S.C. 154(b) by 0 days.

This patent is subject to a terminal disclaimer.

(21) Appl. No.: 14/948,924

(22) Filed: Nov. 23, 2015

(65) Prior Publication Data

US 2016/0073918 A1     Mar. 17, 2016

Related U.S. Application Data

(63) Continuation of application No. 14/546,683, filed on Nov. 18, 2014, now Pat. No. 9,198,592, which is a
(Continued)

(51) Int. Cl.
*A61B 18/00* (2006.01)
*A61B 18/12* (2006.01)
(Continued)

(52) U.S. Cl.
CPC ............ *A61B 5/0422* (2013.01); *A61B 5/042* (2013.01); *A61B 5/053* (2013.01); *A61B 5/0538* (2013.01);
(Continued)

(58) Field of Classification Search
None
See application file for complete search history.

(56) References Cited

U.S. PATENT DOCUMENTS

| 4,114,202 A | 9/1978 | Roy et al. |
| 4,164,046 A | 8/1979 | Cooley |

(Continued)

FOREIGN PATENT DOCUMENTS

| EP | 0723467 B1 | 4/2002 |
| EP | 1645234 A1 | 4/2006 |

(Continued)

OTHER PUBLICATIONS

International Search Report and Written Opinion issued in PCT/CA2013/050350 mailed Aug. 2, 2013.
(Continued)

*Primary Examiner* — Brian T Gedeon
(74) *Attorney, Agent, or Firm* — Rossi, Kimms & McDowell LLP

(57) ABSTRACT

Transducer-based systems and methods may be configured to display a graphical representation of a transducer-based device, the graphical representation including graphical elements corresponding to transducers of the transducer-based device, and also including between graphical elements respectively associated with a set of the transducers and respectively associated with a region of space between the transducers of the transducer-based device. Selection of graphical elements and/or between graphical elements can cause activation of the set of transducers associated with the selected elements. Transducer activation characteristics, such as initiation time, activation duration, activation sequence, and energy delivery characteristics, can vary based on numerous factors. Visual characteristics of graphical elements and between graphical elements can change based on an activation-status of the corresponding transducers. Activation requests for a set of transducers can be denied if it is determined that a transducer in the set of transducers is unacceptable for activation.

22 Claims, 30 Drawing Sheets

Related U.S. Application Data continuation-in-part of application No. 13/792,781, filed on Mar. 11, 2013, now Pat. No. 9,017,320.

(60) Provisional application No. 61/723,311, filed on Nov. 6, 2012, provisional application No. 61/670,881, filed on Jul. 12, 2012, provisional application No. 61/649,734, filed on May 21, 2012.

(51) Int. Cl.

| | | |
|---|---|---|
| *A61B 5/042* | (2006.01) | |
| *A61N 1/362* | (2006.01) | |
| *A61N 1/372* | (2006.01) | |
| *A61B 5/00* | (2006.01) | |
| *A61B 5/053* | (2006.01) | |
| *A61B 5/01* | (2006.01) | |
| *A61B 18/14* | (2006.01) | |
| *A61B 17/00* | (2006.01) | |

(52) U.S. Cl.
CPC ......... *A61B 5/6858* (2013.01); *A61B 5/6869* (2013.01); *A61B 5/743* (2013.01); *A61B 5/7435* (2013.01); *A61B 18/1233* (2013.01); *A61N 1/362* (2013.01); *A61N 1/37247* (2013.01); *A61B 5/01* (2013.01); *A61B 18/1206* (2013.01); *A61B 18/1492* (2013.01); *A61B 34/20* (2016.02); *A61B 2017/003* (2013.01); *A61B 2018/00267* (2013.01); *A61B 2018/00351* (2013.01); *A61B 2018/00357* (2013.01); *A61B 2018/00577* (2013.01); *A61B 2018/00797* (2013.01); *A61B 2018/00839* (2013.01); *A61B 2018/00875* (2013.01); *A61B 2018/00892* (2013.01); *A61B 2018/00982* (2013.01); *A61B 2018/124* (2013.01); *A61B 2034/107* (2016.02); *A61B 2090/065* (2016.02); *A61B 2562/046* (2013.01); *A61B 2562/222* (2013.01)

(56) References Cited

U.S. PATENT DOCUMENTS

| | | |
|---|---|---|
| 4,225,148 A | 9/1980 | Andersson |
| 4,240,441 A | 12/1980 | Khalil |
| 4,263,680 A | 4/1981 | Reul et al. |
| 4,273,128 A | 6/1981 | Lary |
| 4,411,266 A | 10/1983 | Cosman |
| 4,490,859 A | 1/1985 | Black et al. |
| 4,543,090 A | 9/1985 | McCoy |
| 4,699,147 A | 10/1987 | Chilson et al. |
| 4,770,187 A | 9/1988 | Lash et al. |
| 4,794,912 A | 1/1989 | Lia |
| 4,850,957 A | 7/1989 | Summers |
| 4,887,613 A | 12/1989 | Farr et al. |
| 4,890,602 A | 1/1990 | Hake |
| 4,890,612 A | 1/1990 | Kensey |
| 4,893,613 A | 1/1990 | Hake |
| 4,895,166 A | 1/1990 | Farr et al. |
| 4,921,499 A | 5/1990 | Hoffman et al. |
| 4,940,064 A | 7/1990 | Desai |
| 4,942,788 A | 7/1990 | Farr et al. |
| 4,979,514 A | 12/1990 | Sekii et al. |
| 4,998,933 A | 3/1991 | Eggers et al. |
| 5,026,384 A | 6/1991 | Farr et al. |
| 5,047,047 A | 9/1991 | Yoon |
| 5,122,137 A | 6/1992 | Lennox |
| 5,127,902 A | 7/1992 | Fischell |
| 5,156,151 A | 10/1992 | Imran |
| 5,174,299 A | 12/1992 | Nelson |
| 5,176,693 A | 1/1993 | Pannek, Jr. |
| 5,178,620 A | 1/1993 | Eggers et al. |
| 5,192,291 A | 3/1993 | Pannek, Jr. |
| 5,201,316 A | 4/1993 | Pomeranz et al. |
| 5,228,442 A | 7/1993 | Imran |
| 5,242,386 A | 9/1993 | Holzer |
| 5,255,679 A | 10/1993 | Imran |
| 5,279,299 A | 1/1994 | Imran |
| 5,293,869 A | 3/1994 | Edwards et al. |
| 5,312,435 A | 5/1994 | Nash et al. |
| 5,317,952 A | 6/1994 | Immega |
| 5,327,889 A | 7/1994 | Imran |
| 5,341,807 A | 8/1994 | Nardella |
| 5,366,443 A | 11/1994 | Eggers et al. |
| 5,379,773 A | 1/1995 | Hornsby |
| 5,419,767 A | 5/1995 | Eggers et al. |
| 5,450,860 A | 9/1995 | O'Connor |
| 5,478,353 A | 12/1995 | Yoon |
| 5,496,267 A | 3/1996 | Drasler et al. |
| 5,531,760 A | 7/1996 | Alwafaie |
| 5,545,193 A | 8/1996 | Fleischman et al. |
| 5,557,967 A | 9/1996 | Renger |
| 5,593,424 A | 1/1997 | Northrup, III |
| 5,598,848 A | 2/1997 | Swanson et al. |
| 5,599,345 A | 2/1997 | Edwards et al. |
| 5,620,481 A | 4/1997 | Desai et al. |
| 5,662,587 A | 9/1997 | Grundfest et al. |
| 5,681,308 A | 10/1997 | Edward et al. |
| 5,681,336 A | 10/1997 | Clement et al. |
| 5,687,723 A | 11/1997 | Avitall |
| 5,687,737 A | 11/1997 | Branham et al. |
| 5,697,285 A | 12/1997 | Nappi et al. |
| 5,713,896 A | 2/1998 | Nardella |
| 5,713,942 A | 2/1998 | Sten et al. |
| 5,716,397 A | 2/1998 | Myers |
| 5,720,726 A | 2/1998 | Marcadis et al. |
| 5,728,114 A | 3/1998 | Evans et al. |
| 5,730,127 A | 3/1998 | Avitall |
| 5,762,066 A | 6/1998 | Law et al. |
| 5,769,846 A | 6/1998 | Edwards et al. |
| 5,782,239 A | 7/1998 | Webster, Jr. |
| 5,782,879 A | 7/1998 | Rosborough et al. |
| 5,800,495 A | 9/1998 | Machek et al. |
| 5,810,802 A | 9/1998 | Panescu et al. |
| 5,824,066 A | 10/1998 | Gross |
| 5,836,990 A | 11/1998 | Li |
| 5,876,343 A | 3/1999 | Teo |
| 5,881,727 A | 3/1999 | Edwards |
| 5,891,136 A | 4/1999 | McGee et al. |
| 5,904,711 A | 5/1999 | Flom et al. |
| 5,916,163 A | 6/1999 | Panescu et al. |
| 5,919,207 A | 7/1999 | Taheri |
| 5,921,924 A | 7/1999 | Avitall |
| 5,935,075 A | 8/1999 | Casscells et al. |
| 5,935,079 A | 8/1999 | Swanson et al. |
| 5,941,251 A | 8/1999 | Panescu et al. |
| 5,961,440 A | 10/1999 | Schweich, Jr. et al. |
| 5,968,040 A | 10/1999 | Swanson et al. |
| 5,984,950 A | 11/1999 | Cragg et al. |
| 6,001,069 A | 12/1999 | Tachibana et al. |
| 6,014,581 A | 1/2000 | Whayne et al. |
| 6,104,944 A | 8/2000 | Martinelli |
| 6,138,043 A | 10/2000 | Avitall |
| 6,142,993 A | 11/2000 | Whayne et al. |
| 6,156,046 A | 12/2000 | Passafaro et al. |
| 6,210,432 B1 | 4/2001 | Solem et al. |
| 6,216,043 B1 | 4/2001 | Swanson et al. |
| 6,217,573 B1 | 4/2001 | Webster |
| 6,241,747 B1 | 6/2001 | Ruff |
| 6,248,124 B1 | 6/2001 | Pedros et al. |
| 6,258,258 B1 | 7/2001 | Sartori |
| 6,266,550 B1 | 7/2001 | Selmon et al. |
| 6,304,769 B1 | 10/2001 | Arenson et al. |
| 6,306,135 B1 | 10/2001 | Ellmam et al. |
| 6,308,091 B1 | 10/2001 | Avitall |
| 6,319,249 B1 | 11/2001 | Töllner |
| 6,346,105 B1 | 2/2002 | Tu et al. |
| 6,350,263 B1 | 2/2002 | Wetzig et al. |
| 6,358,258 B1 | 3/2002 | Arcia et al. |
| 6,383,151 B1 | 5/2002 | Diederich et al. |
| 6,389,311 B1 | 5/2002 | Whayne et al. |
| 6,391,024 B1 | 5/2002 | Sun et al. |

(56) References Cited

U.S. PATENT DOCUMENTS

| | | |
|---|---|---|
| 6,391,048 B1 | 5/2002 | Ginn et al. |
| 6,391,054 B2 | 5/2002 | Carpentier et al. |
| 6,402,781 B1 | 6/2002 | Langberg et al. |
| 6,436,052 B1 | 8/2002 | Nikolic et al. |
| 6,475,223 B1 | 11/2002 | Werp et al. |
| 6,485,409 B1 | 11/2002 | Voloshin et al. |
| 6,485,489 B2 | 11/2002 | Teirstein et al. |
| 6,506,210 B1 | 1/2003 | Kanner |
| 6,514,249 B1 | 2/2003 | Maguire et al. |
| 6,529,756 B1 | 3/2003 | Phan et al. |
| 6,537,198 B1 | 3/2003 | Vidlund et al. |
| 6,537,314 B2 | 3/2003 | Langberg et al. |
| 6,540,670 B1 | 4/2003 | Hirata et al. |
| 6,551,312 B2 | 4/2003 | Zhang et al. |
| 6,569,160 B1 | 5/2003 | Goldin et al. |
| 6,569,198 B1 | 5/2003 | Wilson et al. |
| 6,575,971 B2 | 6/2003 | Hauck et al. |
| 6,589,208 B2 | 7/2003 | Ewers et al. |
| 6,626,930 B1 | 9/2003 | Allen et al. |
| 6,632,238 B2 | 10/2003 | Ginn et al. |
| 6,635,056 B2 | 10/2003 | Kadhiresan et al. |
| 6,640,119 B1 | 10/2003 | Budd et al. |
| 6,662,034 B2 | 12/2003 | Segner et al. |
| 6,704,590 B2 | 3/2004 | Haldeman |
| 6,723,038 B1 | 4/2004 | Schroeder et al. |
| 6,726,716 B2 | 4/2004 | Marquez |
| 6,760,616 B2 | 7/2004 | Hoey et al. |
| 6,780,197 B2 | 8/2004 | Roe et al. |
| 6,788,969 B2 | 9/2004 | Dupree et al. |
| 6,797,001 B2 | 9/2004 | Mathis et al. |
| 6,800,090 B2 | 10/2004 | Alferness et al. |
| 6,837,886 B2 | 1/2005 | Collins et al. |
| 6,852,076 B2 | 2/2005 | Nikolic et al. |
| 6,855,143 B2 | 2/2005 | Davison et al. |
| 6,890,353 B2 | 5/2005 | Cohn et al. |
| 6,892,091 B1 | 5/2005 | Ben-Haim et al. |
| 6,899,674 B2 | 5/2005 | Viebach et al. |
| 6,907,297 B2 | 6/2005 | Wellman et al. |
| 6,908,478 B2 | 6/2005 | Alferness et al. |
| 6,913,576 B2 | 7/2005 | Bowman |
| 6,918,903 B2 | 7/2005 | Bass |
| 6,926,669 B1 | 8/2005 | Stewart et al. |
| 6,942,657 B2 | 9/2005 | Sinofsky et al. |
| 6,949,122 B2 | 9/2005 | Adams et al. |
| 6,960,229 B2 | 11/2005 | Mathis et al. |
| 6,986,775 B2 | 1/2006 | Morales et al. |
| 6,989,010 B2 | 1/2006 | Francischelli et al. |
| 6,989,028 B2 | 1/2006 | Lashinski et al. |
| 6,994,093 B2 | 2/2006 | Murphy et al. |
| 6,997,951 B2 | 2/2006 | Solem et al. |
| 7,001,383 B2 | 2/2006 | Keidar |
| 7,025,776 B1 | 4/2006 | Houser et al. |
| 7,048,734 B1 | 5/2006 | Fleischman et al. |
| 7,050,848 B2 | 5/2006 | Hoey et al. |
| 7,052,487 B2 | 5/2006 | Cohn et al. |
| 7,068,867 B2 | 6/2006 | Adoram et al. |
| 7,141,019 B2 | 11/2006 | Pearlman |
| 7,144,363 B2 | 12/2006 | Pai et al. |
| 7,177,677 B2 | 2/2007 | Kaula et al. |
| 7,186,210 B2 | 3/2007 | Feld et al. |
| 7,187,964 B2 | 3/2007 | Khoury |
| 7,189,202 B2 | 3/2007 | Lau et al. |
| 7,279,007 B2 | 10/2007 | Nikolic et al. |
| 7,300,435 B2 | 11/2007 | Wham et al. |
| 7,303,526 B2 | 12/2007 | Sharkey et al. |
| 7,335,196 B2 | 2/2008 | Swanson et al. |
| 7,507,252 B2 | 3/2009 | Lashinski et al. |
| 7,530,980 B2 | 5/2009 | Hooven |
| 7,738,967 B2 | 6/2010 | Salo |
| 8,103,338 B2 | 1/2012 | Harlev et al. |
| 8,150,499 B2 | 4/2012 | Gelbart et al. |
| 8,224,432 B2 | 7/2012 | MacAdam et al. |
| 8,398,626 B2 | 3/2013 | Buysee et al. |
| 2001/0003158 A1 | 6/2001 | Kensey et al. |
| 2001/0005787 A1 | 6/2001 | Oz et al. |
| 2001/0018611 A1 | 8/2001 | Solem et al. |
| 2001/0020126 A1 | 9/2001 | Swanson et al. |
| 2002/0002329 A1 | 1/2002 | Avitall |
| 2002/0016628 A1 | 2/2002 | Langberg et al. |
| 2002/0087156 A1 | 7/2002 | Maguire et al. |
| 2002/0087173 A1 | 7/2002 | Alferness et al. |
| 2002/0099415 A1 | 7/2002 | Panescu et al. |
| 2002/0107478 A1 | 8/2002 | Wendlandt |
| 2002/0107511 A1 | 8/2002 | Collins et al. |
| 2002/0115941 A1 | 8/2002 | Whayne et al. |
| 2002/0115944 A1 | 8/2002 | Mendes et al. |
| 2002/0169504 A1 | 11/2002 | Alferness et al. |
| 2002/0177782 A1 | 11/2002 | Penner |
| 2002/0183836 A1 | 12/2002 | Liddicoat et al. |
| 2002/0183841 A1 | 12/2002 | Cohn et al. |
| 2002/0188170 A1 | 12/2002 | Santamore et al. |
| 2003/0028118 A1 | 2/2003 | Dupree et al. |
| 2003/0028183 A1 | 2/2003 | Sanchez et al. |
| 2003/0050685 A1 | 3/2003 | Nikolic et al. |
| 2003/0055420 A1 | 3/2003 | Kadhiresan et al. |
| 2003/0069570 A1 | 4/2003 | Witzel et al. |
| 2003/0069573 A1 | 4/2003 | Kadhiresan et al. |
| 2003/0069636 A1 | 4/2003 | Solem et al. |
| 2003/0078465 A1 | 4/2003 | Pai et al. |
| 2003/0078671 A1 | 4/2003 | Lesniak et al. |
| 2003/0105384 A1 | 6/2003 | Sharkey et al. |
| 2003/0105520 A1 | 6/2003 | Alferness et al. |
| 2003/0109770 A1 | 6/2003 | Sharkey et al. |
| 2003/0181819 A1 | 9/2003 | Desai |
| 2003/0212395 A1 | 11/2003 | Woloszko et al. |
| 2003/0229395 A1 | 12/2003 | Cox |
| 2004/0002626 A1 | 1/2004 | Feld et al. |
| 2004/0054279 A1 | 3/2004 | Hanley |
| 2004/0133273 A1 | 7/2004 | Cox |
| 2004/0138744 A1 | 7/2004 | Lashinski et al. |
| 2004/0153146 A1 | 8/2004 | Lashinski et al. |
| 2004/0158321 A1 | 8/2004 | Reuter et al. |
| 2004/0176797 A1 | 9/2004 | Opolski |
| 2004/0186566 A1 | 9/2004 | Hindrichs et al. |
| 2004/0215232 A1 | 10/2004 | Belhe et al. |
| 2004/0243170 A1 | 12/2004 | Suresh et al. |
| 2004/0249408 A1 | 12/2004 | Murphy et al. |
| 2004/0249453 A1 | 12/2004 | Cartledge et al. |
| 2004/0267358 A1 | 12/2004 | Reitan |
| 2005/0004668 A1 | 1/2005 | Aklog et al. |
| 2005/0015109 A1 | 1/2005 | Lichtenstein |
| 2005/0054938 A1 | 3/2005 | Wehman et al. |
| 2005/0055089 A1 | 3/2005 | Macoviak et al. |
| 2005/0060030 A1 | 3/2005 | Lashinski et al. |
| 2005/0064665 A1 | 3/2005 | Han |
| 2005/0065420 A1 | 3/2005 | Collins et al. |
| 2005/0065504 A1 | 3/2005 | Melsky et al. |
| 2005/0080402 A1 | 4/2005 | Santamore et al. |
| 2005/0096047 A1 | 5/2005 | Haberman et al. |
| 2005/0096647 A1 | 5/2005 | Steinke et al. |
| 2005/0107723 A1 | 5/2005 | Wehman et al. |
| 2005/0107871 A1 | 5/2005 | Realyvasques et al. |
| 2005/0125030 A1 | 6/2005 | Forsberg et al. |
| 2005/0148892 A1 | 7/2005 | Desai |
| 2005/0149014 A1 | 7/2005 | Hauck et al. |
| 2005/0154252 A1 | 7/2005 | Sharkey et al. |
| 2005/0182365 A1 | 8/2005 | Hennemann |
| 2005/0187620 A1 | 8/2005 | Pai et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0203558 A1 | 9/2005 | Maschke |
| 2005/0209636 A1 | 9/2005 | Widomski et al. |
| 2005/0216054 A1 | 9/2005 | Widomski et al. |
| 2005/0240249 A1 | 10/2005 | Tu et al. |
| 2005/0251116 A1 | 11/2005 | Steinke et al. |
| 2005/0251132 A1 | 11/2005 | Oral et al. |
| 2005/0256521 A1 | 11/2005 | Kozel |
| 2005/0261580 A1 | 11/2005 | Willis et al. |
| 2005/0267574 A1 | 12/2005 | Cohn et al. |
| 2006/0009755 A1 | 1/2006 | Sra |
| 2006/0009756 A1 | 1/2006 | Francischelli et al. |
| 2006/0014998 A1 | 1/2006 | Sharkey et al. |
| 2006/0015002 A1 | 1/2006 | Moaddeb et al. |

(56) References Cited

U.S. PATENT DOCUMENTS

| | | |
|---|---|---|
| 2006/0015003 A1 | 1/2006 | Moaddes et al. |
| 2006/0015038 A1 | 1/2006 | Weymarn-Scharli |
| 2006/0015096 A1 | 1/2006 | Hauck et al. |
| 2006/0025800 A1 | 2/2006 | Suresh |
| 2006/0030881 A1 | 2/2006 | Sharkey et al. |
| 2006/0085049 A1 | 4/2006 | Cory et al. |
| 2006/0089637 A1 | 4/2006 | Werneth et al. |
| 2006/0135968 A1 | 6/2006 | Schaller |
| 2006/0135970 A1 | 6/2006 | Schaller |
| 2006/0184242 A1 | 8/2006 | Lichtenstein |
| 2006/0199995 A1 | 9/2006 | Vijay |
| 2006/0229491 A1 | 10/2006 | Sharkey et al. |
| 2006/0235286 A1 | 10/2006 | Stone et al. |
| 2006/0235314 A1 | 10/2006 | Migliuolo et al. |
| 2006/0264980 A1 | 11/2006 | Khairkhahan et al. |
| 2006/0281965 A1 | 12/2006 | Khairkhahan et al. |
| 2006/0293698 A1 | 12/2006 | Douk |
| 2006/0293725 A1 | 12/2006 | Rubinsky et al. |
| 2007/0016068 A1 | 1/2007 | Grunwald et al. |
| 2007/0038208 A1 | 2/2007 | Kefer |
| 2007/0083193 A1 | 4/2007 | Werneth et al. |
| 2007/0083195 A1 | 4/2007 | Werneth et al. |
| 2007/0088362 A1 | 4/2007 | Bonutti et al. |
| 2007/0115390 A1 | 5/2007 | Makara et al. |
| 2007/0118215 A1 | 5/2007 | Moaddeb |
| 2007/0129717 A1 | 6/2007 | Brown, III et al. |
| 2007/0161846 A1 | 7/2007 | Nikolic et al. |
| 2007/0198058 A1 | 8/2007 | Gelbart et al. |
| 2007/0213578 A1 | 9/2007 | Khairkhahan et al. |
| 2007/0213815 A1 | 9/2007 | Khairkhahan et al. |
| 2007/0249999 A1 | 10/2007 | Sklar et al. |
| 2007/0270688 A1 | 11/2007 | Gelbart et al. |
| 2007/0299343 A1 | 12/2007 | Waters |
| 2008/0004534 A1 | 1/2008 | Gelbart et al. |
| 2008/0004643 A1 | 1/2008 | To et al. |
| 2008/0004697 A1 | 1/2008 | Lichtenstein et al. |
| 2008/0045778 A1 | 2/2008 | Lichtenstein et al. |
| 2008/0071298 A1 | 3/2008 | Khairkhahan et al. |
| 2008/0281322 A1 | 11/2008 | Sherman et al. |
| 2008/0312713 A1 | 12/2008 | Wilfley et al. |
| 2009/0018617 A1 | 1/2009 | Skelton et al. |
| 2009/0069704 A1 | 3/2009 | MacAdam et al. |
| 2009/0131930 A1 | 5/2009 | Gelbart et al. |
| 2009/0157058 A1 | 6/2009 | Ferren et al. |
| 2009/0192441 A1 | 7/2009 | Gelbart et al. |
| 2009/0287271 A1 | 11/2009 | Blum et al. |
| 2009/0287304 A1 | 11/2009 | Dahlgren et al. |
| 2010/0204694 A1 | 8/2010 | Mehta et al. |
| 2010/0249771 A1 | 9/2010 | Pearson et al. |
| 2010/0268059 A1 | 10/2010 | Ryu et al. |
| 2011/0125172 A1 | 5/2011 | Gelbart et al. |
| 2013/0172884 A1 | 7/2013 | Schoenbach et al. |
| 2013/0310702 A1 | 11/2013 | Reinders et al. |
| 2013/0310826 A1 | 11/2013 | Goertzen et al. |
| 2013/0310827 A1 | 11/2013 | Brewster et al. |
| 2013/0310828 A1 | 11/2013 | Reinders et al. |

FOREIGN PATENT DOCUMENTS

| | | |
|---|---|---|
| WO | 95/10320 A1 | 4/1995 |
| WO | 95/20349 A1 | 8/1995 |
| WO | 97/17892 A2 | 5/1997 |
| WO | 03/015611 A2 | 2/2003 |
| WO | 03/077800 A1 | 9/2003 |
| WO | 2004/012629 A2 | 2/2004 |
| WO | 2004/047679 A1 | 6/2004 |
| WO | 2004/084746 A2 | 10/2004 |
| WO | 2004/100803 A1 | 11/2004 |
| WO | 2005/070330 A1 | 8/2005 |
| WO | 2005/102181 A1 | 11/2005 |
| WO | 2006/017809 A2 | 2/2006 |
| WO | 2006/105121 A2 | 10/2006 |
| WO | 2006/135747 A2 | 12/2006 |
| WO | 2006/135749 A2 | 12/2006 |
| WO | 2007/021647 A2 | 2/2007 |
| WO | 2007/024983 A2 | 3/2007 |
| WO | 2007/115390 A1 | 10/2007 |
| WO | 2008/002606 A2 | 1/2008 |
| WO | 2009/065042 A2 | 5/2009 |
| WO | 2012/033984 A1 | 3/2012 |
| WO | 2012/100184 A2 | 7/2012 |
| WO | 2012/100185 A2 | 7/2012 |
| WO | 2013/176880 A1 | 11/2013 |
| WO | 2013/176881 A1 | 11/2013 |

OTHER PUBLICATIONS

International Search Report and Written Opinion issued in PCT/US2013/039982 mailed Sep. 17, 2013.

International Search Report and Written Opinion issued in PCT/US2013/039977 mailed Sep. 27, 2013.

Brewster et al., "Systems and Methods for Selecting, Activating, or Selecting and Activating Transducers", Response to Restriction Requirement filed Dec. 23, 2014 for U.S. Appl. No. 13/792,670, 15 pages.

Reinders et al., "Systems and Methods for Activating Transducers", Response to Restriction Requirement filed Dec. 23, 2014 for U.S. Appl. No. 13/792,945, 16 pages.

Reinders et al., "Systems and Methods for Activating Transducers", Notice of Allowance for U.S. Appl. No. 13/792,945 mailed Jan. 27, 2015, 49 pages.

Reinders et al., "Systems and Methods for Activating Transducers", Response to Restriction Requirement filed Dec. 23, 2014 for U.S. Appl. No. 13/792,781, 15 pages.

Reinders et al., "Systems and Methods for Activating Transducers", Notice of Allowance mailed Feb. 3, 2015 for U.S. Appl. No. 13/792,781, 52 pages.

Brewster et al., "Systems and Methods for Selecting, Activating, or Selecting and Activating Transducers", Notice of Allowance mailed Feb. 4, 2015 for U.S. Appl. No. 13/792,670, 47 pages.

Partial Supplementary European Search Report issued in EP13794418.7, mailed Jun. 1, 2015.

Extended European Search Report issued in EP13793690.2, mailed May 22, 2015.

Extended European Search Report issued in EP13794418.7, mailed Sep. 16, 2015, 12 pages.

Reinders et al., "Systems and Methods for Activating Transducers", Non-Final Office Action mailed Sep. 30, 2015 for U.S. Appl. No. 14/686,457, 54 pages.

Brewster et al., "Systems and Methods for Selecting, Activating, or Selecting and Activating Transducers", Non-Final Office Action mailed Oct. 2, 2015 for U.S. Appl. No. 14/686,408, 53 pages.

Becker, et al., "Ablation of Atrial Fibrillation: Energy Sources and Navigation Tools: A Review", Journal of Electrocardiology, Supplement 2004, pp. 55-62, vol. 37.

Buchbinder, Maurice, "Dynamic Mitral Valve Annuloplasty: A Reshapable Ring for Residual and Recurring MR", Foundation for Cardiovascular Medicine, May 24, 2007.

Calkins, Hugh, "Electrophysiology: Radiofrequency Catheter Ablation of Supraventricular Arrhythmias", Education in Heart, 2001; pp. 594-600, vol. 85.

De Ponti, et al., "Non-Fluoroscopic Mapping Systems for Electrophysiology: the Tool or Toy Dilemma After 10 Years", European Heart Journal, 2006; pp. 1134-1136, vol. 27.

Gabriel, et al., "The Dielectric Properties of Biological Tissues: I. Literature Survey", Phys. Med. Biol.; 1996, pp. 2231-2249, vol. 41.

Konings, et al., "Development of an Intravascular Impedance Catheter for Detection of Fatty Lesions in Arteries", IEEE Transactions on Medical Imaging, Aug. 1997, pp. 439-446, vol. 16, No. 4.

Mack, Michael J., "New Techniques for Percutaneous Repair of the Mitral Valve", Heart Fail Rev, 2006; pp. 259-268, vol. 11.

Otasevic, et al., "First-in-Man Implantation of Left Ventricular Partitioning Device in a Patient With Chronic Heart Failure: Twelve-Month Follow-Up", Journal of Cardiac Failure, 2007, pp. 517-520, vol. 13, No. 7.

Sharkey, et al., "Left Ventricular Apex Occluder. Description of a Ventricular Partitioning Device", EuroIntervention, 2006, pp. 125-127.

(56) References Cited

OTHER PUBLICATIONS

Stiles, et al. "Simulated Characterization of Atherosclerotic Lesions in the Coronary Arteries by Measurement of Bioimpedance", IEEE Transactions on Biomedical Engineering, Jul. 2003, pp. 916-921, vol. 50, No. 7.
Tanaka, et al., "Artificial SMA Valve for Treatment of Urinary Incontinence: Upgrading of Valve and Introduction of Transcutaneous Transformer", Bio-Medical Materials and Engineering; 1999, pp. 97-112, vol. 9.
Timek, et al., "Septal-Lateral Annular Cinching Abolishes Acute Ischemic Mitral Regurgitation", Journal of Thoracic and Cardiovascular Surgery, May 2002, pp. 881-888, vol. 123, No. 5.
Timek, et al., "Septal-Lateral Annular Cinching (SLAC) Reduces Mitral Annular Size Without Perturbing Normal Annular Dynamics", Journal of Heart Valve Disease, Jan. 2002, vol. 11, No. 1, pp. 1-9.
Valvano, et al., "Thermal Conductivity and Diffusivity of Biomaterials Measured with Self-Heated Thermistors", International Journal of Thermophysics, 1985, pp. 301-311, vol. 6, No. 3.
Prosecution Documents for U.S. Appl. No. 11/436,584, now abandoned.
Prosecution Documents for U.S. Appl. No. 11/941,819, now published as US 2009-0131930 A1.
Prosecution Documents for U.S. Appl. No. 12/010,458, now published as US 2009-0192441 A1.
Prosecution Documents for U.S. Appl. No. 12/950,871, now patented as U.S. Pat. No. 8,150,499.
Specification and Drawings of U.S. Appl. No. 10/690,131.
International Search Report issued in PCT/US2007/014902 mailed Dec. 5, 2007, 5 pages.
International Search Report issued in PCT/US2008/083644 mailed Dec. 2, 2009, 5 pages.
International Preliminary Report on Patentability issued in PCT/US2007/014902 mailed Jan. 6, 2009, 8 pages.
Written Opinion issued in PCT/US2007/014902 mailed Dec. 5, 2007, 7 pages.
Written Opinion issued in PCT/US2008/083644 mailed Dec. 2, 2009, 9 pages.
"Waveforms and Segments", Ensite System Instructions for use, 54-06154-001 Rev02, Chapter 7, pp. 85-90 © 2007 St. Jude Medical.
Goertzen et al., "Systems and Methods for Selecting, Activating, or Selecting and Activating Transducers", Office Action for U.S. Appl. No. 13/792,596 mailed Nov. 24, 2015, 64 pages.

SYSTEMS AND METHODS FOR ACTIVATING TRANSDUCERS

CROSS-REFERENCE TO RELATED APPLICATIONS

This application is a continuation of U.S. Non-Provisional application Ser. No. 14/546,683, filed Nov. 18, 2014, which is a continuation-in-part of U.S. Non-Provisional application Ser. No. 13/792,781, filed Mar. 11, 2013, which claims priority benefit of each of (a) U.S. Provisional Application No. 61/723,311, filed Nov. 6, 2012, (b) U.S. Provisional Application No. 61/670,881, filed Jul. 12, 2012, and (c) U.S. Provisional Application No. 61/649,734, filed May 21, 2012, the entire disclosure of each of the applications cited in the sentence is hereby incorporated herein by reference.

TECHNICAL FIELD

Aspects of this disclosure generally are related to systems and methods for activating transducers, such systems and methods applicable to, among other things, medical systems.

BACKGROUND

Cardiac surgery was initially undertaken using highly invasive open procedures. A sternotomy, which is a type of incision in the center of the chest that separates the sternum was typically employed to allow access to the heart. In the past several decades, more and more cardiac operations are performed using intravascular or percutaneous techniques, where access to inner organs or other tissue is gained via a catheter.

Intravascular or percutaneous surgeries benefit patients by reducing surgery risk, complications and recovery time. However, the use of intravascular or percutaneous technologies also raises some particular challenges. Medical devices used in intravascular or percutaneous surgery need to be deployed via catheter systems which significantly increase the complexity of the device structure. As well, doctors do not have direct visual contact with the medical devices once the devices are positioned within the body.

One example of where intravascular or percutaneous medical techniques have been employed is in the treatment of a heart disorder called atrial fibrillation. Atrial fibrillation is a disorder in which spurious electrical signals cause an irregular heartbeat. Atrial fibrillation has been treated with open heart methods using a technique known as the "Cox-Maze procedure". During this procedure, physicians create specific patterns of lesions in the left or right atria to block various paths taken by the spurious electrical signals. Such lesions were originally created using incisions, but are now typically created by ablating the tissue with various techniques including radio-frequency (RF) energy, microwave energy, laser energy and cryogenic techniques. The procedure is performed with a high success rate under the direct vision that is provided in open procedures, but is relatively complex to perform intravascularly or percutaneously because of the difficulty in creating the lesions in the correct locations. Various problems, potentially leading to severe adverse results, may occur if the lesions are placed incorrectly. It is particularly important to know the position of the various transducers which will be creating the lesions relative to cardiac features such as the pulmonary veins and mitral valve. The continuity, transmurality and placement of the lesion patterns that are formed can impact the ability to block paths taken within the heart by spurious electrical signals. Other requirements for various ones of the transducers to perform additional functions such as, but not limited to, mapping various anatomical features, mapping electrophysiological activity, sensing tissue characteristics such as impedance and temperature and tissue stimulation can also complicate the operation of the employed medical device.

In this regard, there is a need for intra-bodily-cavity transducer-based devices with improved performance and reduced complexity as compared to conventional devices.

SUMMARY

At least the above-discussed need is addressed and technical solutions are achieved by various embodiments of the present invention. In some embodiments, device systems and methods executed by such systems exhibit enhanced capabilities for the activation of various transducers, which may be located within a bodily cavity, such as an intracardiac cavity. In some embodiments, the systems or a portion thereof may be percutaneously or intravascularly delivered to position the various transducers within the bodily cavity. Various ones of the transducers may be activated to distinguish tissue from blood and may be used to deliver positional information of the device relative to various anatomical features in the bodily cavity, such as the pulmonary veins and mitral valve in an atrium. Various ones of the transducers may employ characteristics such as blood flow detection, impedance change detection or deflection force detection to discriminate between blood and tissue. Various ones of the transducers may be used to treat tissue within a bodily cavity. Treatment may include tissue ablation by way of non-limiting example. Various ones of the transducers may be used to stimulate tissue within the bodily cavity. Stimulation can include pacing by way of non-limiting example. Other advantages will become apparent from the teaching herein to those of skill in the art.

In some embodiments, a transducer-activation system may be summarized as including a data processing device system, an input-output device system communicatively connected to the data processing device system, and a memory device system communicatively connected to the data processing device system and storing a program executable by the data processing device system. The program may include reception instructions configured to cause reception of a selection from the input-output device system of at least some of a plurality of transducers of a transducer-based device, the plurality of transducers arranged in a distribution, the distribution positionable in a bodily cavity. The program may include generation instructions configured to, in response to receiving at least part of the selection, cause generation of a plurality of transducer sets from the at least some of the plurality of transducers. The plurality of transducer sets may include at least a first transducer set and one or more other transducer sets. The first transducer set may include at least a first transducer of the at least some of the plurality of transducers and a second transducer of the at least some of the plurality of transducers. Each of the one or more other transducer sets may include the first transducer, the second transducer, or both the first transducer and the second transducer. The first transducer may be included in the one or more other transducer sets. The second transducer may be included in the one or more other transducer sets. Each of at least one of the plurality of transducer sets may include a different transducer than each of at least one other set of the plurality of transducer sets. The program may further include activation instructions configured to, in response to receiving at least part of the selection, cause activation of each respective transducer set of the plurality of transducer sets. The activation of each respective transducer set of the plurality of transducer sets may include the activation of each respective transducer in the respective transducer set. The activation instructions may be configured to cause the activation of each respective transducer in each respective transducer set of the plurality of transducer sets to begin at a different time than the activation of each respective transducer in another respective transducer set of the plurality of transducer sets. The activation instructions may be configured to cause a delay of the activation of each respective transducer in the first transducer set with respect to a start of the activation of each respective transducer in each of the one or more other transducer sets.

In some embodiments, (a) the first transducer set may include a different transducer than each of at least one of the one or more other transducer sets, or (b) at least one of the one or more other transducer sets may include a different transducer than (i) the first transducer set or (ii) each of at least another of the one or more other transducer sets.

In some embodiments, the activation instructions may be configured to cause at least a portion of the activation of each respective transducer in the first transducer set to occur concurrently with every other transducer in the first transducer set. In some embodiments the activation instructions may be configured to cause concurrent initiation of the activation of the transducers in the first transducer set. In some embodiments, the activation instructions may be configured to cause at least a portion of the activation of each respective transducer in at least a particular one of the plurality of transducer sets to occur concurrently with the activation of every transducer in the first transducer set, the particular one of the plurality of transducer sets including two or more of the plurality of transducers. In some embodiments, the activation instructions may be configured to cause, for a particular one of the one or more other transducer sets, an initiation of the activation of each of at least two transducers in the particular one of the one or more other transducer sets to occur concurrently, the particular one of the one or more other transducer sets including two or more of the plurality of transducers.

In some embodiments, the activation instructions may be configured to cause, for a particular one of the one or more other transducer sets, an initiation of the activation of at least one transducer in the particular one of the one or more other transducer sets to occur sequentially with an initiation of the activation of at least another transducer in the particular one of the one or more other transducer sets, the particular one of the one or more other transducer sets including two or more of the plurality of transducers. In some embodiments, the one or more other transducer sets may include two or more other transducer sets, and the activation instructions may be configured to cause, for a first particular one of the two or more other transducer sets, an initiation of the activation of at least one transducer in the first particular one of the two or more other transducer sets to occur concurrently with an initiation of the activation of at least one transducer in a second particular one of the one or more other transducer sets.

In some embodiments, the one or more other transducer sets may include two or more other transducer sets, and the activation instructions may be configured to cause, for a first particular one of the two or more other transducer sets, an initiation of the activation of at least one transducer in the first particular one of the two or more other transducer sets to occur at a different time with respect to an initiation of the activation of at least one transducer in a second particular one of the two or more other transducer sets. The at least one transducer in the first particular one of the two or more other transducer sets may include a third transducer other than each of the first transducer and the second transducer, and the at least one transducer in the second particular one of the two or more other transducer sets may include the third transducer.

In some embodiments, the one or more other transducer sets may include two or more other transducer sets, and a particular one of the two or more other transducers sets may include only a single transducer. In some embodiments, each of at least one of the one or more other transducer sets may include at least two transducers. In some embodiments, the selected at least some of the transducers in the distribution may include some but not all of the transducers in the distribution.

In some embodiments, the input-output device system may include the plurality of transducers. The distribution may be an arrayed distribution including a plurality of intersecting rows and columns. A respective group of the plurality of transducers may be arranged along each of the rows and a respective group of the plurality of transducers may be arranged along each of the columns. The first transducer may be located on a first particular one of the columns and the second transducer may be located on a second particular one of the columns. At least one other of the columns may be arranged between the first particular one of the columns and the second particular one of the columns. In some embodiments, the first transducer and the second transducer may be located on a same particular one of the rows. In some embodiments, the first transducer may be located on a first particular one of the rows and the second transducer may be located on a second particular one of the rows other than the first particular one of the rows. In some embodiments, the one or more other transducer sets may include at least one transducer other than the first transducer and the second transducer, the at least one transducer other than the first transducer and the second transducer located on one of the columns other than the first particular one of the columns and the second particular one of the columns. In some embodiments, the first transducer and the second transducer may be located on a same particular one of the rows, and the one or more other transducer sets may include at least one transducer other than the first transducer and the second transducer, the at least one transducer other than the first transducer and the second transducer located on one of the rows other than the same particular one of the rows. In some embodiments, the first transducer and the second transducer may be located on a same particular one of the rows, and the one or more other transducer sets may include at least one transducer other than the first transducer, the at least one transducer other than the first transducer located on the first particular one of the columns, and the one or more other transducer sets may include at least one transducer other than the first transducer and the second transducer, the at least one transducer other than the first transducer and the second transducer located on the same particular one of the rows.

In some embodiments, the input-output device system may include a transducer-based system, which includes the plurality of transducers. The distribution may be an array-based distribution that includes a plurality of intersecting rows and columns. Adjacent ones of the rows may be separated from each other at least by a physical portion of the transducer-based system, and adjacent ones of the columns may be separated from each other at least by a non-physical portion of the transducer-based system. The first transducer may be located on a first particular one of the columns, and the second transducer may be located on a second particular one of the columns. In some embodiments, at least one of the columns, other than the first particular one of the columns and the second particular one of the columns, may be arranged between the first particular one of the columns and the second particular one of the columns. In some embodiments, the first transducer and the second transducer may be located on a same particular one of the rows. In some embodiments, the one or more other transducer sets may include at least one transducer other than the first transducer and the second transducer, the at least one transducer other than the first transducer and the second transducer located on one of the columns other than the first particular one of the columns and the second particular one of the columns. In some embodiments, the first transducer and the second transducer may be located on a same particular one of the rows, and the one or more other transducer sets may include at least one transducer other than the first transducer and the second transducer, the at least one transducer other than the first transducer and the second transducer located on one of the rows other than the same particular one of the rows. In some embodiments, the first transducer and the second transducer may be located on a same particular one of the rows, and the one or more other transducer sets may include at least one transducer other than the first transducer, the at least one transducer other than the first transducer located on the first particular one of the columns. The one or more other transducer sets may further include at least one transducer other than the first transducer and the second transducer, the at least one transducer other than the first transducer and the second transducer located on the same particular one of the rows.

In some embodiments, the program may further include display instructions configured to cause the input-output device system to concurrently display at least a map depicting a surface of a tissue wall of the bodily cavity, the surface interrupted by one or more openings, and a plurality of transducer graphical elements, each of the transducer graphical elements corresponding to at least part of a respective one of the plurality of transducers, a first spatial arrangement between the displayed transducer graphical elements consistent with a second spatial relationship between the transducers. The display instructions may be configured to display the respective transducer graphical elements corresponding to the selected at least some of the transducers in the distribution surrounding at least one of the one or more ports depicted in the map. The program may further include information reception instructions configured to cause reception via the input-output device system of information from each of the plurality of transducers, and the display instructions may be configured to display the map based at least on the information received from the each of the plurality of transducers.

In some embodiments, the program may further include display instructions configured to cause the input-output device system to concurrently display a plurality of transducer graphical elements, each of the transducer graphical elements corresponding to at least part of a respective one of the plurality of transducers, a first spatial arrangement between the displayed transducer graphical elements consistent with a second spatial relationship between the transducers, and a plurality of between graphical elements, each of the plurality of between graphical elements associated with a region of space between the transducers of a respective one of a plurality of groups of adjacent ones of the transducers. Each region of space may not include any transducer. The display instructions may be configured to display the respective transducer graphical elements corresponding to transducers activated according to the activation instructions in a manner different than the display of others of the transducer graphical elements, the respective transducer graphical elements corresponding to the transducers activated according to the activation instructions being selected transducer graphical elements. The display instructions may be configured to display the respective between graphical elements between respective groups of adjacent ones of the selected transducer graphical elements in a manner different than the display of others of the between graphical elements. The input-output device system may include a transducer-based system, which includes the plurality of transducers, and at least one of the between graphical elements may be associated with a region of space that is not associated with any physical part of the transducer-based system. The region of space that is not associated with any physical part of the transducer-based system may be between the transducers of a particular one of the plurality of groups of adjacent ones of the transducers that includes the first transducer and the second transducer.

Reception, via the input-output device system, of the selected at least some of the transducers in the distribution may include reception of a user-based selection, via the input-output device system, of the selected at least some of the transducers in the distribution in some embodiments. The generation instructions configured to generate the plurality of transducer sets from the selected at least some of the plurality of transducers may include machine-based selections from the selected at least some of the plurality of transducers in some embodiments.

In some embodiments, the transducer-activation system may further include the transducer-based device. In some embodiments, the activation instructions may be configured to cause concurrent monopolar activation of all of the transducers in the first transducer set. In some embodiments, the activation instructions may be configured to cause, for each particular one of the plurality of transducer sets that includes two or more of the plurality of transducers, concurrent monopolar activation of all of the transducers in the particular one of the plurality of transducer sets that includes two or more of the plurality of transducers.

Various systems may include combinations and subsets of all the systems summarized above or otherwise described herein.

In some embodiments, a transducer-activation system may be summarized as including a data processing device system, an input-output device system communicatively connected to the data processing device system, and a memory device system communicatively connected to the data processing device system and storing a program executable by the data processing device system. The data processing device system may be configured by the program at least to receive a selection from the input-output device system of at least some of a plurality of transducers of a transducer-based device, the plurality of transducers arranged in a distribution, the distribution positionable in a bodily cavity. The data processing device system may be configured by the program to generate, in response to receiving at least part of the selection, a plurality of transducer sets from the at least some of the plurality of transducers, the plurality of transducer sets including at least a first transducer set and one or more other transducer sets. The first transducer set may include at least a first transducer of the at least some of the plurality of transducers and a second transducer of the at least some of the plurality of transducers. Each of the one or more other transducer sets may include the first transducer, the second transducer, or both the first transducer and the second transducer. The first transducer may be included in the one or more other transducer sets. The second transducer may be included in the one or more other transducer sets. Each of at least one of the plurality of transducer sets may include a different transducer than each of at least one other set of the plurality of transducer sets. The data processing device system may be configured by the program to activate, in response to receiving at least part of the selection, each respective transducer set of the plurality of transducer sets. The activation of each respective transducer set of the plurality of transducer sets may include the activation of each respective transducer in the respective transducer set. The activation of each respective transducer in each respective transducer set of the plurality of transducer sets may begin at a different time than the activation of each respective transducer in another respective transducer set of the plurality of transducer sets, and the activation of each respective transducer in the first transducer set may be delayed with respect to a start of the activation of each respective transducer in each of the one or more other transducer sets.

Various systems may include combinations and subsets of all the systems summarized above or otherwise described herein.

In some embodiments, a computer-readable data storage medium system may be summarized as including one or more computer-readable data storage mediums storing a program executable by one or more data processing devices of a data processing device system communicatively connected to an input-output device system. The program may include reception instructions configured to cause reception of a selection from the input-output device system of at least some of a plurality of transducers of a transducer-based device, the plurality of transducers arranged in a distribution, the distribution positionable in a bodily cavity. The program may include generation instructions configured to, in response to receiving at least part of the selection, cause generation of a plurality of transducer sets from the at least some of the plurality of transducers. The plurality of transducer sets may include at least a first transducer set and one or more other transducer sets. The first transducer set may include at least a first transducer of the at least some of the plurality of transducers and a second transducer of the at least some of the plurality of transducers. Each of the one or more other transducer sets may include the first transducer, the second transducer, or both the first transducer and the second transducer. The first transducer may be included in the one or more other transducer sets. The second transducer may be included in the one or more other transducer sets. Each of at least one of the plurality of transducer sets may include a different transducer than each of at least one other set of the plurality of transducer sets. The program may include activation instructions configured to, in response to receiving at least part of the selection, cause activation of each respective transducer set of the plurality of transducer sets, the activation of each respective transducer set of the plurality of transducer sets including the activation of each respective transducer in the respective transducer set. The activation instructions may be configured to cause the activation of each respective transducer in each respective transducer set of the plurality of transducer sets to begin at a different time than the activation of each respective transducer in another respective transducer set of the plurality of transducer sets. The activation instructions may be configured to cause a delay of the activation of each respective transducer in the first transducer set with respect to a start of the activation of each respective transducer in each of the one or more other transducer sets.

In some embodiments, a transducer-activation method may be summarized as including selecting, via an input-output device system communicatively connected to a data processing device system and a transducer-based device, a plurality of transducer sets from at least some of a plurality of transducers of the transducer-based device, the plurality of transducers arranged in a distribution, the distribution positionable in a bodily cavity. The plurality of transducer sets may include at least a first transducer set and one or more other transducer sets. The first transducer set may include at least a first transducer of the at least some of the plurality of transducers and a second transducer of the at least some of the plurality of transducers. Each of the one or more other transducer sets may include the first transducer, the second transducer, or both the first transducer and the second transducer. The first transducer may be included in the one or more other transducer sets. The second transducer may be included in the one or more other transducer sets. Each of at least one of the plurality of transducer sets may include a different transducer than each of at least one other set of the plurality of transducer sets. The method may include activating, via the input-output device system, each respective transducer set of the plurality of transducer sets, the activating of each respective transducer set of the plurality of transducer sets including activating each respective transducer in the respective transducer set. The activating of each respective transducer in each respective transducer set of the plurality of transducer sets may begin at a different time than the activating of each respective transducer in another respective transducer set of the plurality of transducer sets. The method may include delaying the activating of each respective transducer in the first transducer set with respect to a start of the activating of each respective transducer in each of the one or more other transducer sets.

In some embodiments, a transducer-activation method may be summarized as including selecting, via an input-output device system communicatively connected to a data processing device system and a transducer-based device, at least some of a plurality of transducers of the transducer-based device, the plurality of transducers arranged in a distribution, the distribution positionable in a bodily cavity. The at least some of the plurality of transducers may define a plurality of transducer sets including at least a first transducer set, a second transducer set, and a third transducer set. The method may include activating, via the input-output device system, the plurality of transducer sets according to a sequence, at least a portion of the activating according to the sequence including an initiation of an activation of each transducer in the first transducer set after each transducer in at least the second transducer set and the third transducer set has been activated. Each of at least one of the first transducer set, the second transducer set, and the third transducer set may include at least one transducer of the at least some of the plurality of transducers different than each respective transducer included in each of at least one other of the first, the second, and the third transducer sets. The first transducer set may include at least a first transducer of the at least some of the plurality of transducers and a second transducer of the at least some of the plurality of transducers. The second transducer set may include at least the first transducer, and the third transducer set may include at least the second transducer.

Any of the features of any of the methods discussed herein may be combined with any of the other features of any of the methods discussed herein. In addition, a computer program product may be provided that comprises program code portions for performing some or all of any of the methods and associated features thereof described herein, when the computer program product is executed by a computer or other computing device or device system. Such a computer program product may be stored on one or more computer-readable storage mediums.

In some embodiments, each of any or all of the computer-readable storage mediums or medium systems described herein is a non-transitory computer-readable storage medium or medium system including one or more non-transitory computer-readable storage mediums storing the respective program(s).

Further, any or all of the methods and associated features thereof discussed herein may be implemented by all or part of a device system or apparatus, such as any of those described herein.

BRIEF DESCRIPTION OF THE DRAWINGS

It is to be understood that the attached drawings are for purposes of illustrating aspects of various embodiments and may include elements that are not to scale.

DETAILED DESCRIPTION

Figure 1:
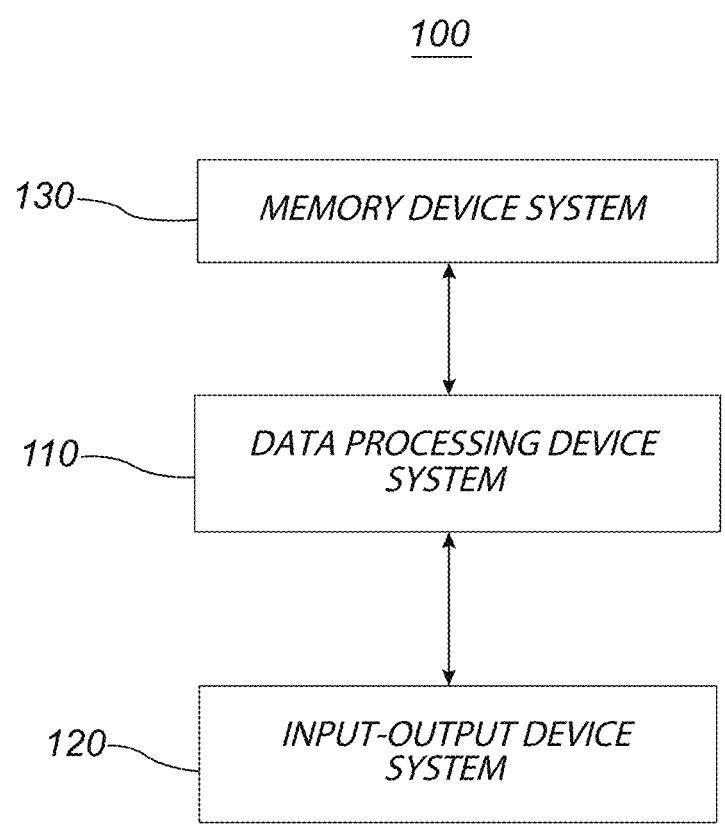
FIG. 1 illustrates a schematic representation of a transducer-activation system according to various example embodiments, the transducer-activation system including a data processing device system, an input-output device system, and a memory device system.

In the following description, certain specific details are set forth in order to provide a thorough understanding of various embodiments of the invention. However, one skilled in the art will understand that the invention may be practiced without these details. In other instances, well-known structures (e.g., structures associated with radio-frequency (RF) ablation and electronic controls such as multiplexers) have not been shown or described in detail to avoid unnecessarily obscuring descriptions of various embodiments of the invention.

Reference throughout this specification to "one embodiment" or "an embodiment" or "an example embodiment" or "an illustrated embodiment" or "a particular embodiment" and the like means that a particular feature, structure or characteristic described in connection with the embodiment is included in at least one embodiment. Thus, the appearances of the phrases "in one embodiment" or "in an embodiment" or "in an example embodiment" or "in this illustrated embodiment" or "in this particular embodiment" and the like in various places throughout this specification are not necessarily all referring to one embodiment or a same embodiment. Furthermore, the particular features, structures or characteristics of different embodiments may be combined in any suitable manner to form one or more other embodiments.

It is noted that, unless otherwise explicitly noted or required by context, the word "or" is used in this disclosure in a non-exclusive sense. In addition, unless otherwise explicitly noted or required by context, the word "set" is intended to mean one or more.

Further, the phrase "at least" is used herein at times to emphasize the possibility that other elements can exist besides those explicitly listed. However, unless otherwise explicitly noted (such as by the use of the term "only") or required by context, non-usage herein of the phrase "at least" does not exclude the possibility that other elements can exist besides those explicitly listed. For example, the phrase, "activation of at least transducer A" includes activation of transducer A by itself, as well as activation of transducer A and activation of one or more other additional elements besides transducer A. In the same manner, the phrase, "activation of transducer A" includes activation of transducer A by itself, as well as activation of transducer A and activation of one or more other additional elements besides transducer A. However, the phrase, "activation of only transducer A" includes only activation of transducer A, and excludes activation of any other transducers besides transducer A.

The word "ablation" as used in this disclosure should be understood to include any disruption to certain properties of tissue. Most commonly, the disruption is to the electrical conductivity and is achieved by heating, which can be generated with resistive or radio-frequency (RF) techniques for example. Other properties, such as mechanical or chemical, and other means of disruption, such as optical, are included when the term "ablation" is used.

The word "fluid" as used in this disclosure should be understood to include any fluid that can be contained within a bodily cavity or can flow into or out of, or both into and out of a bodily cavity via one or more bodily openings positioned in fluid communication with the bodily cavity. In the case of cardiac applications, fluid such as blood will flow into and out of various intra-cardiac cavities (e.g., a left atrium or right atrium).

The words "bodily opening" as used in this disclosure should be understood to include a naturally occurring bodily opening or channel or lumen; a bodily opening or channel or lumen formed by an instrument or tool using techniques that can include, but are not limited to, mechanical, thermal, electrical, chemical, and exposure or illumination techniques; a bodily opening or channel or lumen formed by trauma to a body; or various combinations of one or more of the above. Various elements having respective openings, lumens or channels and positioned within the bodily opening (e.g., a catheter sheath) may be present in various embodiments. These elements may provide a passageway through a bodily opening for various devices employed in various embodiments.

The words "bodily cavity" as used in this disclosure should be understood to mean a cavity in a body. The bodily cavity may be a cavity provided in a bodily organ (e.g., an intra-cardiac cavity of a heart).

The word "tissue" as used in some embodiments in this disclosure should be understood to include any surface-forming tissue that is used to form a surface of a body or a surface within a bodily cavity, a surface of an anatomical feature or a surface of a feature associated with a bodily opening positioned in fluid communication with the bodily cavity. The tissue can include part or all of a tissue wall or membrane that defines a surface of the bodily cavity. In this regard, the tissue can form an interior surface of the cavity that surrounds a fluid within the cavity. In the case of cardiac applications, tissue can include tissue used to form an interior surface of an intra-cardiac cavity such as a left atrium or right atrium. In some embodiments, the word tissue can refer to a tissue having fluidic properties (e.g., blood).

The term "transducer" as used in this disclosure should be interpreted broadly as any device capable of distinguishing between fluid and tissue, sensing temperature, creating heat, ablating tissue, measuring electrical activity of a tissue surface, stimulating tissue, or any combination thereof. A transducer can convert input energy of one form into output energy of another form. Without limitation, a transducer can include an electrode that functions as, or as part of, a sensing device included in the transducer, an energy delivery device included in the transducer, or both a sensing device and an energy delivery device included in the transducer. A transducer may be constructed from several parts, which may be discrete components or may be integrally formed. In this regard, although transducers, electrodes, or both transducers and electrodes are referenced with respect to various embodiments, it is understood that other transducers or transducer elements may be employed in other embodiments. It is understood that a reference to a particular transducer in various embodiments may also imply a reference to an electrode, as an electrode may be part of the transducer as shown, e.g., with FIG. 4 discussed below.

The term "activation" as used in this disclosure should be interpreted broadly as making active a particular function as related to various transducers disclosed in this disclosure. Particular functions can include, but are not limited to, tissue ablation, sensing electrophysiological activity, sensing temperature and sensing electrical characteristics (e.g., tissue impedance). For example, in some embodiments, activation of a tissue ablation function of a particular transducer is initiated by causing energy sufficient for tissue ablation from an energy source device system to be delivered to the particular transducer. Alternatively, in this example, the activation can be deemed to be initiated when the particular transducer causes a temperature sufficient for the tissue ablation due to the energy provided by the energy source device system. Also in this example, the activation can last for a duration of time concluding when the ablation function is no longer active, such as when energy sufficient for the tissue ablation is no longer provided to the particular transducer. Alternatively, in this example, the activation period can be deemed to be concluded when the temperature caused by the particular transducer is below the temperature sufficient for the tissue ablation. In some contexts, however, the word "activation" can merely refer to the initiation of the activating of a particular function, as opposed to referring to both the initiation of the activating of the particular function and the subsequent duration in which the particular function is active. In these contexts, the phrase or a phrase similar to "activation initiation" may be used.

The term "program" in this disclosure should be interpreted as a set of instructions or modules that can be executed by one or more components in a system, such a controller system or data processing device system, in order to cause the system to perform one or more operations. The set of instructions or modules can be stored by any kind of memory device, such as those described subsequently with respect to the memory device system 130 shown in FIG. 1. In addition, this disclosure sometimes describes that the instructions or modules of a program are configured to cause the performance of a function. The phrase "configured to" in this context is intended to include at least (a) instructions or modules that are presently in a form executable by one or more data processing devices to cause performance of the function (e.g., in the case where the instructions or modules are in a compiled and unencrypted form ready for execution), and (b) instructions or modules that are presently in a form not executable by the one or more data processing devices, but could be translated into the form executable by the one or more data processing devices to cause performance of the function (e.g., in the case where the instructions or modules are encrypted in a non-executable manner, but through performance of a decryption process, would be translated into a form ready for execution). The word "module" can be defined as a set of instructions.

The word "device" and the phrase "device system" both are intended to include one or more physical devices or sub-devices (e.g., pieces of equipment) that interact to perform one or more functions, regardless of whether such devices or sub-devices are located within a same housing or different housings. In this regard, for example, this disclosure sometimes refers to a "catheter device", but such catheter device could equivalently be referred to as a "catheter device system".

In some contexts, the term "adjacent" is used in this disclosure to refer to objects that do not have another substantially similar object between them. For example, object A and object B could be considered adjacent if they contact each other (and, thus, it could be considered that no other object is between them), or if they do not contact each other, but no other object that is substantially similar to object A, object B, or both objects A and B, depending on context, is between them.

Further, the phrase "in response to" commonly is used in this disclosure. For example, this phrase might be used in the following context, where an event A occurs in response to the occurrence of an event B. In this regard, such phrase can include, for example, that at least the occurrence of the event B causes or triggers the event A.

Further still, example methods are described herein with respect to FIGS. 7A, 7B, 8, 9, 10, 12, 13, 14, 15A, 15B and 16. Such figures are described to include blocks associated with instructions. It should be noted that the respective instructions associated, e.g., with each of blocks 1206A and 1206B, or any other method blocks herein, need not be separate instructions and may be combined with other instructions to form a combined instruction set. In this regard, the blocks shown in each of the method figures herein are not intended to illustrate an actual structure of any program or set of instructions, and such method figures, according to some embodiments, merely illustrate the tasks that instructions are configured to perform upon execution by a data processing device system in conjunction with interactions with one or more other devices or device systems.

FIG. 1 schematically illustrates a system 100 for activating transducers, according to some embodiments. The system 100 includes a data processing device system 110, an input-output device system 120, and a processor-accessible memory device system 130. The processor-accessible memory device system 130 and the input-output device system 120 are communicatively connected to the data processing device system 110.

The data processing device system 110 includes one or more data processing devices that implement or execute, in conjunction with other devices, such as those in the system 100, the methods of various embodiments, including the example methods of FIGS. 7A, 7B, 8, 9, 10, 12, 13, 14, 15A, 15B and 16 described herein. Each of the phrases "data processing device", "data processor", "processor", and "computer" is intended to include any data processing device, such as a central processing unit ("CPU"), a desktop computer, a laptop computer, a mainframe computer, tablet computer, a personal digital assistant, a cellular phone, and any other device for processing data, managing data, or handling data, whether implemented with electrical, magnetic, optical, biological components, or otherwise.

The memory device system 130 includes one or more processor-accessible memory devices configured to store information, including the information needed to execute the methods of various embodiments, including the example methods of FIGS. 7A, 7B, 8, 9, 10, 12, 13, 14, 15A, 15B and 16 described herein. The memory device system 130 may be a distributed processor-accessible memory device system including multiple processor-accessible memory devices communicatively connected to the data processing device system 110 via a plurality of computers and/or devices. On the other hand, the memory device system 130 need not be a distributed processor-accessible memory system and, consequently, may include one or more processor-accessible memory devices located within a single data processing device.

Each of the phrases "processor-accessible memory" and "processor-accessible memory device" is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs, and RAMs. In some embodiments, each of the phrases "processor-accessible memory" and "processor-accessible memory device" is intended to include a non-transitory computer-readable storage medium. And in some embodiments, the memory device system 130 can be considered a non-transitory computer-readable storage medium system.

The phrase "communicatively connected" is intended to include any type of connection, whether wired or wireless, between devices, data processors, or programs in which data may be communicated. Further, the phrase "communicatively connected" is intended to include a connection between devices or programs within a single data processor, a connection between devices or programs located in different data processors, and a connection between devices not located in data processors at all. In this regard, although the memory device system 130 is shown separately from the data processing device system 110 and the input-output device system 120, one skilled in the art will appreciate that the memory device system 130 may be located completely or partially within the data processing device system 110 or the input-output device system 120. Further in this regard, although the input-output device system 120 is shown separately from the data processing device system 110 and the memory device system 130, one skilled in the art will appreciate that such system may be located completely or partially within the data processing system 110 or the memory device system 130, depending upon the contents of the input-output device system 120. Further still, the data processing device system 110, the input-output device system 120, and the memory device system 130 may be located entirely within the same device or housing or may be separately located, but communicatively connected, among different devices or housings. In the case where the data processing device system 110, the input-output device system 120, and the memory device system 130 are located within the same device, the system 100 of FIG. 1 can be implemented by a single application-specific integrated circuit (ASIC) in some embodiments.

The input-output device system 120 may include a mouse, a keyboard, a touch screen, another computer, or any device or combination of devices from which a desired selection, desired information, instructions, or any other data is input to the data processing device system 110. The input-output device system may include a user-activatable control system that is responsive to a user action. The input-output device system 120 may include any suitable interface for receiving information, instructions or any data from other devices and systems described in various ones of the embodiments. In this regard, the input-output device system 120 may include various ones of other systems described in various embodiments. For example, the input-output device system 120 may include at least a portion a transducer-based device system. The phrase "transducer-based device system" is intended to include one or more physical systems that include various transducers. The phrase "transducer-based device" is intended to include one or more physical devices that include various transducers.

The input-output device system 120 also may include an image generating device system, a display device system, a processor-accessible memory device, or any device or combination of devices to which information, instructions, or any other data is output by the data processing device system 110. In this regard, if the input-output device system 120 includes a processor-accessible memory device, such memory device may or may not form part or all of the memory device system 130. The input-output device system 120 may include any suitable interface for outputting information, instructions or data to other devices and systems described in various ones of the embodiments. In this regard, the input-output device system may include various other devices or systems described in various embodiments.

Various embodiments of transducer-based devices are described herein. Some of the described devices are medical devices that are percutaneously or intravascularly deployed. Some of the described devices are moveable between a delivery or unexpanded configuration (e.g., FIG. 3A, discussed below) in which a portion of the device is sized for passage through a bodily opening leading to a bodily cavity, and an expanded or deployed configuration (e.g., FIG. 3B, discussed below) in which the portion of the device has a size too large for passage through the bodily opening leading to the bodily cavity. An example of an expanded or deployed configuration is when the portion of the transducer-based device is in its intended-deployed-operational state inside the bodily cavity. Another example of the expanded or deployed configuration is when the portion of the transducer-based device is being changed from the delivery configuration to the intended-deployed-operational state to a point where the portion of the device now has a size too large for passage through the bodily opening leading to the bodily cavity.

In some example embodiments, the device includes transducers that sense characteristics (e.g., convective cooling, permittivity, force) that distinguish between fluid, such as a fluidic tissue (e.g., blood), and tissue forming an interior surface of the bodily cavity. Such sensed characteristics can allow a medical system to map the cavity, for example using positions of openings or ports into and out of the cavity to determine a position or orientation (e.g., pose), or both of the portion of the device in the bodily cavity. In some example embodiments, the described devices are capable of ablating tissue in a desired pattern within the bodily cavity. In some example embodiments, the devices are capable of sensing characteristics (e.g., electrophysiological activity) indicative of whether an ablation has been successful. In some example embodiments, the devices are capable of providing stimulation (e.g., electrical stimulation) to tissue within the bodily cavity. Electrical stimulation may include pacing.

Figure 2:
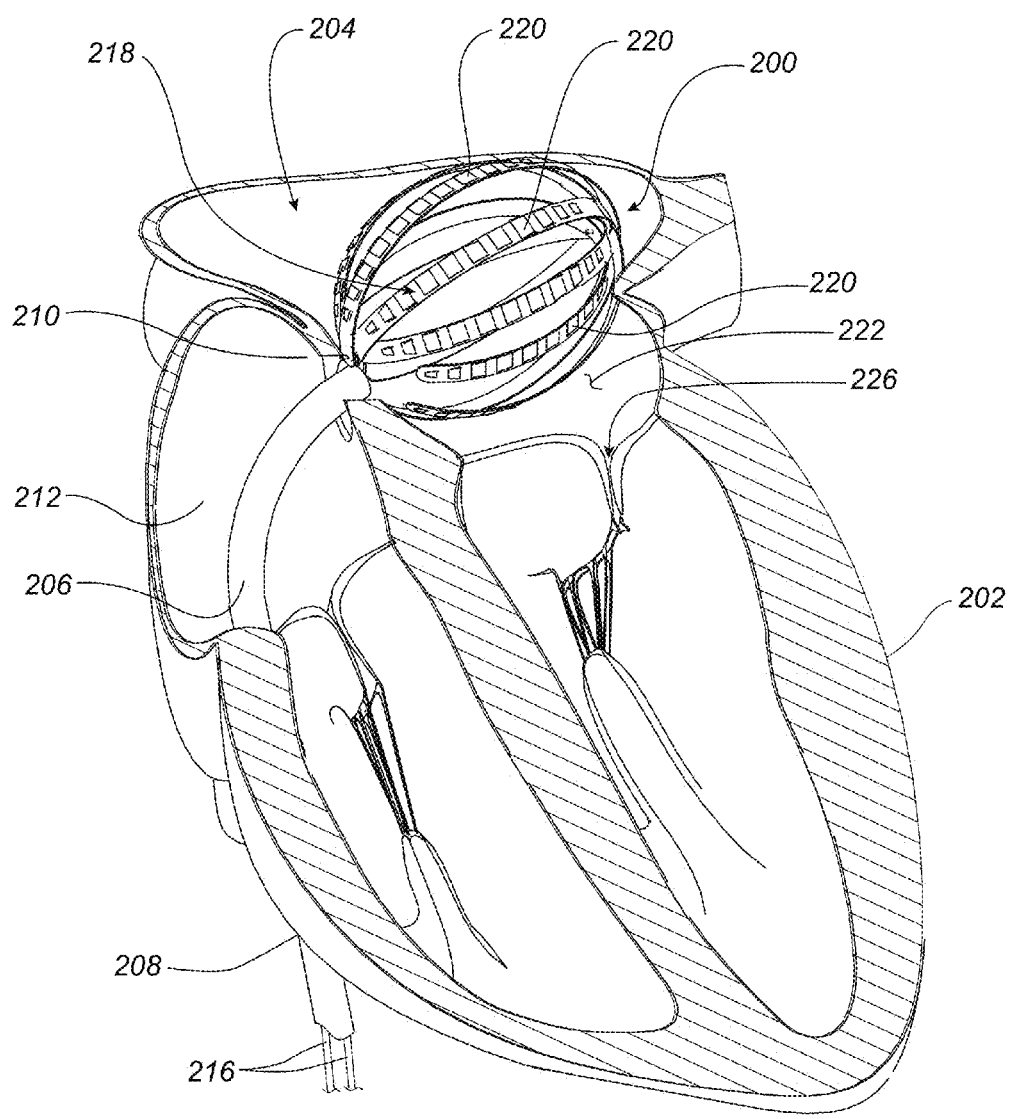
FIG. 2 illustrates a cutaway diagram of a heart showing a transducer-based device percutaneously placed in a left atrium of the heart according to various example embodiments.

FIG. 2 is a representation of a transducer-based device 200 useful in investigating or treating a bodily organ, for example a heart 202, according to one example embodiment.

Transducer-based device 200 can be percutaneously or intravascularly inserted into a portion of the heart 202, such as an intra-cardiac cavity like left atrium 204. In this example, the transducer-based device 200 is part of a catheter 206 inserted via the inferior vena cava 208 and penetrating through a bodily opening in transatrial septum 210 from right atrium 212. In other embodiments, other paths may be taken.

Catheter 206 includes an elongated flexible rod or shaft member appropriately sized to be delivered percutaneously or intravascularly. Various portions of catheter 206 may be steerable. Catheter 206 may include one or more lumens (not shown). The lumen(s) may carry one or more communications or power paths, or both. For example, the lumens(s) may carry one or more electrical conductors 216 (two shown in this embodiment). Electrical conductors 216 provide electrical connections to device 200 that are accessible externally from a patient in which the transducer-based device 200 is inserted.

Transducer-based device 200 includes a frame or structure 218 which assumes an unexpanded configuration for delivery to left atrium 204. Structure 218 is expanded (e.g., shown in a deployed or expanded configuration in FIG. 2) upon delivery to left atrium 204 to position a plurality of transducers 220 (three called out in FIG. 2) proximate the interior surface formed by tissue 222 of left atrium 204. In this example embodiment, at least some of the transducers 220 are used to sense a physical characteristic of a fluid (e.g., blood) or tissue 222, or both, that may be used to determine a position or orientation (e.g., pose), or both, of a portion of a device 200 within, or with respect to left atrium 204. For example, transducers 220 may be used to determine a location of pulmonary vein ostia (not shown) or a mitral valve 226, or both. In this example embodiment, at least some of the transducers 220 may be used to selectively ablate portions of the tissue 222. For example, some of the transducers 220 may be used to ablate a pattern around the bodily openings, ports or pulmonary vein ostia, for instance to reduce or eliminate the occurrence of atrial fibrillation.

Figure 3A:
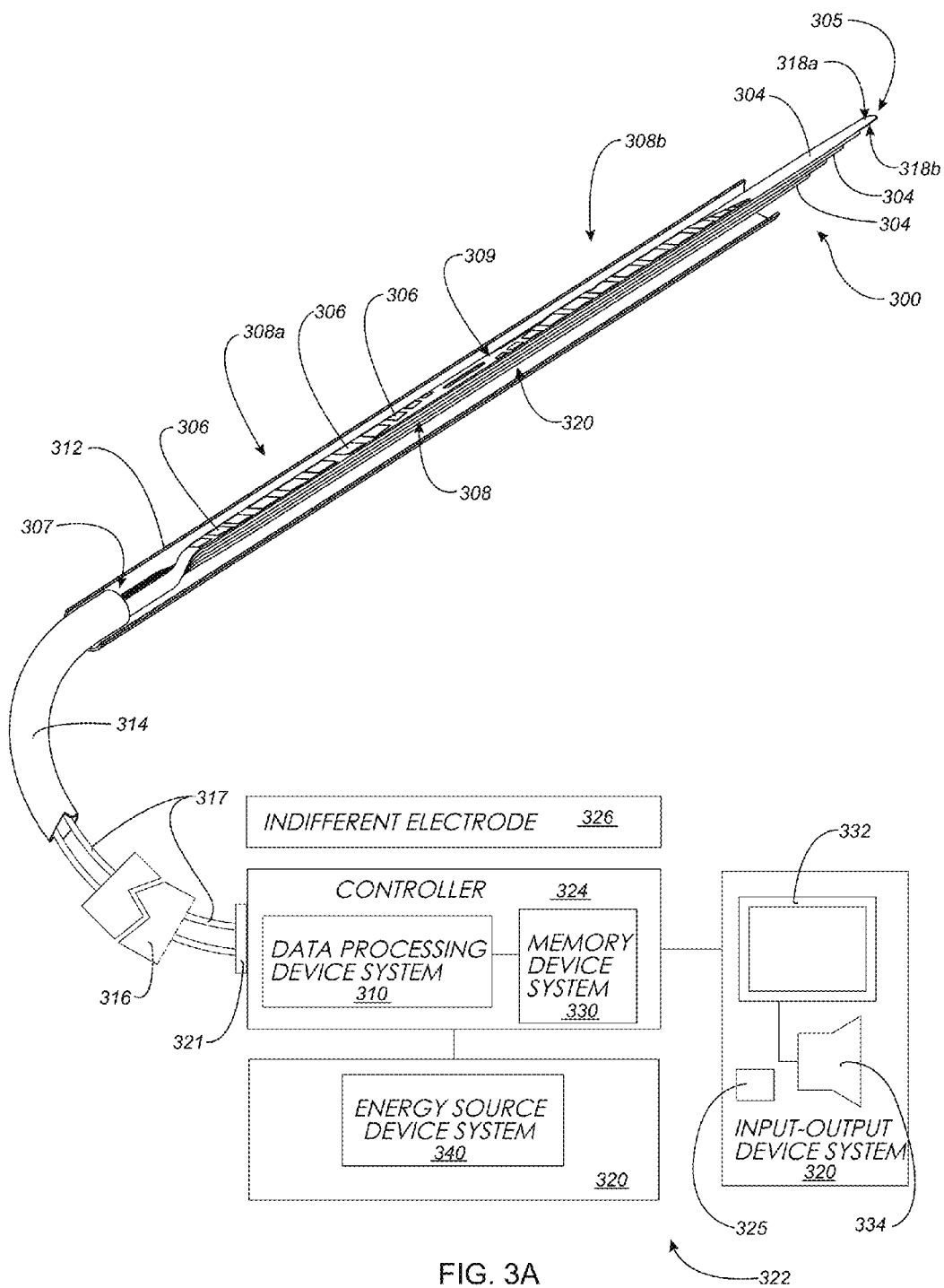
FIG. 3A illustrates a partially schematic representation of a medical system according to various example embodiments, the medical system including a data processing device system, an input-output device system, a memory device system, and a transducer-based device having a plurality of transducers and an expandable structure shown in a delivery or unexpanded configuration.
Figure 3B:
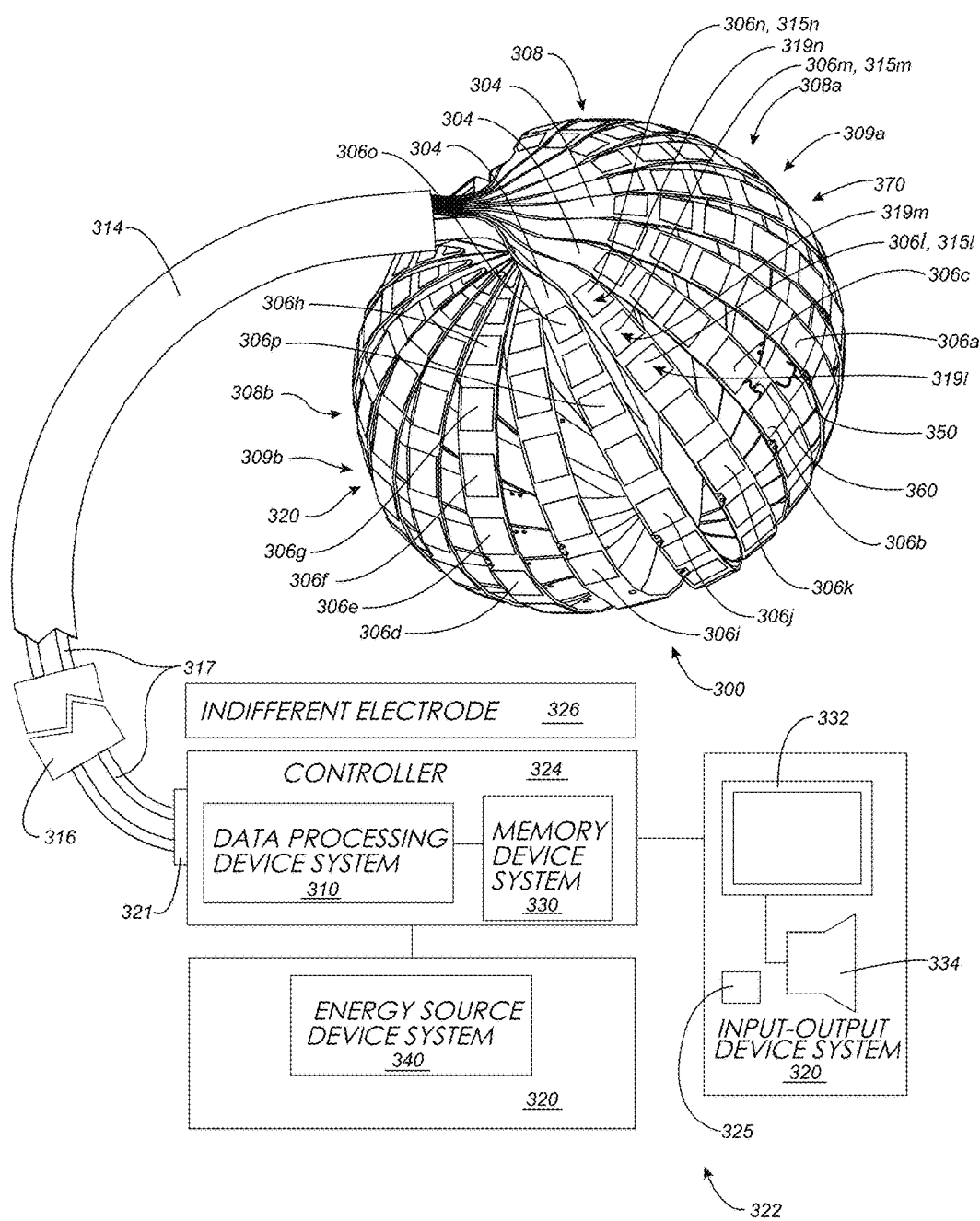
FIG. 3B illustrates the representation of the medical system of FIG. 3A with the expandable structure shown in a deployed or expanded configuration.

FIGS. 3A and 3B show a transducer-based device system (e.g., a portion thereof shown schematically) that includes a transducer-based device 300 according to one illustrated embodiment. Transducer-based device 300 includes a plurality of elongate members 304 (three called out in each of FIGS. 3A and 3B) and a plurality of transducers 306 (three called out in FIG. 3A and three called out in FIG. 3B as 306a, 306b and 306c). As will become apparent, the plurality of transducers 306 are positionable within a bodily cavity. For example, in some embodiments, the transducers 306 are able to be positioned in a bodily cavity by movement into, within, or into and within the bodily cavity, with or without a change in a configuration of the plurality of transducers 306. In some embodiments, the plurality of transducers 306 are arranged to form a two- or three-dimensional distribution, grid or array of the transducers capable of mapping, ablating or stimulating an inside surface of a bodily cavity or lumen without requiring mechanical scanning. As shown, for example, in FIG. 3A, the plurality of transducers 306 are arranged in a distribution receivable in a bodily cavity (not shown).

The elongate members 304 are arranged in a frame or structure 308 that is selectively movable between an unexpanded or delivery configuration (e.g., as shown in FIG. 3A) and an expanded or deployed configuration (i.e., as shown in FIG. 3B) that may be used to position elongate members 304 against a tissue surface within the bodily cavity or position the elongate members 304 in the vicinity of the tissue surface. In this embodiment, structure 308 has a size in the unexpanded or delivery configuration suitable for delivery through a bodily opening (e.g., via catheter sheath 312) to the bodily cavity. In this embodiment, structure 308 has a size in the expanded or deployed configuration too large for delivery through a bodily opening (e.g., via catheter sheath 312) to the bodily cavity. The elongate members 304 may form part of a flexible circuit structure (e.g., also known as a flexible printed circuit board (PCB) circuit). The elongate members 304 can include a plurality of different material layers. Each of the elongate members 304 can include a plurality of different material layers. The structure 308 can include a shape memory material, for instance Nitinol. The structure 308 can include a metallic material, for instance stainless steel, or non-metallic material, for instance polyimide, or both a metallic and non-metallic material by way of non-limiting example. The incorporation of a specific material into structure 308 may be motivated by various factors including the specific requirements of each of the unexpanded or delivery configuration and expanded or deployed configuration, the required position or orientation (e.g., pose), or both of structure 308 in the bodily cavity or the requirements for successful ablation of a desired pattern.

Figure 4:
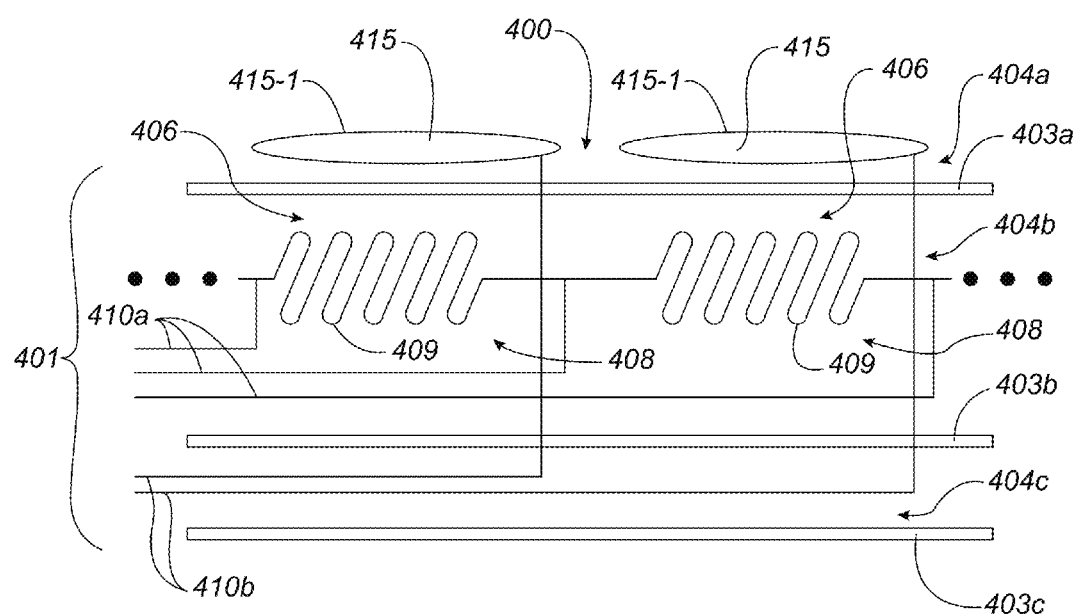
FIG. 4 illustrates a schematic representation of a transducer-based device that includes a flexible circuit structure according to various example embodiments.

FIG. 4 is a schematic side elevation view of at least a portion of a transducer-based device 400 that includes a flexible circuit structure 401 that is employed to provide a plurality of transducers 406 (two called out) according to an example embodiment. In some embodiments, the flexible circuit structure 401 may form part of a structure (e.g., structure 308) that is selectively movable between a delivery configuration sized for percutaneous delivery and expanded or deployed configurations sized too large for percutaneous delivery. In some embodiments, the flexible circuit structure 401 may be located on, or form at least part of, a structural component (e.g., elongate member 304) of a transducer-based device system.

The flexible circuit structure 401 can be formed by various techniques including flexible printed circuit techniques. In some embodiments, the flexible circuit structure 401 includes various layers including flexible layers 403a, 403b and 403c (i.e., collectively flexible layers 403). In some embodiments, each of flexible layers 403 includes an electrical insulator material (e.g., polyimide). One or more of the flexible layers 403 can include a different material than another of the flexible layers 403. In some embodiments, the flexible circuit structure 401 includes various electrically conductive layers 404a, 404b and 404c (collectively electrically conductive layers 404) that are interleaved with the flexible layers 403. In some embodiments, each of the electrically conductive layers 404 is patterned to form various electrically conductive elements. For example, electrically conductive layer 404a is patterned to form a respective electrode 415 of each of the transducers 406. Electrodes 415 have respective electrode edges 415-1 that form a periphery of an electrically conductive surface associated with the respective electrode 415.

Electrically conductive layer 404b is patterned, in some embodiments, to form respective temperature sensors 408 for each of the transducers 406 as well as various leads 410a arranged to provide electrical energy to the temperature sensors 408. In some embodiments, each temperature sensor 408 includes a patterned resistive member 409 (two called out) having a predetermined electrical resistance. In some embodiments, each resistive member 409 includes a metal having relatively high electrical conductivity characteristics (e.g., copper). In some embodiments, electrically conductive layer 404c is patterned to provide portions of various leads 410b arranged to provide an electrical communication path to electrodes 415. In some embodiments, leads 410b are arranged to pass though vias (not shown) in flexible layers 403a and 403b to connect with electrodes 415. Although FIG. 4 shows flexible layer 403c as being a bottom-most layer, some embodiments may include one or more additional layers underneath flexible layer 403c, such as one or more structural layers, such as a steel or composite layer. These one or more structural layers, in some embodiments, are part of the flexible circuit structure 401 and can be part of, e.g., elongate member 304. In addition, although FIG. 4 shows only three flexible layers 403a-403c and only three electrically conductive layers 404a-404c, it should be noted that other numbers of flexible layers, other numbers of electrically conductive layers, or both, can be included.

In some embodiments, electrodes 415 are employed to selectively deliver RF energy to various tissue structures within a bodily cavity (not shown) (e.g., an intra-cardiac cavity). The energy delivered to the tissue structures may be sufficient for ablating portions of the tissue structures. The energy delivered to the tissue may be delivered to cause monopolar tissue ablation, bipolar tissue ablation or blended monopolar-bipolar tissue ablation by way of non-limiting example. In some embodiments, each electrode 415 is employed to sense an electrical potential in the tissue proximate the electrode 415. In some embodiments, each electrode 415 is employed in the generation of an intra-cardiac electrogram. In some embodiments, each resistive member 409 is positioned adjacent a respective one of the electrodes 415. In some embodiments, each of the resistive members 409 is positioned in a stacked or layered array with a respective one of the electrodes 415 to form a respective one of the transducers 406. In some embodiments, the resistive members 409 are connected in series to allow electrical current to pass through all of the resistive members 409. In some embodiments, leads 410a are arranged to allow for a sampling of electrical voltage in between each resistive members 409. This arrangement allows for the electrical resistance of each resistive member 409 to be accurately measured. The ability to accurately measure the electrical resistance of each resistive member 409 may be motivated by various reasons including determining temperature values at locations at least proximate the resistive member 409 based at least on changes in the resistance caused by convective cooling effects (e.g., as provided by blood flow).

Referring to FIGS. 3A, 3B, transducer-based device 300 can communicate with, receive power from or be controlled by a transducer-activation system 322. In some embodiments, elongate members 304 can form a portion of an elongated cable 316 of control leads 317, for example by stacking multiple layers, and terminating at a connector 321 or other interface with transducer-activation system 322. The control leads 317 may correspond to the electrical connectors 216 in FIG. 2 in some embodiments. The transducer-activation device system 322 may include a controller 324 that includes a data processing device system 310 (e.g., from FIG. 1) and a memory device system 330 (e.g., from FIG. 1) that stores data and instructions that are executable by the data processing device system 310 to process information received from transducer-based device 300 or to control operation of transducer-based device 300, for example activating various selected transducers 306 to ablate tissue. Controller 324 may include one or more controllers.

Transducer-activation device system 322 includes an input-output device system 320 (e.g., from FIG. 1) communicatively connected to the data processing device system 310 (e.g., via controller 324 in this embodiment). Input-output device system 320 may include a user-activatable control that is responsive to a user action. Input-output device system 320 may include one or more user interfaces or input/output (I/O) devices, for example one or more display device systems 332, speaker device systems 334, keyboards, mice, joysticks, track pads, touch screens or other transducers to transfer information to, from, or both to and from a user, for example a care provider such as a physician or technician. For example, output from a mapping process may be displayed on a display device system 332. Input-output device system 320 may include a sensing device system 325 configured to detect various characteristics including, but not limited to, at least one of tissue characteristics (e.g., electrical characteristics such as tissue impedance, tissue type, tissue thickness) and thermal characteristics such as temperature. In this regard, the sensing device system 325 may include one, some, or all of the transducers 306 (or 406 of FIG. 4) of the transducer based device 300, including the internal components of such transducers shown in FIG. 4, such as the electrodes 315 and temperature sensors 408.

Transducer-activation device system 322 may also include an energy source device system 340 including one or more energy source devices connected to transducers 306. In this regard, although FIG. 3A shows a communicative connection between the energy source device system 340 and the controller 324 (and its data processing device system 310), the energy source device system 340 may also be connected to the transducers 306 via a communicative connection that is independent of the communicative connection with the controller 324 (and its data processing device system 310). For example, the energy source device system 340 may receive control signals via the communicative connection with the controller 324 (and its data processing device system 310), and, in response to such control signals, deliver energy to, receive energy from, or both deliver energy to and receive energy from one or more of the transducers 306 via a communicative connection with such transducers 306 (e.g., via one or more communication lines through catheter body 314, elongated cable 316 or catheter sheath 312) that does not pass through the controller 324. In this regard, the energy source device system 340 may provide results of its delivering energy to, receiving energy from, or both delivering energy to and receiving energy from one or more of the transducers 306 to the controller 324 (and its data processing device system 310) via the communicative connection between the energy source device system 340 and the controller 324.

In any event, the number of energy source devices in the energy source device system 340 is fewer than the number of transducers in some embodiments. The energy source device system 340 may, for example, be connected to various selected transducers 306 to selectively provide energy in the form of electrical current or power (e.g., RF energy), light or low temperature fluid to the various selected transducers 306 to cause ablation of tissue. The energy source device system 340 may, for example, selectively provide energy in the form of electrical current to various selected transducers 306 and measure a temperature characteristic, an electrical characteristic, or both at a respective location at least proximate each of the various transducers 306. The energy source device system 340 may include as its energy source devices various electrical current sources or electrical power sources. In some embodiments, an indifferent electrode 326 is provided to receive at least a portion of the energy transmitted by at least some of the transducers 306. Consequently, although not shown in FIG. 3A, the indifferent electrode 326 may be communicatively connected to the energy source device system 340 via one or more communication lines in some embodiments. In addition, although shown separately in FIG. 3A, indifferent electrode 326 may be considered part of the energy source device system 340 in some embodiments.

It is understood that input-output device system 320 may include other systems. In some embodiments, input-output device system 320 may optionally include energy source device system 340, transducer-based device 300 or both energy source device system 340 and transducer-based device 300 by way of non-limiting example. Input-output device system 320 may include the memory device system 330 in some embodiments.

Structure 308 can be delivered and retrieved via a catheter member, for example a catheter sheath 312. In some embodiments, a structure provides expansion and contraction capabilities for a portion of the medical device (e.g., an arrangement, distribution or array of transducers 306). The transducers 306 can form part of, be positioned or located on, mounted or otherwise carried on the structure and the structure may be configurable to be appropriately sized to slide within catheter sheath 312 in order to be deployed percutaneously or intravascularly. FIG. 3A shows one embodiment of such a structure. In this example embodiment, each of the elongate members 304 includes a respective distal end 305 (only one called out), a respective proximal end 307 (only one called out) and an intermediate portion 309 (only one called out) positioned between the proximal end 307 and the distal end 305. The respective intermediate portion 309 of each elongate member 304 includes a first or front surface 318a that is positionable to face an interior tissue surface within a bodily cavity (not shown) and a second or back surface 318b opposite across a thickness of the intermediate portion 309 from the front surface 318a. In some embodiments, each of the elongate members 304 is arranged front surface 318a-toward-back surface 318b in a stacked array during an unexpanded or delivery configuration similar to that described in co-assigned International Application No.: PCT/US2012/022061 and co-assigned International Application No.: PCT/US2012/022062, both of which are hereby incorporated herein by reference in their entirety. In many cases a stacked array allows the structure 308 to have a suitable size for percutaneous or intravascular delivery. In this embodiment, the elongate members 304 are arranged to be introduced into a bodily cavity (again not shown) distal end 305 first. For clarity, not all of the elongate members 304 of structure 308 are shown in FIG. 3A. A flexible catheter body 314 is used to deliver structure 308 through catheter sheath 312.

In a manner similar to that described in co-assigned International Application No.: PCT/US2012/022061 and co-assigned International Application No.: PCT/US2012/022062, each of the elongate members 304 is arranged in a fanned arrangement 370 in FIG. 3B. In this embodiment, the fanned arrangement 370 is formed during the expanded or deployed configuration in which structure 308 is manipulated to have a size too large for percutaneous or intravascular delivery. In this example embodiment, structure 308 includes a proximal portion 308a having a first domed shape 309a and a distal portion 308b having a second domed shape 309b. In this example embodiment, the proximal and the distal portions 308a, 308b include respective portions of elongate members 304. In this example embodiment, the structure 308 is arranged to be delivered distal portion 308b first into a bodily cavity (again not shown) when the structure is in the unexpanded or delivery configuration as shown in FIG. 3A. In this example embodiment, the proximal and the distal portions 308a, 308b are arranged in a clam shell configuration in the expanded or deployed configuration shown in FIG. 3B.

The transducers 306 can be arranged in various distributions or arrangements in various embodiments. In this example embodiment, various ones of the transducers 306 are spaced apart from one another in a spaced apart distribution in the delivery configuration shown in FIG. 3A. In this example embodiment, various ones of the transducers 306 are arranged in a spaced apart distribution in the deployed configuration shown in FIG. 3B. In this example embodiment, various pairs of transducers 306 are spaced apart with respect to one another. In this example embodiment, various regions of space are located between various pairs of the transducers 306. For example, in FIG. 3B the transducer-based device 300 includes at least a first transducer 306a, a second transducer 306b and a third transducer 306c (all collectively referred to as transducers 306). In this example embodiment each of the first, the second and the third transducers 306a, 306b and 306c are adjacent transducers in the spaced apart distribution. In this example embodiment, the first and the second transducers 306a, 306b are located on different elongate members 304 while the second and the third transducers 306b, 306c are located on a same elongate member 304. In this example embodiment, a first region of space 350 is between the first and the second transducers 306a, 306b. In this example embodiment, the first region of space 350 is not associated with any physical portion of structure 308. In this example embodiment, a second region of space 360 associated with a physical portion of device 300 (e.g., a portion of an elongate member 304) is between the second and the third transducers 306b, 306c. In this example embodiment, each of the first and the second regions of space 350, 360 does not include a transducer of transducer-based device 300. In this example embodiment, each of the first and the second regions of space 350, 360 does not include any transducer. It is noted that other embodiments need not employ a group of elongate members 304 as employed in the illustrated embodiment. For example, other embodiments may employ a structure having a one or more surfaces, at least a portion of the one or more surfaces defining one or more openings in the structure. In these embodiments, a region of space not associated with any physical portion of the structure may extend over at least part of an opening of the one or more openings. In other example embodiments, other structures may be employed to support or carry transducers of a transducer-based device such as a transducer-based catheter. For example, an elongated catheter member may be used to distribute the transducers in a linear or curvilinear array. Basket catheters or balloon catheters may be used to distribute the transducers in a two-dimensional or three-dimensional array.

Figure 7A:
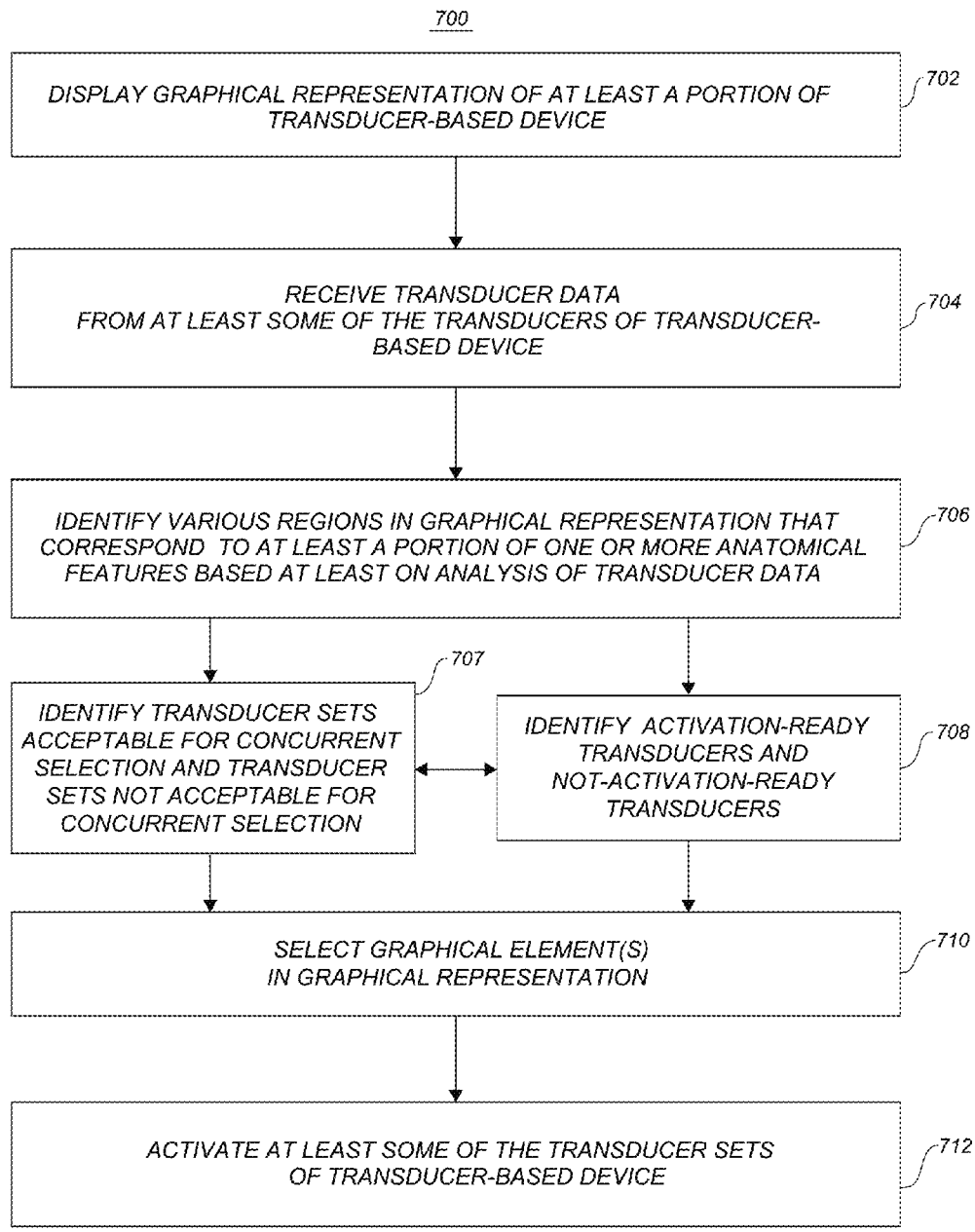
FIG. 7A illustrates a block diagram of a method for activating transducers of a transducer-based device according to some example embodiments.

FIG. 7A is a block diagram of a method 700 employed according to some example embodiments. In various example embodiments, a memory device system (e.g., memory device systems 130, 330) is communicatively connected to a data processing device system (e.g., data processing device systems 110 or 310) and stores a program executable by the data processing device system to cause the data processing device system to execute method 700 via interaction with at least, for example, a transducer-based device (e.g., transducer-based devices 200, 300, or 400). In these various embodiments, the program may include instructions configured to perform, or cause to be performed, various ones of the instructions associated with method 700. In some embodiments, method 700 may include a subset of the associated blocks or additional blocks than those shown in FIG. 7A. In some embodiments, method 700 may include a different sequence between various ones of the associated blocks than those shown in FIG. 7A.

Figure 5A:
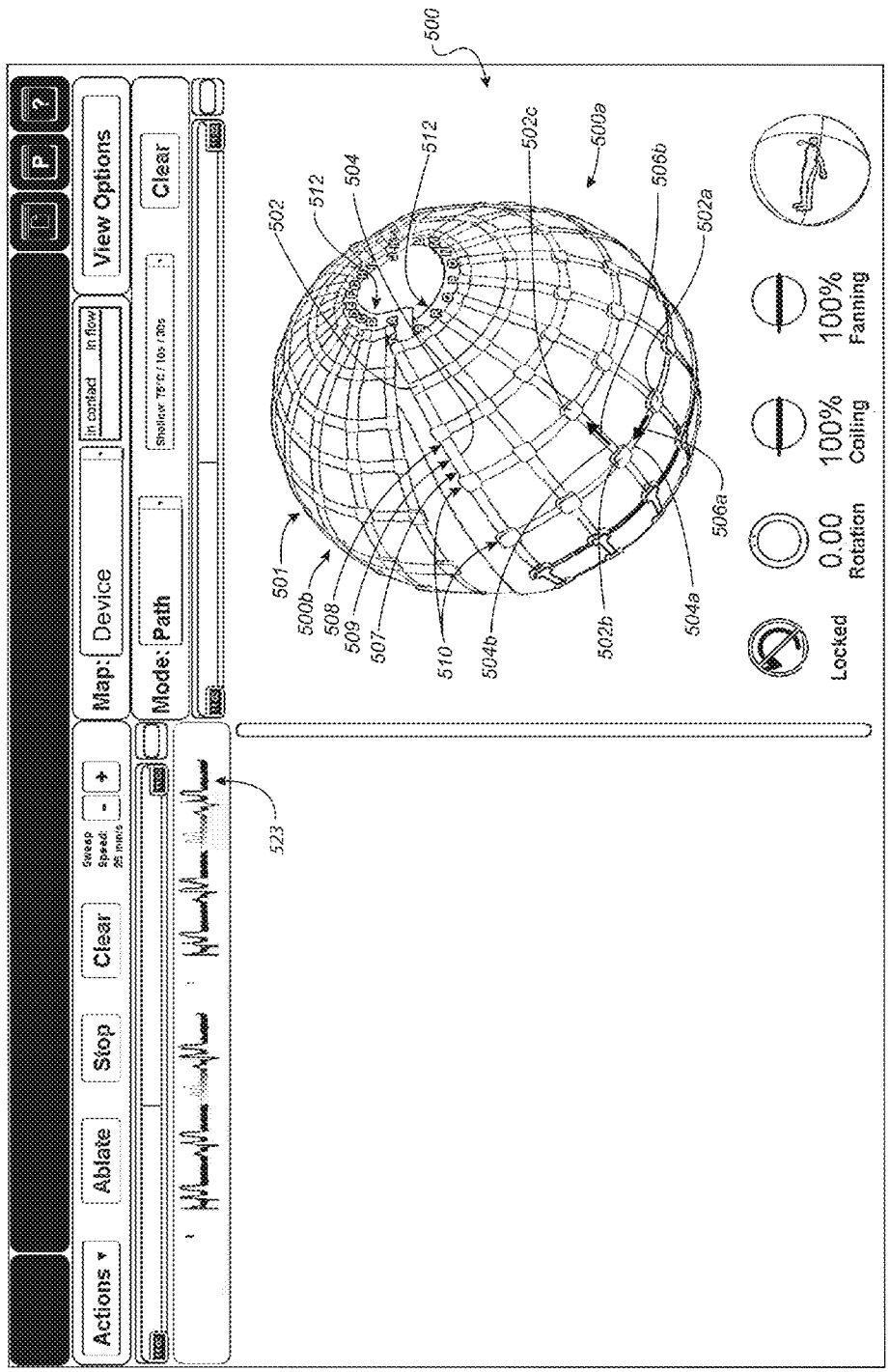
FIG. 5A illustrates a graphical interface providing a graphical representation of at least a portion of a transducer-based device according to various example embodiments, the graphical representation including a plurality of graphical elements including a plurality of transducer graphical elements and a plurality of between graphical elements.

Block 702 includes instructions (e.g., graphical representation instructions or graphical interface instructions provided by a program) configured to cause an input-output device system (e.g., input-output device system 120 or 320) to display a graphical representation of at least a portion of a transducer-based device. For example, FIG. 5A illustrates a graphical interface including a graphical representation 500 provided by the input-output device system according to one example embodiment provided in accordance with block 702. In this embodiment, the transducer-based device is a catheter-based device similar to devices 200 and 300 shown respectively in FIGS. 2 and 3. In this example embodiment, the graphical interface depicts graphical representation 500 of the transducer-based device as including a first domed portion 500a associated with a first domed portion of the transducer-based device (e.g., proximal portion 308a when having the first domed shape 309a) and a second domed portion 500b associated with a second domed portion of the transducer-based device (e.g., distal portion 308b having the second domed shape 309b). Various other transducer-based devices may be depicted in other embodiments. FIGS. 5A, 5B, 5C, 5D, 5E, 5F, 5G, 5H, 5I, 5J, and 5K (collectively FIG. 5) are presented in this disclosure in association with various different embodiments. It is understood that each of the different embodiments need not be associated with all of the FIG. 5, and in some cases will only be associated with a subset of the FIG. 5.

In this embodiment, the graphical representation 500 includes a plurality of graphical elements 501. Each of the graphical elements 501 is respectively associated with a respective one of a plurality of transducer sets. Each respective transducer set includes at least one of a plurality of transducers included as part of the transducer-based device (e.g., transducer-based devices 200, 300, or 400) and each respective transducer set has at least one different transducer than another of the other transducer sets. In this particular embodiment, each respective transducer set has at least one different transducer than each of the others of the other transducer sets.

In this example embodiment, each of at least some of the graphical elements 501 are provided by a respective one of a plurality of transducer graphical elements 502 that include at least a first transducer graphical element 502a, a second transducer graphical element 502b, and a third transducer graphical element 502c (e.g., all the transducer graphical elements collectively referred to as transducer graphical elements 502). In this example embodiment, each transducer graphical element 502 is associated with a single respective transducer of the transducer-based device. In some example embodiments, each transducer graphical element 502 is representative of a respective transducer of the transducer-based device. In some example embodiments, each transducer graphical element 502 is representative of a location or position of a respective transducer of the transducer-based device. In this example embodiment, the graphical representation 500 includes a first spatial relationship or arrangement between the displayed transducer graphical elements 502 that is consistent with a second spatial relationship or arrangement between the corresponding transducers associated with the transducer graphical elements 502. An electrocardiogram (ECG/EKG) signal 523 is also shown in the graphical interface of FIG. 5A.

In this example embodiment, each of at least some of the graphical elements 501 are provided by a respective one of a plurality of between graphical elements 504 including a first between graphical element 504a and a second between graphical element 504b (e.g., all the between graphical elements collectively referred to as between graphical elements 504). In various embodiments, each of the between graphical elements 504 is associated with a set of at least two of the transducers of the transducer-based device. In some example embodiments, each of the between graphical elements 504 is associated with a pair of transducers in the transducer-based device. In some example embodiments, each between graphical element 504 is associated with a region of space between a respective pair of transducers in the transducer-based device. In some example embodiments, each between graphical element 504 is associated with a region of space between a respective pair of adjacent ones of the transducers in the transducer-based device. In some embodiments, the region of space associated does not include any transducer. In some embodiments, each of one or more of the between graphical elements 504 is associated with a region of space (e.g., region of space 350) that is not associated with any physical part of the transducer-based device.

In this example embodiment, first transducer graphical element 502a is associated with a first transducer (e.g., first transducer 306a) of the transducer-based device, second transducer graphical element 502b associated with a second transducer (e.g., second transducer 306b) of the transducer-based device, and third transducer graphical element 502c associated with a third transducer (e.g., third transducer 306c) of the transducer-based device. In this example embodiment, the first between graphical element 504a is associated with a first region of space that is between the first and the second transducers and the second between graphical element 504b is associated with a second region of space that is between the second and the third transducers. In this illustrated embodiment, the first region of space is a region of space that is not associated with any physical part of the transducer-based device (e.g., first region of space 350) and the second region of space is a region of space that is associated with a physical part of the transducer-based device (e.g., second region of space 360). In this example embodiment, each of the first and the second between graphical elements 504a, 504b is associated with a region of space that does not include a transducer of the transducer-based device. In this example embodiment, each of the first and the second between graphical elements 504a, 504b is associated with a region of space that does not include any transducer. It is understood that a "region of space" need not be a vacant space but can include physical matter therein.

In this example embodiment, the second transducer graphical element 502b is depicted in a first direction (e.g., represented by arrow 506a) from the first transducer graphical element 502a, and the first between graphical element 504a is positioned between the second and the first transducer graphical elements 502b, 502a in the graphical representation. In this example embodiment, the third transducer graphical element 502c is depicted in a second direction (e.g., represented by arrow 506b) from the second transducer graphical element 502b, and the second between graphical element 504b is positioned between the second and the third transducer graphical elements 502b, 502c. In this example embodiment, the first and the second directions are non-parallel to each other. In this example embodiment, the first between graphical element 504a is formed, at least in part, at a location in the graphical representation intersected by the first direction from the first graphical transducer element 502a and the second between graphical element 504b is formed, at least in part at a location in the graphical representation intersected by the second direction from the second transducer graphical element 502b. In other example embodiments, other spatial relationships exist between the transducer graphical elements 502 and the between graphical elements 504 in the graphical representation. It is understood that arrows 506a, 506b do not form part of the graphical representation in this embodiment.

Figure 6:
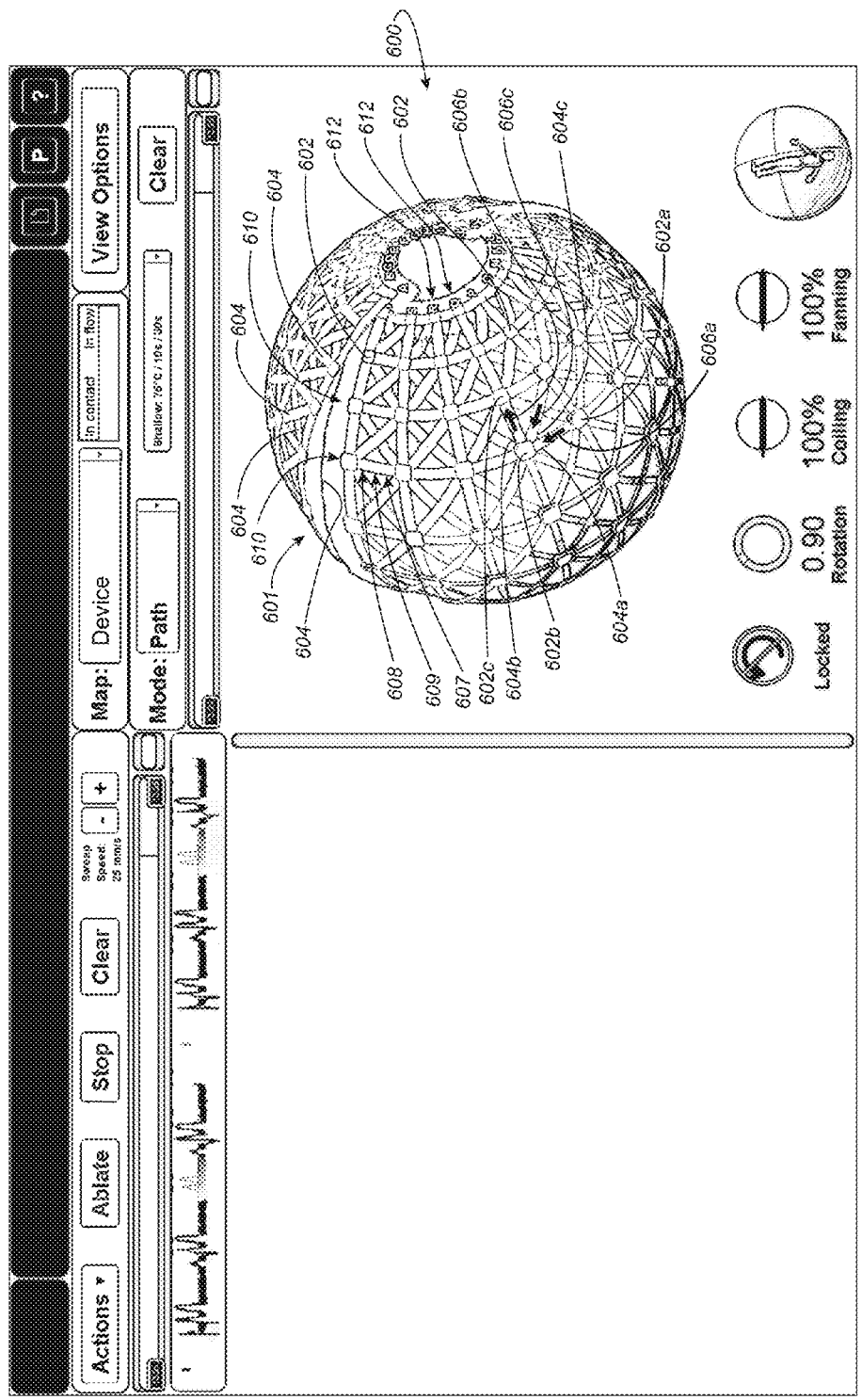
FIG. 6 illustrates a graphical interface providing a graphical representation of at least a portion of a transducer-based device according to various example embodiments.

In this example embodiment, each of the between graphical elements 504 includes a first end 507 (only one called out), a second end 508 (only one called out) and an elongate portion 509 (only one called out) extending between the first and the second ends 507, 508. The transducer graphical elements 502, the between graphical elements 504, or both may have different sizes, shapes or forms than those shown in the illustrated embodiment. In some embodiments, different ones of the transducer graphical elements 502 may be depicted with different shapes, sizes or forms in the graphical representation. In some embodiments, different ones of the between graphical elements 504 may be depicted with different shapes, sizes or forms in the graphical representation. In this embodiment, the respective elongate portion 509 of the first between graphical element 504a is depicted extending along the first direction (e.g., again represented by arrow 506a) and the respective elongate portion 509 of the second between graphical element 504b is depicted extending along the second direction (e.g., again represented by arrow 506b). In this example embodiment the first direction is depicted generally orthogonal to the second direction in the three-dimensional graphical representation. Other orientations between the first and the second direction are possible in other embodiments. For example, FIG. 6 illustrates a graphical interface including a graphical representation 600 provided by an input-output device system (e.g., input-output device system 120 or 320) according to another example embodiment. In a manner similar to FIG. 5A, the graphical interface of FIG. 6 provides a graphical representation 600 that includes a plurality of graphical elements 601, each of the graphical elements 601 associated with a respective one of a plurality of transducer sets. Each respective transducer set includes at least one of a plurality of the transducers included as part of the transducer-based device and each respective transducer set has at least one different transducer than another of the other transducer sets. In this particular embodiment, each respective transducer set has at least one different transducer than each of the others of the other transducer sets.

In a manner similar to the embodiment of FIG. 5A, the plurality of graphical elements 601 include a plurality of transducer graphical elements 602 (e.g., including transducer graphical elements 602*a*, 602*b* and 602*c*) and a plurality of between graphical elements 604. In a manner similar to the embodiment of FIG. 5A, each of the transducer graphical elements 602 is associated with a transducer of a transducer-based device and each of the between graphical elements 604 is associated with a region of space between a pair of transducers of a transducer based-device. In a manner similar to the embodiment of FIG. 5A, each of at least some of the between graphical elements (e.g., first between graphical element 604*a* and a third between graphical element 604*c*) is associated with a respective region of space that is not associated with any physical part of the transducer-based device. In a manner similar to the embodiment shown in FIG. 5A, each of at least some of the between graphical elements (e.g., second between graphical elements 604*b*) is associated with a respective region of space that is associated with a physical portion of the transducer-based device (e.g., an elongate member 304). In a manner similar to the embodiment shown in FIG. 5A, each of the between graphical elements 604 includes a first end 607 (only one called out), a second end 608 (only one called out) and an elongate portion 609 (only one called out) extending between the first and the second ends 607, 608. In this example embodiment, the respective elongate portion 609 of each of two of first ones of the between graphical element (e.g., between graphical elements 604*a*, 604*b*) is depicted extending along a respective first direction (e.g., represented by respective ones of arrows 606*a*, 606*b*), and the respective elongate portion 609 of a second one of the between graphical elements 604 (e.g., between graphical element 604*c*) is depicted extending along a second direction (e.g., represented by arrow 606*c*). In this example embodiment, the second direction is oblique to each of the first directions. In this example embodiment, the second direction forms an acute angle with respect to each of the first directions. In this illustrated embodiment, each between graphical element 604 is associated with a region of space that does not include a transducer of a transducer-based device. In this illustrated embodiment, each between graphical element 604 is associated with a region of space that does not include any transducer.

Referring back to FIG. 5A, at least a portion of the transducer graphical elements 502, and at least a portion of the between graphical elements 504 are arranged in a plurality of rows 510 (two called out) and a plurality of columns 512 (two called out, each column 512 identified in the graphical representation by a respective one of letters "A", "B", "C", "D", "E", "F", "G", "H", "I", "J", "K", "L", "M", "N", "O", "P", "Q", "R", "S", and "T"). In this regard, it may be considered that the transducers (e.g., 306 in FIGS. 3A, 3B) corresponding to the transducer graphical elements 502 are arranged in an arrayed distribution that includes a plurality of intersecting transducer rows and transducer columns, a respective group of the plurality of transducers arranged along each of the transducer rows, and a respective group of the plurality of transducers arranged along each of the transducer columns. Adjacent ones of the transducer columns may be separated from each other at least by a non-physical portion of the transducer-based system, e.g., corresponding to region of space 350 in FIG. 3B, and adjacent ones of the transducer rows may be separated from each other at least by a physical portion (e.g., a portion between transducers 306 along a same elongate member 304) of the transducer-based system (e.g., 200, 300, or 400).

Referring back to FIG. 5A, a portion of each of the columns 512 may correspond to region of space associated with a physical portion of the transducer-based device (e.g., an elongate member 304). In this example embodiment, each of the columns 512 corresponds to at least a portion of the transducers located on a particular elongate member of a transducer-based device (e.g., an elongate member 304). In this example embodiment, each of the columns 512 corresponds to at least a portion of the transducers located on a respective one of a pair of domed portions 500*a*, 500*b* arranged in a clam shell configuration similar to the embodiments of FIG. 3B. In embodiments in which each domed portion is formed by a respective portion of each of a plurality of elongate members (e.g., elongate members 304), a set of two or more of the columns 512 may correspond to the transducers located on a single one of the elongate members.

In this example embodiment, a portion of each of the rows 510 corresponds to regions of space not associated with any physical portion of the transducer-based device (e.g., regions of space 350 between adjacent ones of the elongate members 304). In other example embodiments, different numbers of transducer graphical elements 502 and different numbers and spatial arrangements of between graphical elements 504 may be depicted in the graphical representation. In other example embodiments, different numbers and spatial arrangements of rows 510 and columns 512 may be depicted in the graphical representation. In various embodiments, each of the between graphical elements (e.g., between graphical elements 504, 604) depicted in the graphical representation are representative of a respective physical path extending between a respective pair of transducers of the transducer-based device. Each of the physical paths may extend over a physical surface of the transducer-based device or over a portion of an opening defined by a physical surface of the transducer-based device. In the embodiment shown in FIG. 6, each between graphical element 604 is representative of a respective physical path extending between the respective transducers associated with the adjacent pair of transducer graphical elements 602 that the between graphical element 604 extends between. In the embodiment shown in FIG. 6, each adjacent pair of the transducer graphical elements 602 may be provided along a row 610 (two called out) of the graphical elements 601, along a column 612 (two called out) of the graphical elements 601, or diagonally between a row 610 and a column 612.

Referring back to FIG. 5A, the transducer graphical elements 502 and the between graphical elements 504 in each respective one of the rows 510 are interleaved with respect to one another along the respective one of the rows 510. In this illustrated embodiment, the transducer graphical elements 502 and the between graphical elements 504 in each respective one of the columns 512 are interleaved with respect to one another along the respective one of the columns 512. In this illustrated embodiment, each one of the plurality of columns 512 shares a same transducer graphical element 502 with one of the plurality of rows 510. In this illustrated embodiment, each respective one of the plurality of columns 512 excludes any of the between graphical elements 504 included in each of the plurality of rows 510. In this illustrated embodiment, at least a first one of the between graphical elements 504 (e.g., second between graphical element 504b) is depicted in the graphical representation between two adjacent ones of the plurality of rows 510 and at least a second one of the plurality of between graphical elements 504 (e.g., first between graphical element 504a) is positioned between two adjacent ones of the plurality of columns 512. In this example embodiment, the plurality of rows 510 and the plurality of columns 512 are depicted as a three-dimensional arrangement in the graphical representation. In this example embodiment, at least two of the plurality of columns 512 are depicted in the graphical representation extending along respective directions that converge with respect to one another. In this illustrated embodiment, at least two of the plurality of columns 512 are depicted in the graphical representation extending along non-parallel directions and at least two of the plurality of rows 510 are depicted extending along parallel directions. In this illustrated embodiment, the rows 510 and the columns 512 are depicted in the graphical representation in an arrangement in which the columns 512 are circumferentially arranged. In this illustrated embodiment, the rows 510 and the columns 512 are depicted in the graphical representation in an arrangement having a generally spherical shape. The plurality of columns 512 may be depicted like lines of longitude, and the plurality of rows 510 may be depicted like lines of latitude.

In this illustrated embodiment, the respective first end 507 and the respective second end 508 of each of at least some of the plurality of between graphical elements 504 connects to a transducer graphical element 502 in the graphical representation. The transducer graphical elements 602 and a portion of the between graphical elements 604 in the embodiment of FIG. 6 are arranged in a similar manner to the embodiment shown in FIG. 5A. In the embodiment of FIG. 6, at least some of the between graphical elements 604 extend along respective directions that form acute angles with the respective directions extended along by others of the between graphical elements 604. In the embodiment of FIG. 6, at least some of the between graphical elements 604 extend along respective directions that form acute angles with the respective directions extended along by a row 610 or a column 612.

Figure 5B:
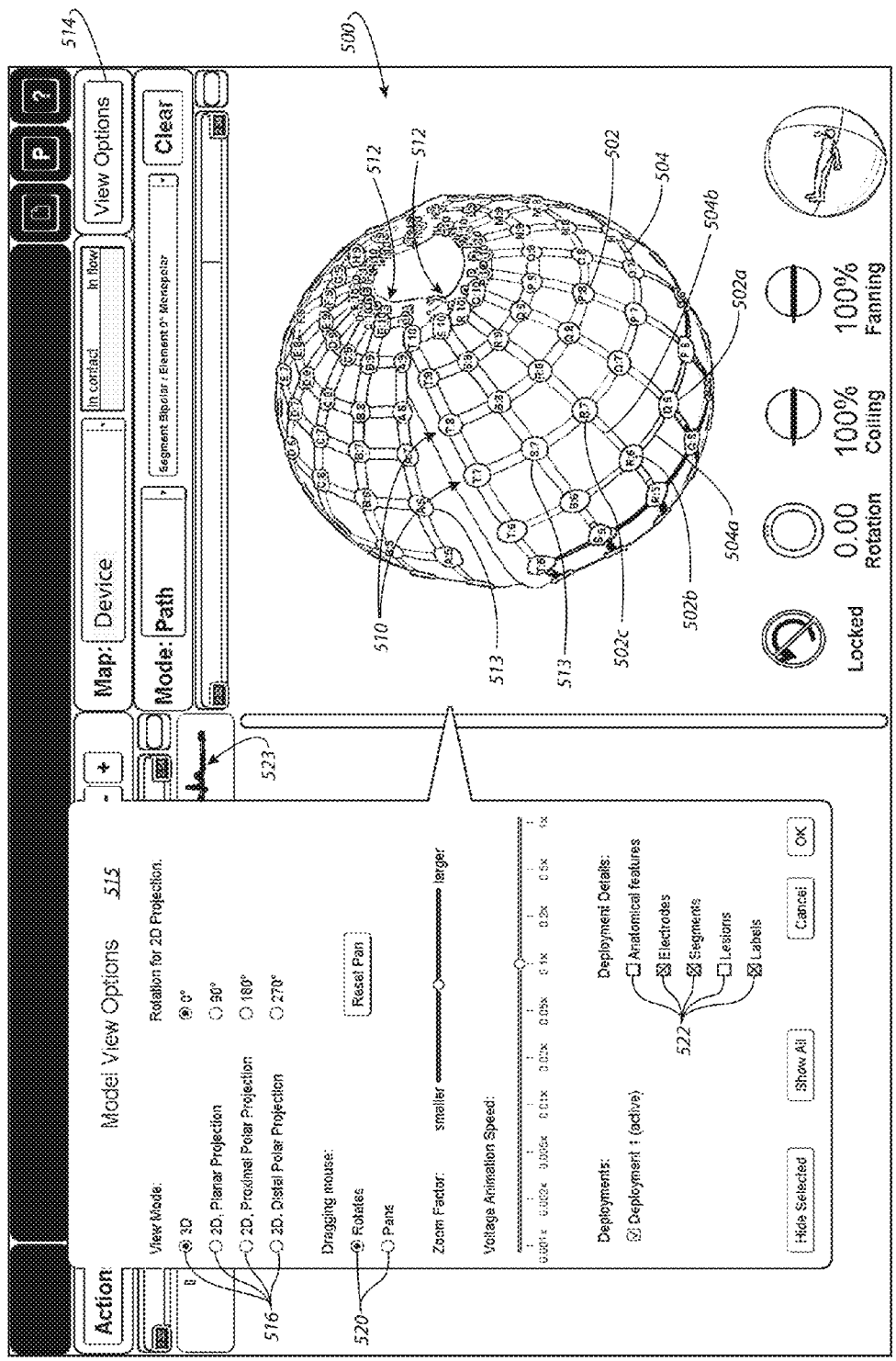
FIG. 5B illustrates the graphical representation provided by the graphical interface of FIG. 5A with at least some of the transducer graphical elements identified by identification labels.

The graphical interface of FIG. 5B includes the graphical representation 500 with the addition of identification labels 513 (two called out) to each of the transducer graphical elements 502. In this example embodiment identification labels are applied by operating the input-output device system to activate a control button 514 identified as "View Options". Selection, activation, or both selection and activation of a control button, a selection box or other graphical element provided in the various embodiments may be accomplished via various input-output device system controls that can include a touch screen, keyboard or computer mouse by way of non-limiting example. In various embodiments, selection of control button 514 causes the selection menu 515 identified as "Model View Options" to appear in the graphical representation. Selection menu 515 provides various selection boxes 516 that are selectable to vary the graphical representation of the portion of the transducer-based device between a three-dimensional representation (e.g., as depicted in FIGS. 5A and 5B) and a two dimensional representation (e.g., as depicted in FIG. 5D). Various two-dimensional representations are possible in various embodiments. For example, the two-dimensional representation depicted in FIG. 5D is shown in a "Mercator-type" representation in which the first domed portion 500a (e.g., shown in FIG. 5A) of the depicted transducer-based device is depicted as first Mercator projection 518a and the second domed portion 500b (e.g., shown in FIG. 5A) of the depicted transducer-based device is a depicted as a second Mercator projection 518b. The first and the second Mercator projections 518a and 518b advantageously allow for simultaneous viewing of all the transducer graphical elements 502 and the between graphical elements 504. Other two-dimensional representations including polar projections are also selectable.

Selection menu 515 provides various selection boxes 520 that can control mouse drag functions between rotating and panning modes. A rotating mode may be advantageously used for manipulation of a three-dimensional representation of the transducer-based device to allow for viewing a portion of the three-dimensional representation that was not previously viewable. Selection menu 515 includes a plurality of selection boxes 522 that allow for variations in the viewable content of the graphical representation. In this embodiment, a selection box 522 allows for the selective inclusion in the graphical representation of graphical elements associated with various anatomical features. In some example embodiments, the graphical elements associated with the anatomical features are selectable from a menu and may be tailored to a particular procedure in which the transducer-based device is employed. Various ones of the selection boxes 522 allow for selective inclusions of the transducer graphical elements 502 (e.g., indicated as "Electrodes" in this illustrated embodiment) and the selective inclusion of the between graphical elements 504 (e.g., indicated as "Segments" in this illustrated embodiment). In this embodiment, a selection box 522 allows for the selective inclusion in the graphical representation of graphical elements associated with lesions which may be of particular interest in embodiments in which various transducers of the transducer based-device ablate tissue to form the lesions therein.

In this example embodiment, a selection box 522 allows for the selective inclusion of identification labels 513 (e.g., indicated as "Labels" in this illustrated embodiment). In this example embodiment, each of the identification labels 513 is employs an alpha-numeric format including a letter representative of the column 512 in which a corresponding transducer graphical element is located and a number representative of a location of the transducer graphical element 502 in the corresponding column 514. Other identification schemes may be employed in other embodiments.

Having described examples of the graphical representation displayed according to the instructions of block 702 in FIG. 7A, the selection of one or more graphical elements in the graphical representation according to some embodiments will now be described with respect to block 710 in FIG. 7A. Accordingly, although FIG. 7A shows block 710 located after blocks 707 and 708, the invention is not limited to this arrangement, and the selection of one or more graphical elements according to block 710 can occur at any time the graphical elements are selectable, such as when they are displayed in the graphical representation displayed according to block 702. Blocks 704, 706, 707, and 708 in FIG. 7A are described afterwards.

In this regard, the selection according to the instructions of block 710 includes, in some embodiments, multiple constituent or sub-selections (although in other embodiments, the selection according to the instructions of block 710 includes only a single selection). For instance, in some embodiments, block 710 includes selection instructions configured to cause, due to execution of the selection instructions by the data processing device system (e.g., exemplified by data processing device systems 110 or 310), selection of a graphical element. In some embodiments, such selection instructions include a first group of instructions configured to cause the data processing device system to receive or process, via the input-output device system, a user instruction to select a graphical element. In some of these embodiments, such selection instructions also include a second group of instructions configured to cause the data processing device system to perform its own selection of the graphical element in response to receiving the user instruction. For instance, the user instruction to select the graphical element might originate from a user clicking a mouse button (e.g., a first constituent selection) while a cursor is above a user-selected graphical element. In this case, the first group of instructions could configure the data processing device system to recognize this user instruction when it is received via the data input-output device system as a user instruction to select the user-selected graphical element below the cursor at the time of the mouse-button click. In some embodiments, the second group of instructions may configure the data processing device system, in response to the first group of instructions recognizing this user instruction, to perform its own selection (e.g., a second constituent selection) of the user-selected graphical element at least by causing, via the input output device system, the display of the user-selected graphical element to change one or more visual characteristics of the user-selected graphical element. Accordingly, the selection according to the instructions of block 710 may be deemed, in some embodiments, to involve a first, user-based constituent selection and a second, machine-based or automatic constituent selection triggered by the user-based constituent selection.

Although a mouse-click was provided above as an example of a user-based constituent selection, and the changing of a visual characteristic of the user-selected graphical element was provided as an example of a machine-based constituent selection, it should be noted, however, that any form of user-based selection or machine-based selection of a graphical element known in the art can be used. In this regard, direct interaction with a graphical element itself (e.g., by way of a mouse click on the graphical element) is not required to directly select the graphical element or its corresponding transducer. For example, a user might type a unique identifier associated with a graphical element or transducer via a keyboard, which can cause direct selection of that graphical element or transducer.

Further, although a user-based constituent selection of a user-selected graphical element followed by a machine-based constituent selection of that user-selected graphical element was provided above as an example of constituent selections involved with block 710, it should be noted that a user-based constituent selection of a first user-selected graphical element can also cause a machine-based constituent selection of a second, different, non-user-selected graphical element. For example, a user-performed mouse-click while the mouse cursor is above a user-selected between-graphical element 504 (e.g., a user-based constituent selection) can cause, possibly among other things, a machine-based constituent selection of the non-user-selected transducer graphical elements 502 at each end of the user-selected between graphical element 504. In this regard, the phrase, "user-selected", when used herein to describe a selected graphical element (e.g., a transducer graphical element or a between graphical element), is intended to refer to a graphical element directly selected by a user, as opposed to a non-user-selected graphical element, which is a machine-selected graphical element that is machine-selected either in response to no user instruction to select any graphical element or in response to a user-instruction to select a user-selected graphical element different than the machine-selected graphical element. In cases where a user selection of a user-selected graphical element causes a machine-selection of a different graphical element, it can be said that the different graphical element is indirectly selected by the user.

Further still, although a user-based constituent selection followed by a machine-based constituent selection was provided above as an example of constituent selections involved with block 710, it should be noted that any number of constituent selections, whether user-based or machine-based, can be involved with block 710. For example, depending upon how the user-interface is structured, one or more user-based constituent selections may result in one or more machine-based constituent selections. For instance, multiple user gestures (e.g., a double-fingered gesture on a touch screen, a mouse click-drag-and-release sequence, or other multiple user-gesture technique) might be required to identify a particular user-selected graphical element in order to cause the data processing device system to change the visual characteristics of (or provide another form of selection of) the particular user-selected graphical element. For another example, multiple user-based constituent selections might be a mouse click-and-hold followed by a dragging of a cursor to expand a selection box originating from the initial mouse click location, followed by a releasing of the mouse button to define the final size of the selection box. This initial user-based selection (comprised of the multiple user-based constituent selections) could be recognized by the data processing device system according to the above-discussed first group of instructions, and cause multiple machine-based or automatic constituent selections performed by the data processing device system according to the above-discussed second group of instructions. For instance, these multiple machine-based or automatic constituent selections could include a first constituent selection by the data processing device system of all graphical elements residing within the selection box, followed by a second constituent selection of only those graphical elements deemed to reside within the selection box whose corresponding transducers have been deemed acceptable for concurrent selection (see, e.g., the discussions below regarding block 707 in FIG. 7A, as well as the discussions below regarding FIG. 7B) or activation (see, e.g., the discussions below regarding block 708 in FIG. 7A and block 804 in FIG. 8).

Further still, although one or more user-based constituent selections followed by one or more machine-based constituent selections was provided above as an example of constituent selections involved with block 710, it should be noted that block 710 might not involve any user-based constituent selections. For example, graphical element selection according to block 710 might occur based upon data received from transducers, and this data might result in one or more machine-based or automatic constituent selections performed by the data processing device system.

It should be noted that, whenever a selection of a graphical element is discussed herein, such selection, in some embodiments, can include the above-discussed constituent selections. However, the above-discussed constituent selections are not limited to just selections of graphical elements and can apply to any selection described herein. For example, one or more user-based constituent selections of a user-selected graphical element can lead to one or more machine-based constituent selections of the user-selected graphical element or some other graphical element(s), which can lead to one or more machine-based selections of one or more transducers corresponding to the machine-selected graphical elements, the machine-based selection(s) of the one or more transducers possibly causing an activation of the one or more transducers. For another example, one or more user-based constituent selections of a user-selected graphical element can lead to one or more machine-based constituent selections of one or more data objects associated with the user-selected graphical element, one or more other associated graphical elements, one or more transducers associated with the user-selected graphical element, or one or more other objects associated with the user-selected graphical element, such as for purposes of viewing or changing properties of the one or more data objects or causing an activation based upon information provided by the one or more data objects. It should also be noted that the above-discussion regarding block 710 and user and machine based selections and constituent selections may apply, in some embodiments, to block 710 in FIG. 7B, block 808 in FIG. 8, block 908 in FIG. 9, blocks 807 and 808 in FIG. 10, block 1102 in FIG. 12, block 1202 in FIG. 13, block 1302 in FIG. 14, block 1402 in FIG. 15A, block 1502 in FIG. 16, or any other selection-based discussions herein.

In view of the above-discussion regarding selection types involved with block 710, in some embodiments, the instructions of block 710 are provided in a program that includes instructions configured to cause the data processing device system to receive a selection from the input-output device system of a transducer graphical element (e.g., transducer graphical element 502 or 602).

The selection of one or more graphical elements according to instructions of block 710 in FIG. 7A may cause, in some embodiments, an activation of at least some transducer sets of a transducer-based device (e.g., 200, 300, or 400) according to instructions of block 712. In some embodiments, block 712 includes instructions configured to cause an activation of each of at least some of the transducer sets of the transducer-based device (e.g., again exemplified by transducer based devices 200, 300, or 400) in response to receiving a selection of a corresponding one of the graphical elements (e.g., graphical elements 501, 601) in accordance with selection instructions included in block 710.

In some embodiments, the program can include activation instructions (e.g., in accordance with block 712) configured to, in response to receiving the selection of a transducer graphical element (e.g., transducer graphical element 502, 602), cause, via the input-output device system, activation of the respective transducer of the transducer-based device corresponding to the selected transducer graphical element. In various embodiments, the instructions configured to activate the respective transducer corresponding to the selected transducer graphical element include instructions that are configured to cause energy from an energy source device system (e.g., energy source device system 340) to be delivered to the respective transducer. In some embodiments, a sensing device system (e.g., provided at least in part by a number of the transducers) is arranged to sense at least one tissue electrical characteristic (e.g., tissue impedance) at a respective location at least proximate the respective transducer corresponding to the selected transducer graphical element with the energy delivered to the transducer (e.g., in some embodiments, tissue impedance may be measured between transducers on the structure 308 or between a transducer on the structure 308 and the indifferent electrode 326). In some of these various embodiments, the energy is sufficient for ablating tissue (e.g., tissue-ablating energy). In some of these various embodiments, an indifferent electrode (e.g., indifferent electrode 326) is provided (e.g., usually to an external surface of a body) while the transducer-based device is received in a bodily cavity within the body. A portion of the tissue-ablating energy delivered to the respective transducer corresponding to the selected transducer graphical element may be transmitted from the respective transducer to the indifferent electrode in a process typically referred to as monopolar ablation. In some embodiments, the instructions of block 712 that are configured to activate the respective transducer corresponding to the selected transducer graphical element includes instructions that are configured to cause a sensing device system (e.g., sensing device system 325) to detect electrophysiological activity in an intra-cardiac cavity at a location at least proximate the respective transducer. The detected electrophysiological activity can be displayed as an electrogram via the input-output device system (e.g. electrograms 535 in various ones of FIG. 5). In some embodiments, detection of electrophysiological activity in an intra-cardiac cavity at a location at least proximate various ones of the transducers occurs continuously. Other forms of activation of the respective transducer corresponding to the selected transducer graphical element are possible in other embodiments. In some embodiments, activation of the respective transducer corresponding to the selected transducer graphical element under the influence of the instructions configured to activate the respective transducer is referred to as monopolar activation. Monopolar activation can include activation for monopolar ablation or monopolar electrogram generation by way of non-limiting example.

For another example, in some embodiments, the instructions of block 710 are provided in a program that includes selection instructions configured to cause, due to execution of the selection instructions by the data processing device system (e.g., again exemplified by data processing device systems 110 or 310), reception of a selection from the input-output device system of a between graphical element (e.g., between graphical elements 504 or 604). In accordance with the instructions of block 712 the program can include activation instructions configured to, in response to receiving the selection, cause activation, via the input-output device system, of a respective set of two or more of the transducers (e.g., a pair of the transducers in some embodiments) of the transducer-based device corresponding to the between graphical element.

Advantageously, activating a set of two or more of the transducers based on a selection of a single graphical element (e.g., between graphical element 504 or 604) provides for a workflow that is less cumbersome and more expeditious than individually selecting the respective graphical elements (e.g., transducer graphical elements 502 or 602) associated with each transducer of the set of two or more of the transducers, especially when 50, 100, 200 or even over 300 or more transducer graphical elements are provided in the graphical representation. This is even more advantageous, when a single graphical element (e.g., between graphical element 504 or 604) provides additional information (e.g., spatial information) relating each of the transducers in the set of two or more of the transducers. For example, a between graphical element 504 or 604 can indicate a distance between or acceptability-of-activation of transducers of a corresponding transducer pair, and, accordingly, the between graphical element 504 or 604 provides, in some embodiments, information about the corresponding pair of transducers and, thereby, makes the selection process more efficient. In addition, allowing selection of the between-graphical elements for corresponding transducer activation can provide a more intuitive user-interface in certain applications. For example, such an arrangement allows a user to make selections along an ablation path or a path along which data is to be obtained, without having to focus on the transducers required to make that ablation path or acquire that data. The user can, for example, just select a path using between graphical elements (e.g., user-based selection(s)/constituent selection(s)), and the corresponding transducers are automatically selected (e.g., machine-based selection(s)/constituent selection(s)) in response. Since various ones of the between graphical elements need not be tied to any physical portion of the transducer-based device, they can be freely designed to reflect the path (e.g., over tissue or fluid) in which their corresponding transducers will interact when activated (e.g., by causing ablation or gathering data). In this regard, if the between graphical elements are configured to accurately represent their respective path segments in which ablation or data gathering will occur, according to some embodiments, the user can gain an even better understanding of the expected results of activation of the corresponding transducers.

In some of the embodiments where the instructions according to block 712 are configured to cause a data processing device system to activate a respective set of two or more of the transducers, the instructions according to block 712 include instructions that are configured to cause energy from an energy source device system (e.g., energy source device system 340) to be delivered to the respective set of two or more of the transducers. In some embodiments, a sensing device system (e.g., sensing device system 325) is arranged to sense at least one tissue electrical characteristic (e.g., tissue impedance) at respective locations at least proximate each transducer of the respective set of two or more of the transducers with the energy delivered to the respective set of two or more of the transducers (e.g., in some embodiments, tissue impedance may be measured between transducers on the structure 308 or between a transducer on the structure 308 and the indifferent electrode 326). In some embodiments, (a) a portion of the energy delivered to a first transducer of the respective set of two or more of the transducers (e.g., first transducer 306a) is transmitted by the first transducer, (b) a portion of the energy delivered to a second transducer of the respective set of two or more of the transducers (e.g., second transducer 306b) is transmitted by the second transducer, or both (a) or (b). In some of embodiments, (a) a portion of the energy delivered to a first transducer of the respective set of two or more of the transducers (e.g., first transducer 306a) is transmitted by the first transducer to a second transducer of the respective set of two or more of the transducers (e.g., second transducer 306b), (b) a portion of the energy delivered to the second transducer of the respective set of two or more of the transducers is transmitted by the second transducer to the first transducer, or both (a) or (b). In some embodiments, the energy is sufficient for ablating tissue (e.g., tissue ablating energy). In some example embodiments, a selected between graphical element (e.g., between graphical elements 504 or 604) is representative of a physical path extending between a respective pair of the transducers associated with the selected between graphical element and the energy is sufficient for ablating a portion of tissue extending along the physical path. A portion of the tissue-ablating energy may be transmitted between the respective pair of the transducers in a process typically referred to as bipolar ablation. In some embodiments, an indifferent electrode (e.g., indifferent electrode 326) is provided (e.g., usually to an external surface of a body) while the transducer-based device is received in a bodily cavity within the body. Some of the tissue-ablating energy may be transmitted between the respective pair of the transducers while some of the tissue-ablating energy may be transmitted from various ones of the respective pair of the transducers to the indifferent electrode in a process typically referred to as blended monopolar-bipolar ablation. The term "bipolar ablation" as used in this disclosure is to be interpreted broadly to include blended monopolar-bipolar ablation in some embodiments.

In addition to embodiments where the instructions according to block 712 are configured to cause a data processing device system to cause bipolar ablation, the instructions according to block 712, in some embodiments, are configured to cause a data processing device system to cause multi-transducer monopolar ablation with the respective set of two or more of the transducers, e.g., dual monopolar ablation for two transducers, or triple monopolar ablation for three transducers. In such cases, for example, the respective set of two or more of the transducers may be 'queued' for monopolar ablation, such that monopolar ablation occurs for each transducer in the respective set of two or more of the transducers within some period of time, but not necessarily at the same time or even contiguously one right after another. However, in some embodiments, concurrent monopolar activation (e.g., ablation) may occur for the respective set of two or more of the transducers. In this regard, references herein to the occurrence of monopolar ablation for more than one transducer may include this multi-transducer monopolar ablation according to some embodiments. In addition, any reference herein to the occurrence of bipolar ablation may be replaced with the occurrence of dual monopolar ablation (or other multi-transducer monopolar ablation when more than two transducers are involved), according to some embodiments.

In some embodiments, the instructions, according to block 712, configured to activate the respective set of two or more of the transducers include instructions that are configured to cause a sensing device system to detect electrophysiological activity in an intra-cardiac cavity at each of respective locations at least proximate each of the transducers of the set. The detected electrophysiological activity detected at each of the respective locations can be displayed as an electrogram via the input-output device system (e.g., electrograms 535 shown in various ones of FIG. 5). In some example embodiments, a combined electrogram (e.g., a bipolar electrogram) (not shown) may be determined (e.g., by instructions provided by a program) from the respective electrograms associated with each transducer of the respective set of two or more of the transducers. The program may include instructions configured to display the combined electrogram via the input-output device system. Other forms of activation are possible in other embodiments involving activation of a respective set of two or more of the transducers. In some embodiments, activation under the influence of the instructions configured to activate a respective pair of transducers associated with a selected between graphical element may be referred to as bipolar activation when the pair of the transducers is activated in a bipolar manner (e.g., bipolar ablation or bipolar electrogram generation). Selection of each of at least some of the plurality of graphical elements 501 or 601 in accordance with the instructions of block 710 may include independent selections of each of the at least some of the graphical elements 501 or 601.

Having discussed embodiments where blocks 710 and 712 follow block 702 in FIG. 7A, a discussion will now begin regarding embodiments where block 704 follows block 702. Block 704 of method 700, in some embodiments, includes instructions (e.g., input instructions included in a program) that cause the data processing device system (e.g., data processing device systems 110 or 310) to receive transducer data from at least some of the transducers via the input-output device system. This transducer data can take various forms, such as one or more of various detected characteristics including, but not limited to, e.g., electrical characteristics (such as electrical potential or impedance), thermal characteristics (such as temperature), and force.

Various embodiments can process or analyze the transducer data received by the data processing device system according to the instructions of block 704 in order to, for example, generate and possibly display one or more electrograms, determine the acceptability of selection or activation of particular transducers, generate a map (e.g., a map of anatomical features), determine the status of tissue ablation, or combinations of these tasks. Accordingly, it should be noted that some embodiments need not be limited to any particular form of processing or analysis of the transducer data received by the data processing device system according to the instructions of block 704. In this regard, although various embodiments need not be limited to any particular processing or analysis of the transducer data received according to the instructions of block 704, block 706 of method 700 pertains to some embodiments where the transducer data is analyzed to identify various regions that correspond to at least a portion of one or more anatomical features. For example, according to some embodiments, block 706 includes instructions (e.g., determination or identification instructions included in a program) that are configured to identify various regions 525 (e.g., FIGS. 5C-5I) in the graphical representation (generated according to the instructions of block 702) that correspond to at least a portion of one or more anatomical features based at least on an analysis of the transducer data.

In embodiments such as these, where the transducer-based device is deployed in a bodily cavity (e.g., when the transducer-based device takes the form of a catheter device arranged to be percutaneously or intravascularly delivered to a bodily cavity), it may be desirable to perform various mapping procedures in the bodily cavity. Although these mapping procedures can be implemented according to the instructions of block 706, these mapping procedures can be performed at other times, such as any time during the generation of or after the display of the graphical representation of at least a portion of the transducer-based device (e.g., block 702, 802, or 902). It is noted that in some embodiments, the mapping procedure need not be limited to the mapping of various anatomical landmarks. For example, when the bodily cavity is an intra-cardiac cavity, the mapping procedure may include mapping electrophysiological activity in the intra-cardiac cavity. In some embodiments, the mapping procedure may include mapping varying degrees of contact between various ones of the transducers (e.g., electrodes) and a tissue surface of a bodily cavity into which the transducers are located.

An example of the mapping performed by devices according to various embodiments (such as those represented by block 706 in FIG. 7A) would be to locate the position of the ports of various bodily openings positioned in fluid communication with a bodily cavity. For example, in some embodiments, it may be desired to determine the locations of various ones of the pulmonary veins or the mitral valve that each interrupt an interior surface of an intra-cardiac cavity such as a left atrium.

In some example embodiments, the mapping is based at least on locating such bodily openings by differentiating between fluid and tissue (e.g., tissue defining a surface of a bodily cavity). There are many ways to differentiate tissue from a fluid such as blood or to differentiate tissue from a bodily opening in case a fluid is not present. Four approaches may include by way of non-limiting example:

1. The use of convective cooling of heated transducer elements by fluid. A slightly heated arrangement of transducers that is positioned adjacent to the tissue that forms the interior surface(s) of a bodily cavity and across the ports of the bodily cavity will be cooler at the areas which are spanning the ports carrying the flow of fluid.

2. The use of tissue impedance measurements. A set of transducers positioned adjacently to tissue that forms the interior surface(s) of a bodily cavity and across the ports of the bodily cavity can be responsive to electrical tissue impedance. Typically, heart tissue will have higher associated tissue impedance values than the impedance values associated with blood.

3. The use of the differing change in dielectric constant as a function of frequency between blood and tissue. A set of transducers positioned around the tissue that forms the interior surface(s) of the atrium and across the ports of the atrium monitors the ratio of the dielectric constant from 1 KHz to 100 KHz. Such can be used to determine which of those transducers are not proximate to tissue, which is indicative of the locations of the ports.

4. The use of transducers that sense force (e.g., force sensors). A set of force detection transducers positioned around the tissue that forms the interior surface of the bodily cavity and across the bodily openings or ports of the bodily cavity can be used to determine which of the transducers are not engaged with the tissue, which is indicative of the locations of the ports.

Figure 5C:
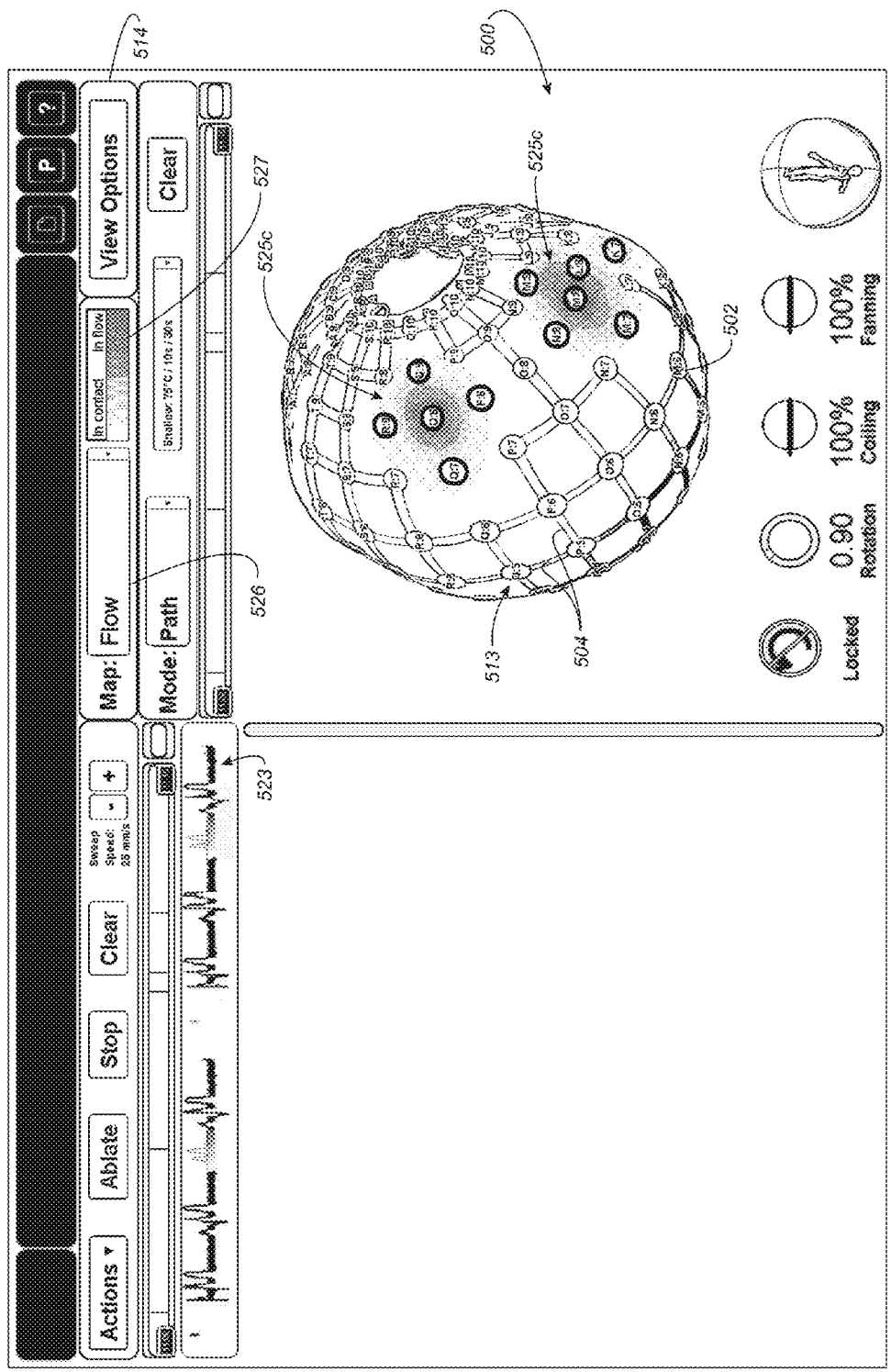
FIG. 5C illustrates the graphical representation provided by the graphical interface of FIG. 5A with the addition of various regions determined based at least on an analysis of transducer data.
Figure 5D:
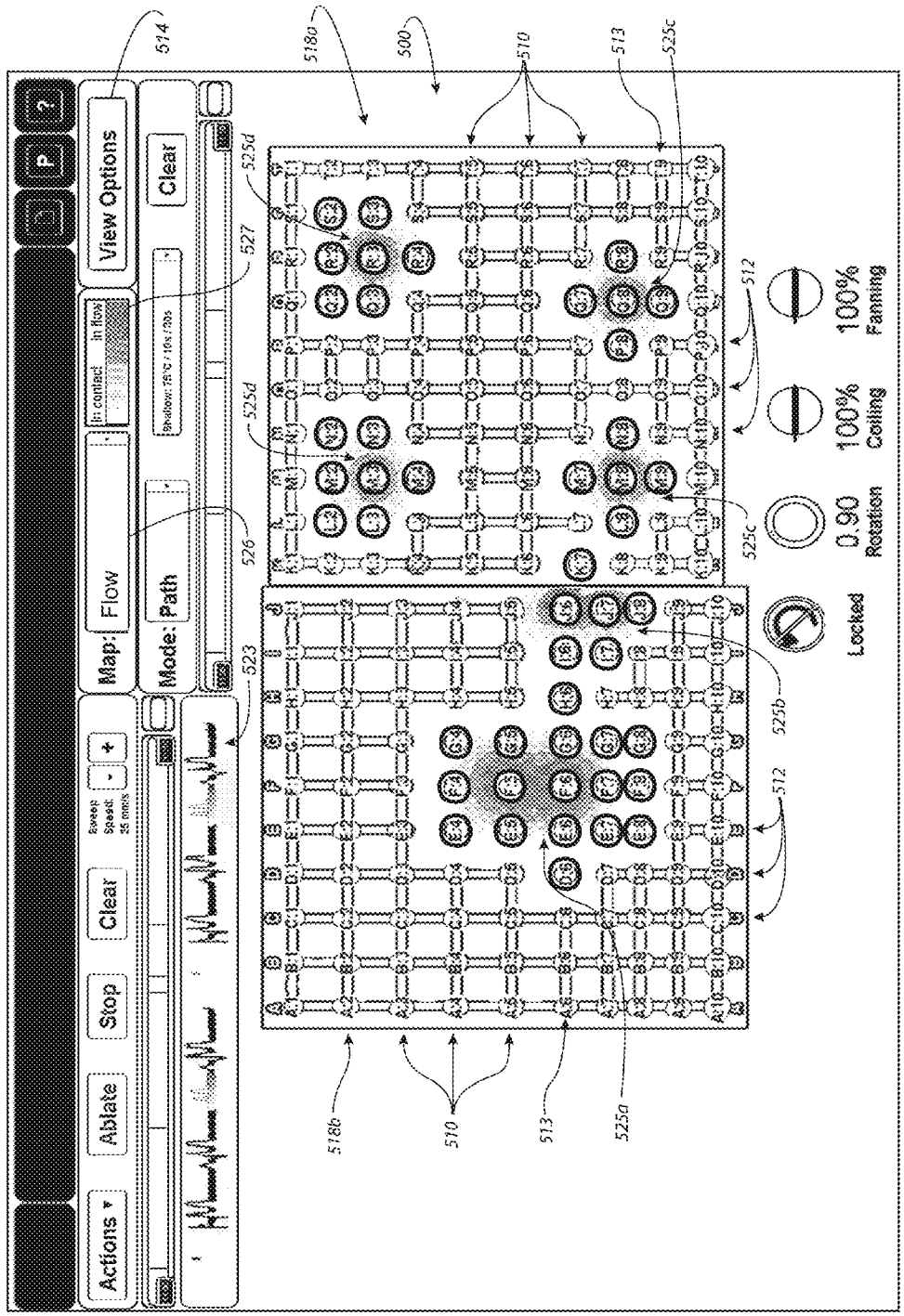
FIG. 5D illustrates the graphical representation of FIG. 5C depicted two-dimensionally.

The graphical interface of FIG. 5C includes various regions 525*c* (e.g., part of a plurality of regions collectively referred to as regions 525 when considering all of the FIG. 5) added to the graphical representation 500 of the transducer-based device. The regions 525 could be identified and displayed according to the instructions of block 706 in FIG. 7A in some embodiments. Although, such regions 525 could be identified and displayed at other times or according to other instructions. In some embodiments, the graphical interface depicted in FIG. 5C is generated after the transducer-based device was received in a bodily cavity having various anatomical features of interest and the control button 526 identified as "Map" was activated via the input-output device system to select a mode referred to as "Flow". Techniques for flow-based mapping techniques are disclosed in commonly assigned U.S. Patent Application Publication No.: US 2008/0004534. In various embodiments associated with various ones of FIG. 5, the anatomical features of interest are mapped ports of a mitral valve and various pulmonary veins positioned in fluid communication with an intra-cardiac cavity (e.g., a left atrium in this embodiment) depicted as interrupting a surface of a tissue wall of the intra-cardiac cavity (although other bodily cavities could be mapped by the systems or device systems described herein). In these various embodiments, the transducers of the transducer-based device are distributed adjacent respective regions in the intra-cardiac cavity that can include relatively lower blood flow regions (e.g., adjacent a tissue surface of the intra-cardiac cavity), relatively higher flow regions (e.g., over the ports of the intra-cardiac cavity). It is noted that relatively lower blood flow regions in the intra-cardiac cavity may occur when a transducer is positioned in contact with a tissue surface to restrict blood flow at the contacted tissue. In some example embodiments, the relatively large number of transducers in the distribution advantageously allows for each of the transducers to be positioned adjacent their corresponding regions with little or no repositioning of the transducer-based device thereby facilitating obtaining transducer-based data concurrently from a multitude of locations in the bodily cavity. In this example embodiment, activation via the input-output device system of the control button 526 identified as "Map" can allow for other types of maps, including but not limited to, tissue contact maps, isochronal maps, isopotential maps, propagation maps, and various other voltage maps associated with intra-cardiac electrical activity.

Returning to the specific case of block 706 in FIG. 7A, one or more of the above-discussed mapping procedures may be implemented according to instructions of block 706 to identify various regions 525 in the graphical representation that correspond to at least a portion of one or more anatomical features based at least on an analysis of the transducer data received according to block 704. In some of these embodiments, the one or more anatomical features are the ports of various bodily openings (e.g., pulmonary veins, left lateral appendage, mitral valve) positioned in fluid communication with the intra-cardiac cavity and the transducer data includes data containing various blood flow data within the bodily cavity. In this embodiment, the instructions in block 706 include instructions that are configured to cause the input-output device system to display the identified regions 525 of the graphical representation 500. In this example embodiment, the various ones of the identified regions 525 are shown in the three-dimensional graphical representation 500 provided by the graphical interface of FIG. 5C and the two-dimensional graphical representation 500 provided by the graphical interface of FIG. 5D.

In FIG. 5D, the relatively large region 525a is associated with the mitral valve, region 525b is associated with the left lateral appendage, regions 525c are associated with the left pulmonary vein group and regions 525d are associated with the right pulmonary vein group. Each of the regions 525 is depicted in the graphical representation 500 with a graduated pattern provided by the flow identifier 527 in the graphical interface of FIG. 5D. A graduated pattern can be employed to indicate various regions in the graphical representation corresponding to different regions of flow in the intra-cardiac cavity. The identified regions 525 may be identified by any suitable methods including the use of gray-scale patterns, different colors, different opacities, different intensities and different shapes. It is understood that other embodiments may employ other techniques to identify regions in the graphical representation corresponding to a desired anatomical feature. For example, transducer-based data containing blood and tissue impedance information may be employed to determine regions 525. As previously discussed in this detailed description, a selection box 522 may be optionally enabled to allow for the selective inclusion in the graphical representation of graphical elements associated with various anatomical features associated with regions 525.

Identification of the regions 525 may be motivated for various reasons. For example, in embodiments in which transducers of transducer-based device are activated to treat or diagnose various regions in a bodily cavity, the identification of various regions 525 and their spatial relationship relative to one another may impact the efficacy of the treatment or diagnostic procedure. For example, in situations in which at least some of the transducers of a transducer-based device are employed to ablate various regions within an intra-cardiac cavity (e.g., to treat atrial fibrillation), ablation of a pulmonary vein may result in an undesired condition referred to as pulmonary stenosis. Identification of regions 525c, 525d in the graphical representation may be employed to reduce occurrences of this undesired condition.

In some embodiments, contrary to what is shown in FIG. 7A, block 706 immediately precedes block 710, with block 707, block 708, or both omitted. However, in some embodiments, block 707 is between blocks 706 and 710 as shown in FIG. 7A. In addition, in some embodiments, block 707 need not occur between blocks 706 and 710 as shown in FIG. 7A, and can, for example, instead occur immediately after block 704, with block 710 immediately following and block 706 omitted. Similarly, in some embodiments, block 708 is between blocks 706 and 710 as shown in FIG. 7A. However, in some embodiments, block 708 need not occur between blocks 706 and 710 as shown in FIG. 7A, and can, for example, instead occur immediately after block 704, with block 710 immediately following and block 706 omitted.

In any event, regarding block 707 and block 710, concurrent selection of a set of two or more of the transducers in the transducer-based device (e.g., a pair of adjacent transducers 306) is provided in some embodiments for enhanced workflows that are less cumbersome and more expeditious than those associated with non-concurrent selection of each transducer of the set of two or more of the transducers. For example, in some embodiments, a user-based selection of a between graphical element (e.g., between graphical elements 504 or 604) allows for a machine-based concurrent selection of an associated set of two or more transducers in various embodiments.

In this regard, block 707 includes, in some embodiments, identification instructions (e.g., instructions provided in a program) configured to cause identification of which of the respective transducers of each of various sets of two or more of the transducers of a transducer-based device are and which are not acceptable for concurrent selection.

Concurrent selection or non-concurrent selection of the respective transducers of a given one of the sets of two or more of the transducers may be motivated for various reasons. For example, concurrent selection of transducers may lead to a more expeditious workflow that advantageously reduces diagnostic or treatment times. Conditions, however, may not allow for the concurrent selection of the respective transducers of each of various ones of selectable sets of two or more transducers.

For example, if a transducer of a transducer pair is deemed not-activation-ready (e.g., according to the instructions of block 708 or block 804, discussed below), the transducer pair can be deemed, according to the instructions of block 707, to be a transducer set that is not acceptable for concurrent selection. A set of two or more transducers (e.g., a pair of transducers) that is identified (e.g., via instructions of block 708 or block 804, discussed below) as including at least one not-activation-ready transducer of the transducer-based device (e.g., a not-ablation-ready transducer) may, in some embodiments, be deemed, according to the identification instructions of block 707, as a set of two or more of the transducers of a transducer-based device whose respective transducers are not acceptable for concurrent selection. In some embodiments, a set of two or more of the transducers that is identified (e.g., via instructions of block 708 or block 804, discussed below) as not including any not-activation-ready transducer of the transducer-based device (e.g., a not-ablation-ready transducer) may be deemed, according to the identification instructions of block 707, as a set of two or more of the transducers whose respective transducers are acceptable for concurrent selection.

The identification instructions of block 707 need not be limited to causing identification of a set of two or more transducers as acceptable or not acceptable for concurrent selection, and need not be limited to determining the acceptability of concurrency of selection based upon a determination of activation-ready transducers (e.g., via instructions of block 708 or block 804, discussed below). In some embodiments, the identification instructions of block 707 include instructions configured to cause, at least in part, the identification of the respective transducers of each of the sets of two or more transducers which are acceptable for concurrent selection based at least on an analysis of transducer data received in accordance with the instructions of block 704. In other words, acceptability of the concurrency of selection can be determined on a transducer-group basis or on an individual-transducer basis. These differing approaches can lend themselves to different circumstances. For example, in some situations, it may be preferable to determine whether an entire group of transducers is acceptable for concurrent selection, while in other situations, it may be beneficial to know whether individual transducers in each group are acceptable for concurrent selection.

In some embodiments, each of the sets of two or more of the transducers of the transducer-based device including a pair of adjacent transducers that are spaced with respect to one another across a corresponding region of space, each region of space not including any transducer. In some of these embodiments, a determination of whether or not one of these regions of space is acceptable for activation by its corresponding respective transducer pair is used as a basis for determining whether or not the respective transducer pair is acceptable for concurrent selection. For example, if the region of space is deemed to be acceptable for activation by the corresponding respective transducer pair, then the respective transducer pair is identified as being acceptable for concurrent selection in some embodiments. In some embodiments, the regions of space are determined to be acceptable for activation of the corresponding respective transducers according to determination instructions (e.g., according to some embodiments of the instructions of block 708 in FIG. 7A or block 804 in FIG. 8, discussed below). In this regard, the identification instructions of block 707 may be further configured to cause, at least in part, the identification of the respective transducers of each of the pairs of adjacent ones of the transducers which are acceptable for concurrent selection as the respective transducers of each of the plurality of pairs of adjacent transducers whose corresponding regions of space have been determined, according to determination instructions (not shown, but similar to the instructions of block 708 or block 804, discussed below) to be acceptable for activation of the corresponding respective transducers, and cause, at least in part, the identification of the respective transducers of each of the pairs of adjacent ones of the transducers which are not acceptable for concurrent selection as the respective transducers of each of the plurality of pairs of adjacent transducers whose corresponding regions of space have been determined, according to the determination instructions (not shown, similar to the instructions of block 708 or block 804, discussed below) to be not acceptable for activation of the corresponding respective transducers.

Acceptability of concurrency of selection of transducers or a region of space corresponding to transducers need not based on or solely on a determination of the acceptability of activation of the corresponding transducers (e.g., pursuant to instructions according to block 708 or block 804, discussed below) in some embodiments. In this regard, transducers or regions of space each corresponding to transducers can be deemed to be acceptable or not acceptable for concurrent selection, according to various embodiments of the instructions of block 707, based on any reason which might make it beneficial or not beneficial to concurrently select the corresponding transducers.

In some embodiments, a result of one or more of the identifications according to the instructions of block 707 is the distinguishing display (e.g., by different visual characteristics) of graphical elements associated with transducers identified to be acceptable for concurrent selection as compared to graphical elements associated with transducers identified to be not-acceptable for concurrent selection. In this regard, the instructions according to block 707 include, in some embodiments, instructions configured to cause the graphical representation displayed according to the instructions of block 702 to visually distinguish its graphical elements associated with transducers identified to be acceptable for concurrent selection as compared to graphical elements associated with transducers identified to be not-acceptable for concurrent selection. In this regard, any instructions according to block 707 that affect the appearance of the graphical representation can be considered to be part of block 702 in some embodiments. The same applies to block 708 (with respect to block 702) in FIG. 7A, block 804 (with respect to block 802) in FIG. 8, block 812 (with respect to block 802) in FIG. 8, block 910 (with respect to block 902) in FIG. 9, block 912 (with respect to block 902) in FIG. 9, discussed below, and any other similar discussions herein, where distinguishing visual characteristics of graphical elements in a graphical representation facilitate differences in information or status.

To elaborate with respect to block 702 for example purposes only, various graphical element sets may be displayed by the display instructions of block 702, each graphical element set including one or more graphical elements (e.g., graphical elements 501 or 601) and each graphical element set associated with a respective one of a number of sets of two or more of the transducers (e.g., transducers of transducer-based devices 200, 300 or 400). Method 700 may include instructions (e.g., instructions provided in a program), (not shown) configured to cause graphical representation instructions of block 702 to cause the input-output device system (e.g., input-output device system 120 or 320) to display each of the graphical element sets associated with each of the sets of two or more of the transducers whose respective transducers have been identified (e.g., according to identification instructions associated with block 707) to be acceptable for concurrent selection with a respective set of visual characteristics that distinguishes each of the graphical element sets associated with each of the sets of two or more of the transducers whose respective transducers have been identified to be acceptable for concurrent selection from each of the graphical element sets associated with each of the sets of two or more of the transducers whose respective transducers have been identified to be not acceptable for concurrent selection. Differences in the displayed visual characteristics may include different colors, opacities, hues, intensities, shading, patterns, shapes or the addition or removal of any displayed information suitable for distinguishing a concurrently-selectable transducer set from a not-concurrently-selectable transducer set.

For example, in some embodiments associated with FIGS. 5C and 5D, only the between graphical elements 504 that are each associated with a corresponding set of transducers (e.g., a corresponding pair of transducers in this embodiment) whose respective transducers are deemed acceptable for concurrent selection are displayed, and between graphical elements 504 that are associated with a corresponding pair of transducers that include at least one transducer that is deemed not acceptable for concurrent selection are not displayed. The presence or absence of a particular graphical element (e.g., a between graphical element 504) may form at least part of differences associated with displayed visually characteristics referenced in block 707.

In various embodiments of FIGS. 5C and 5D, the absent between graphical elements 504 indicate that their respective pairs of transducers each have been identified (e.g., according to the instructions of block 708, discussed below) to be over a region of space that is deemed unacceptable for activation (e.g., ablation) because such regions of space include a portion of a port of a bodily opening, which, in some embodiments, is not acceptable for ablation. These identifications lead to a conclusion, in some embodiments, (e.g., according to the instructions of block 707), that these respective pairs of transducers are not acceptable for concurrent selection in some embodiments. In some of these embodiments, such as those illustrated by FIGS. 5C and 5D, the graphical elements associated with these respective transducer pairs identified not to be acceptable for concurrent selection, are not displayed so that they are visually distinguished from the between graphical elements 504, which are displayed and which are associated with respective transducer pairs that have been identified to be acceptable for concurrent selection according to the instructions of block 707.

One reason for identifying a transducer set as being not-acceptable for concurrent selection according to the instructions of block 707 is that the transducer set, when activated, could be harmful to an affected region of space. However, other factors may also have a bearing on whether the respective transducers of a particular set of two more of the transducers are deemed concurrently selectable. In addition, combinations of different factors may be considered in the determination of whether the respective transducers of a particular set of two or more of the transducers are, or are not, acceptable for concurrent selection.

By way of a non-limiting example, another reason for determining a transducer set to be not-acceptable for concurrent selection, according to some embodiments of the instructions of block 707, is that transducers in the transducer set are too far apart, such that, for example, activation of the transducers in the set would lead to a result that may be considered ineffective. For example, if a transducer pair is too far apart, ablation performed by the pair might not be able to reliably form an electrophysiological conduction block between them.

Figure 5E:
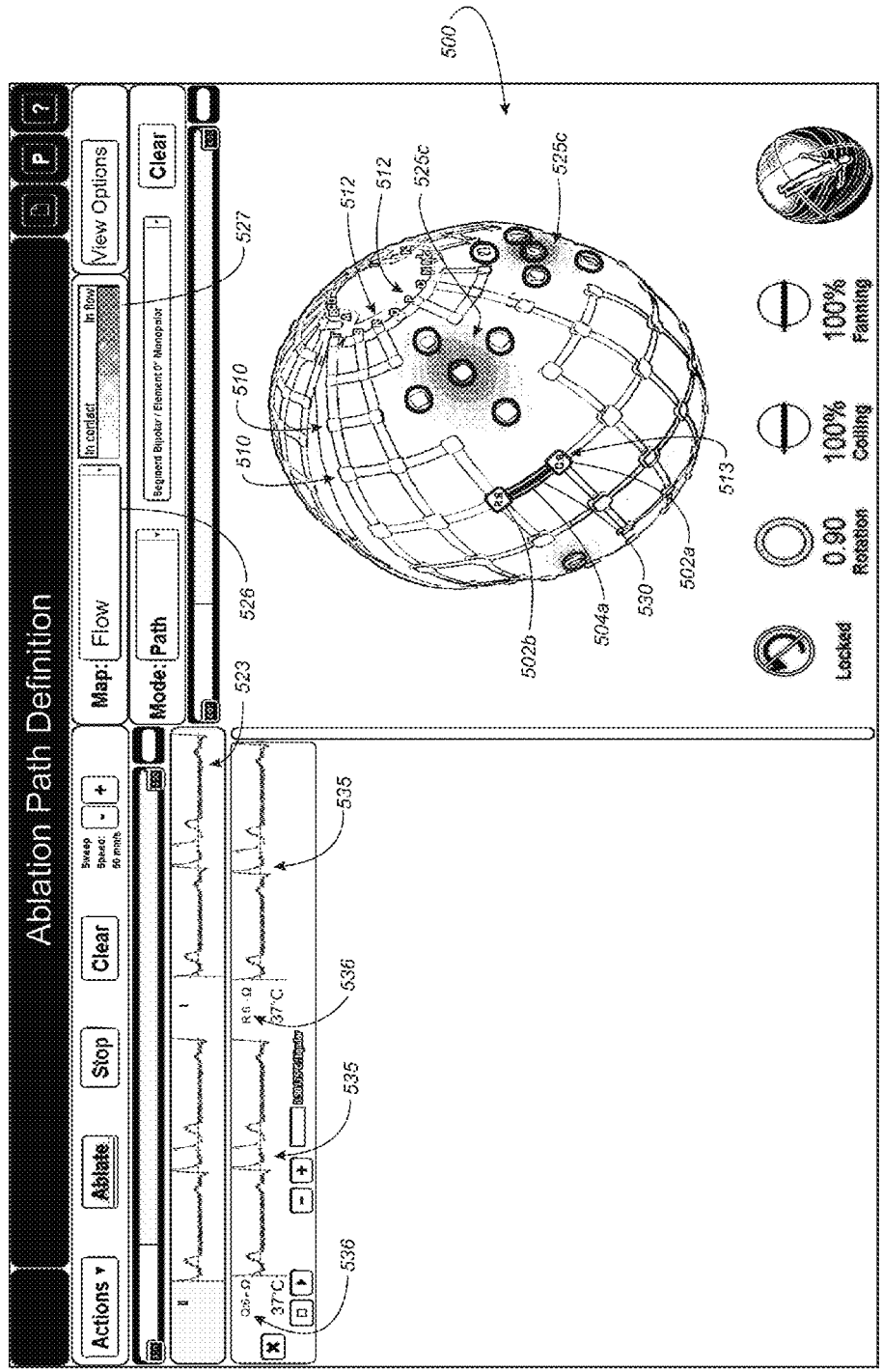
FIG. 5E illustrates the graphical representation of FIG. 5C with a graphical element selected in accordance with various example embodiments.
Figure 5F:
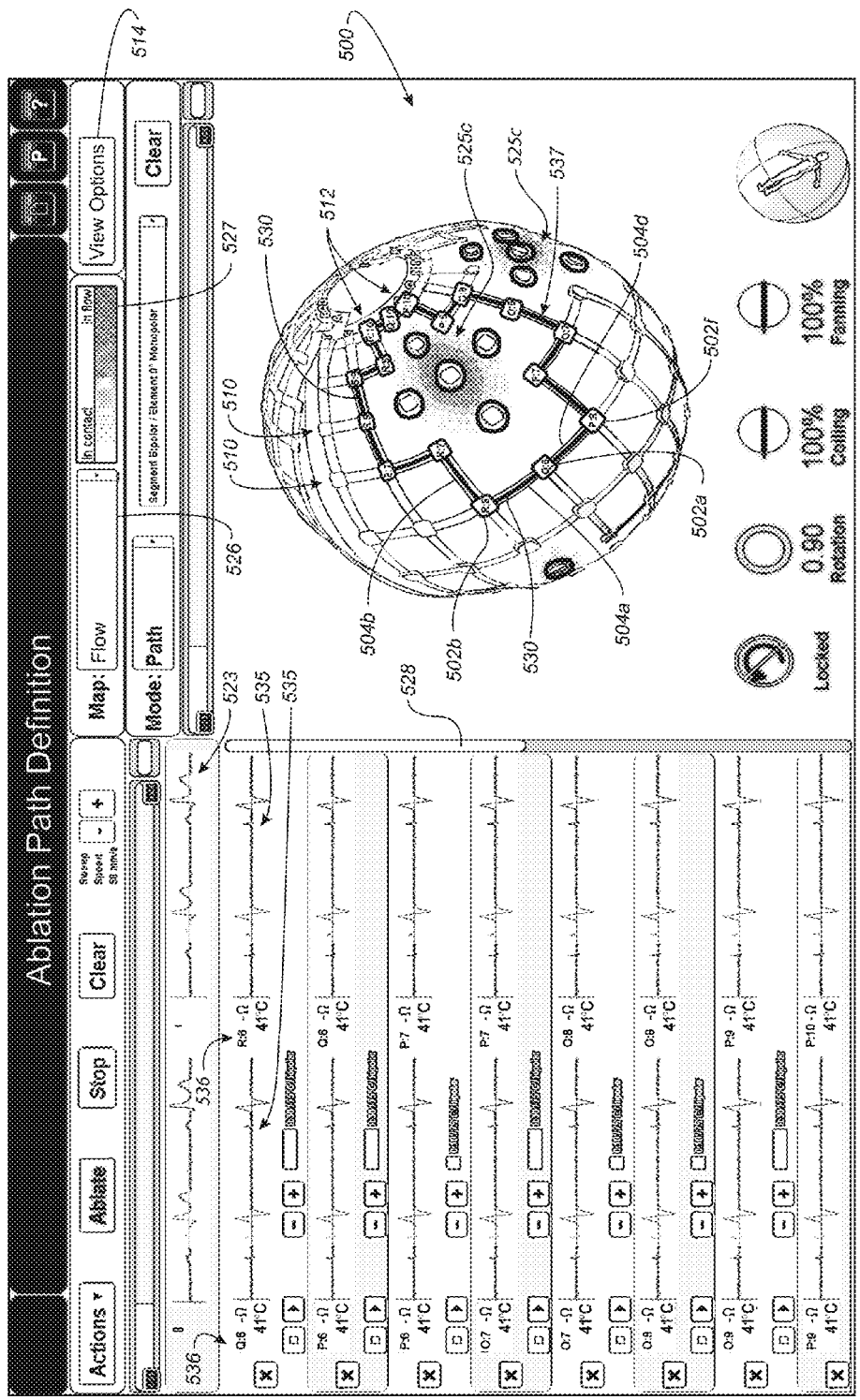
FIG. 5F illustrates the graphical representation of FIG. 5C with an addition of a depicted path.
Figure 5G:
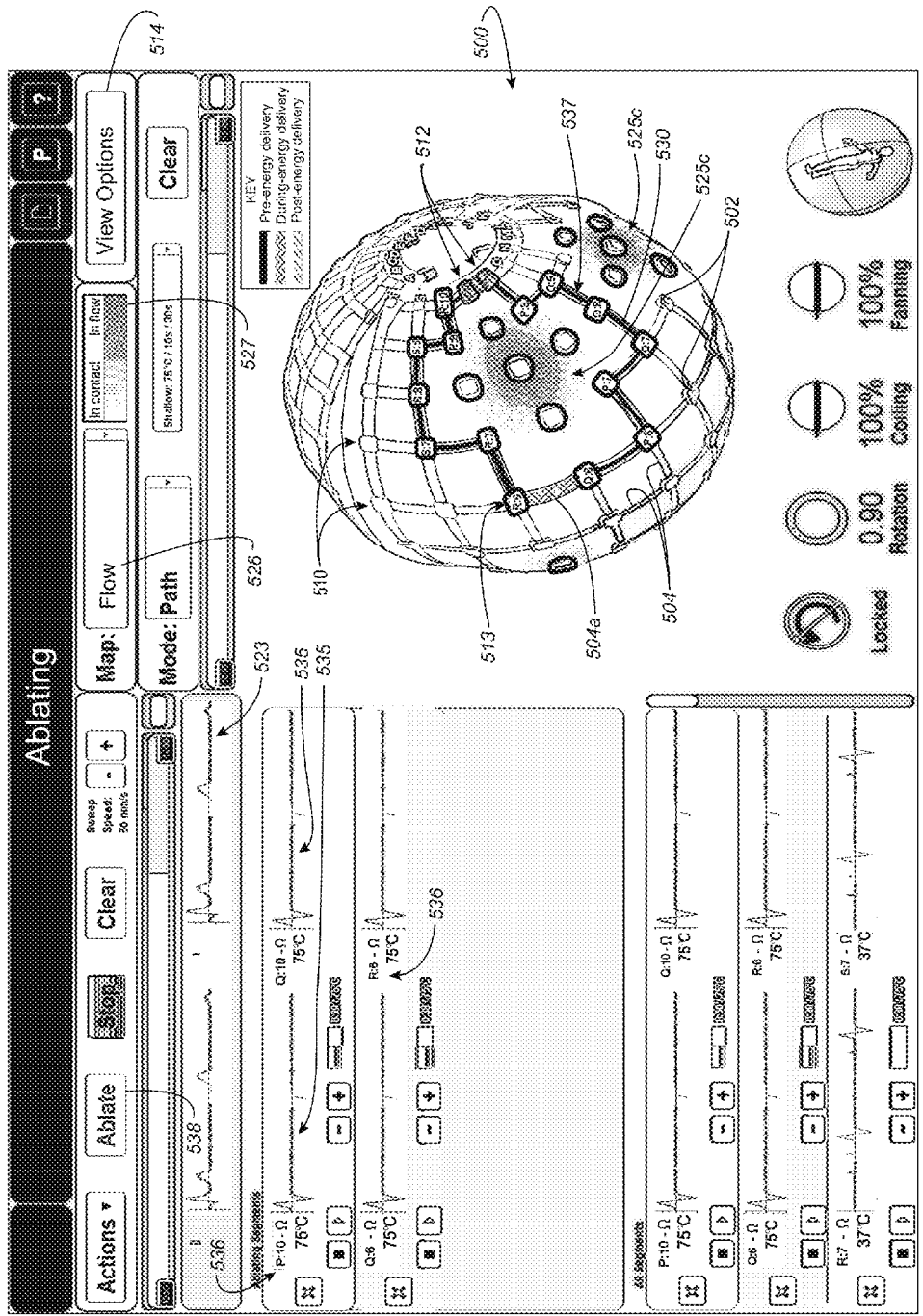
FIGS. 5G and 5H illustrate the graphical representation of FIG. 5F associated with two successive activations of various transducer sets selected according to a first sequence but activated according to a second sequence different from the first sequence.
Figure 5H:
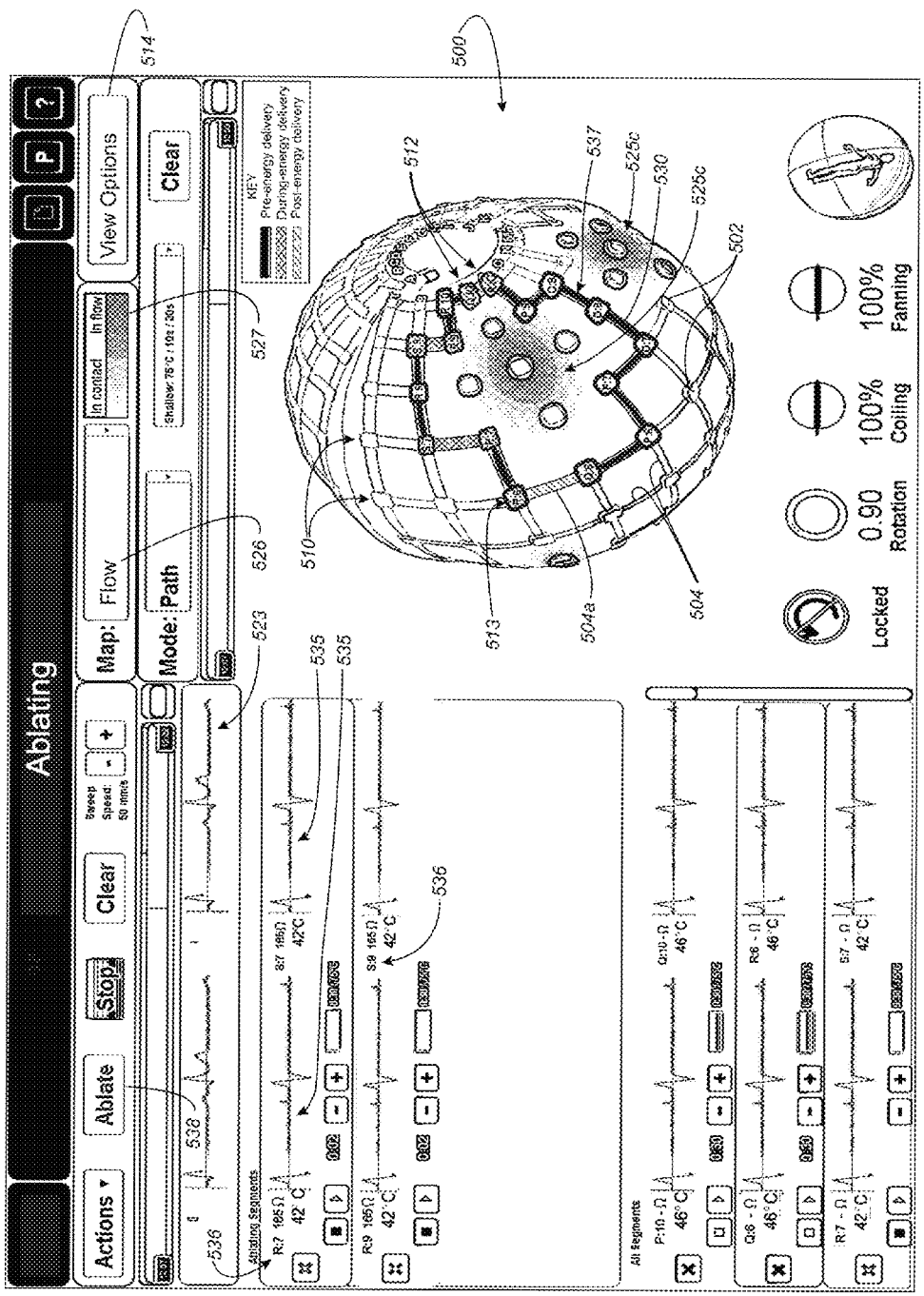
Figure 5I:
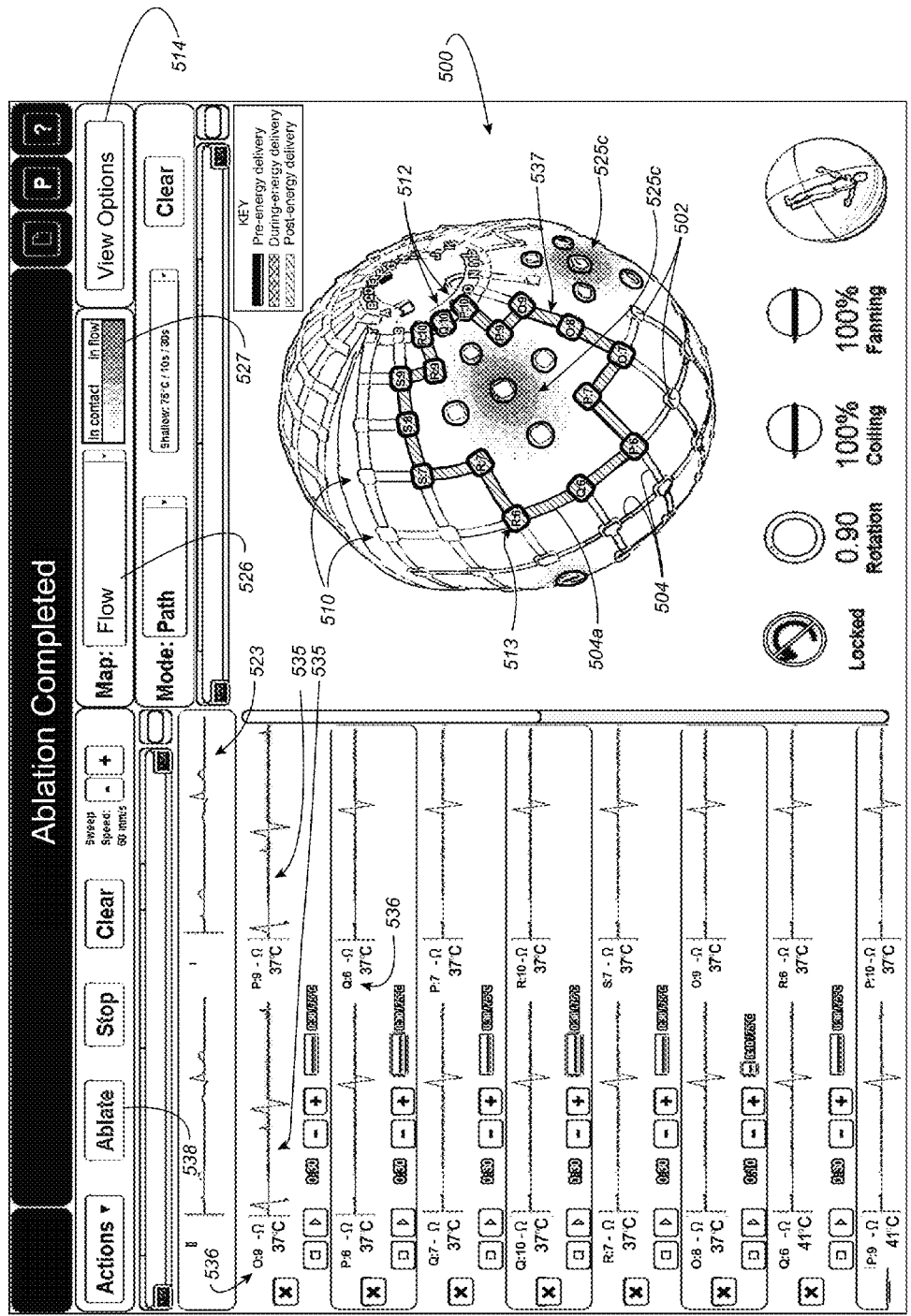
FIG. 5I illustrates the graphical representation of FIG. 5F after the completion of the activation of all the various transducer sets according to the second sequence.
Figure 5J:
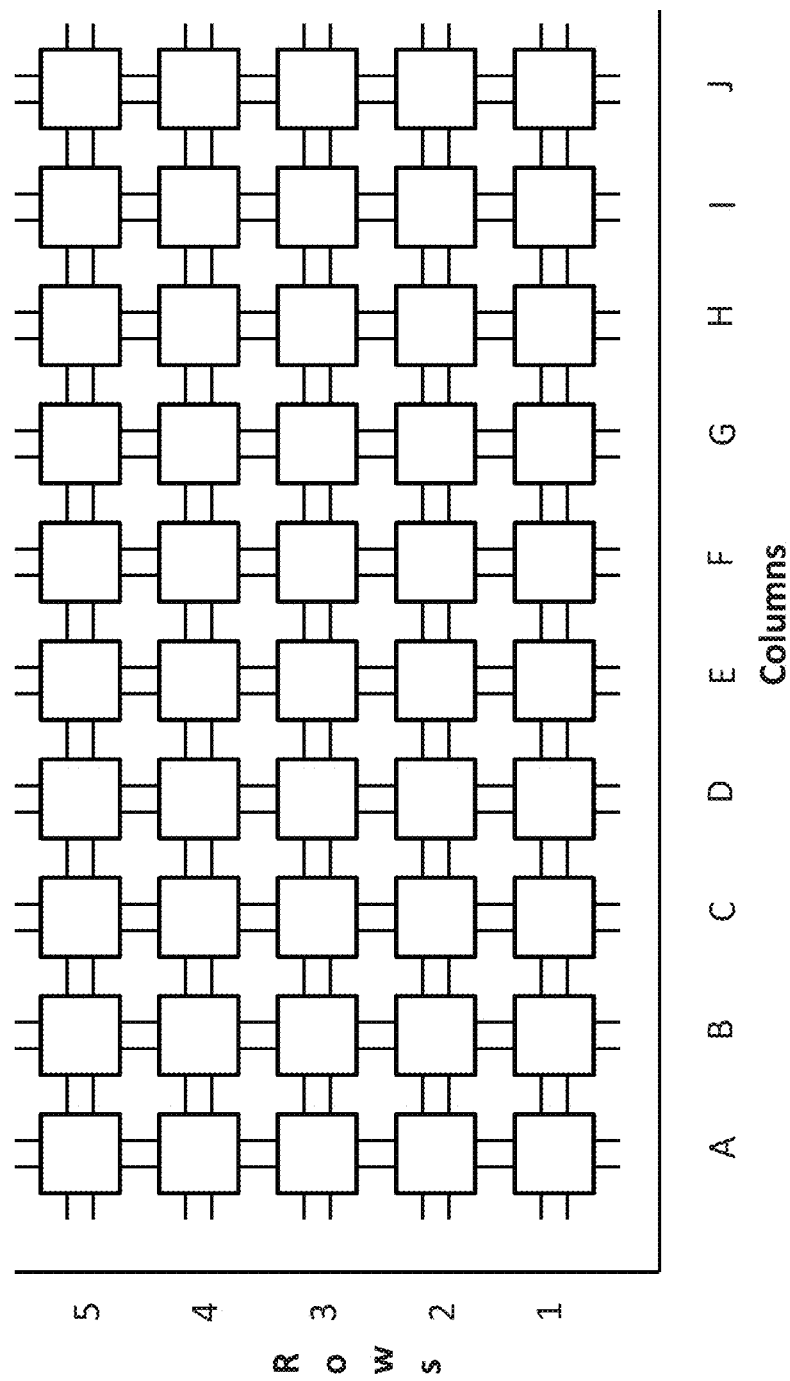
FIG. 5J illustrates a symbolic representation of some transducer graphical elements and between graphical elements which may be displayed according to any of the graphical representations of FIGS. 5A-5I, 5K, and 6, according to various example embodiments.
Figure 5K:
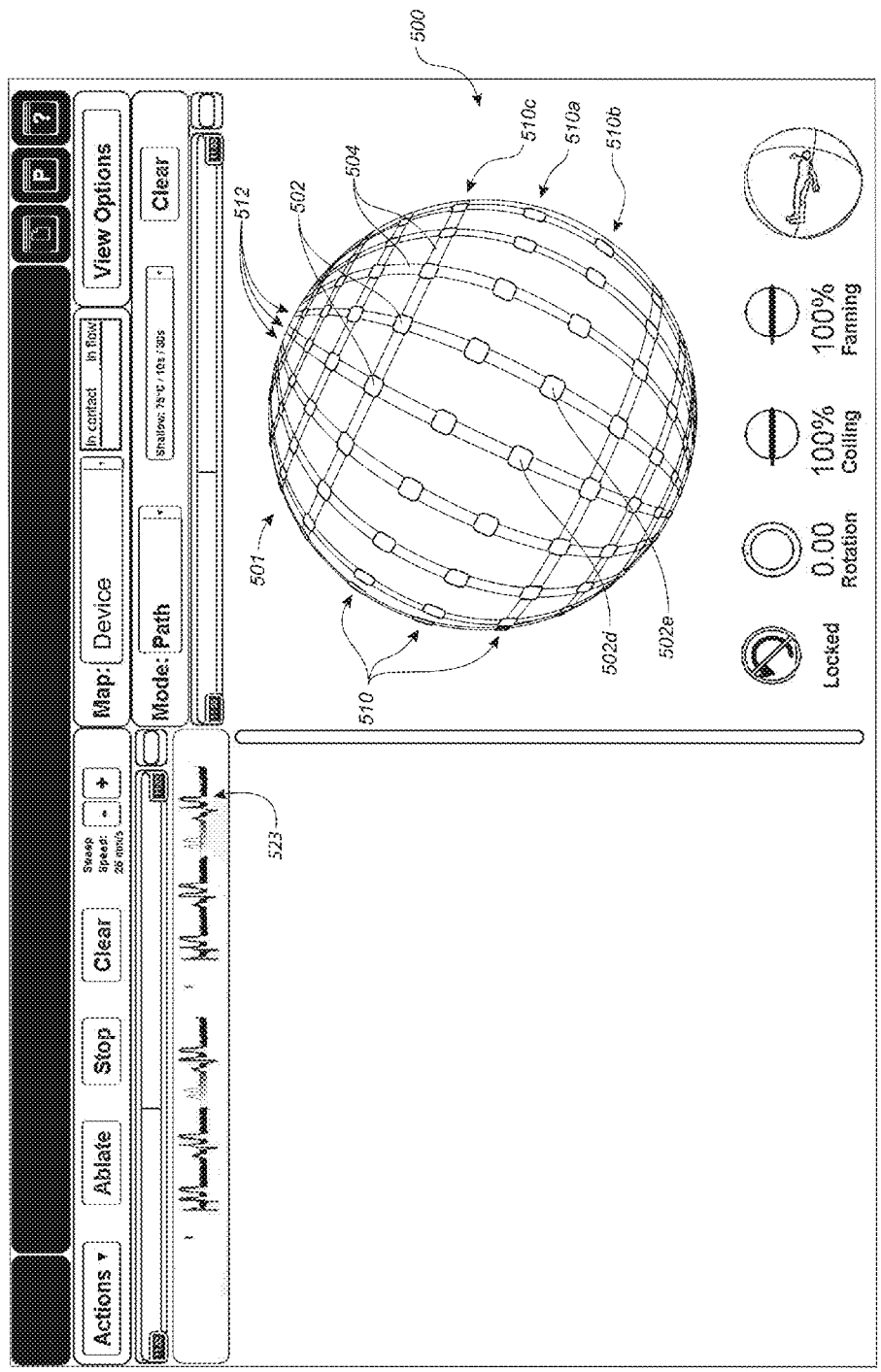
FIG. 5K illustrates a graphical interface providing a graphical representation of at least a portion of a transducer-based device according to various example embodiments.

The embodiments of FIG. 5K illustrate examples of transducer pairs being too far apart and, therefore, being deemed to be unacceptable for concurrent selection according to some embodiments of the instructions of block 707. In this regard, FIG. 5K illustrates a graphical interface including a graphical representation 500 provided by an input-output device system (e.g., input-output device system 120 or 320) according to some embodiments. Graphical representation 500 in FIG. 5K is similar to the graphical representation 500 in FIG. 5A and includes a plurality of graphical elements including various transducer graphical elements and between graphical elements. For convenience of discussion, the plurality of graphical elements of graphical representation 500 are identified as graphical elements 501, the plurality of transducer graphical elements of graphical representation 500 are identified as transducer graphical elements 502, and the between graphical elements of graphical representation 500 are identified as between graphical elements 504. The graphical elements 501 in graphical representation 500 in FIG. 5K are arranged in a plurality of rows 510 (e.g., latitudinal rows) and a plurality of columns 512 (e.g., longitudinal columns) in a manner similar to that shown by graphical representation 500 in FIG. 5A. The transducer graphical elements 502 and between graphical elements 504 in graphical representation 500 in FIG. 5K have similar associations with a spatial distribution of transducers (e.g., transducers 306 in FIG. 3A, 3B) as their counterparts in graphical representation 500 in FIG. 5A.

In this illustrated embodiment, graphical representation 500 in FIG. 5K is distinguished from graphical representation 500 in FIG. 5A in various ways including an absence of a between graphical element 504 between the respective transducer graphical elements 502 of various adjacent pairs of the transducers graphical elements 502. For example, a between graphical element 504 is not displayed between adjacent transducer graphical elements 502d and 502e. In this illustrated embodiment, an absence of between graphical elements 504 occurs in some of the rows 510. In this illustrated embedment, the presence or absence of a particular between graphical element 504 in the graphical representation 500 in FIG. 5K is indicative, at least in part, of differences in the visual characteristics of particular graphical elements 501 associated with sets of two or more transducers whose respective transducers have been identified by the instructions of block 707 to be acceptable for concurrent selection and particular graphical elements 501 associated with sets of two or more transducers whose respective transducers have been identified by the instructions of block 707 to be not acceptable for concurrent selection. In various example embodiments, between graphical elements 504 are displayed between corresponding pairs of transducer graphical elements 502 associated with transducers that have been identified by the instructions of block 707 to be acceptable for concurrent selection, while between graphical elements 504 are not displayed between corresponding pairs of transducer graphical elements 502 associated with transducers that have been identified by the instructions of block 707 to be not acceptable for concurrent selection.

In some example embodiments, the instructions 707 are further configured to cause, at least in part, the identification of the respective transducers of each of the pairs of adjacent ones of the transducers in a distribution which are acceptable for concurrent selection as the respective transducers of each of the plurality of pairs of adjacent ones of the transducers in the distribution having a respective transducer-to-transducer distance that is not greater than a target transducer-to-transducer distance, and cause identification, at least in part, of the respective transducers of each of the pairs of adjacent ones of the transducers in the distribution which are not acceptable for concurrent selection as the respective transducers of each of the plurality of pairs of adjacent ones of the transducers in the distribution having a transducer-to-transducer distance that is greater than the target transducer-to-transducer distance. In embodiments involving relatively low temperature ablations, the target transducer-to-transducer distance might be one-half an electrode width. In embodiments involving relatively higher temperature ablations, larger target transducer-to-transducer distances might be sufficient. In various embodiments, ablation temperatures lower than the thermal coagulation temperature of blood are preferred. Other factors that may impact the target transducer-to-transducer distance might include tissue thickness, tissue type, characteristics of fat layers embedded in the tissue, the blood's susceptibility to forming coagulum, and whether or not a pair of transducers performing the ablation are separated by a physical portion of the transducer-based device, such as by an elongate member 304. In some embodiments, a target transducer-to-transducer distance associated with a particular pair of the transducers is determined or selected to increase a likelihood that a electrophysiological conduction block that blocks electrophysiological activity between the particular pair of transducers will be formed in tissue upon activation of the transducers. In some embodiments, concurrent selection of a pair of transducers whose activation would not likely result in a desired electrophysiological conduction block may be deemed unacceptable according to the instructions of block 707.

It is noted that different target transducer-to-transducer distances may be employed for different pairs of the transducers. For example, a first target transducer-to-transducer distance associated with a pair of transducers spaced with respect to one another over a region of space that includes a physical portion of a structure on which the transducers are located (e.g., structure 308) may be different (e.g., greater) than a second target transducer-to-transducer distance associated with a pair of transducer that are spaced with respect to one another across a region of space that does not include a physical portion of a supporting structure (e.g., structure 308). In the embodiments of FIG. 5K, between graphical elements 504 are not displayed between transducers graphical elements 502 arranged in particular ones of the rows 510 having the greatest depicted spacing between adjacent transducer graphical elements 502.

In some particular embodiments, between graphical elements 504 are not displayed between transducer graphical elements 502 arranged in rows 510a and 510b, because the transducer-to-transducer distances of the transducers (e.g., transducers 306) corresponding to these transducer graphical elements 502 in these rows each exceeds a target distance (e.g., in use). Therefore, in some embodiments, it is determined (e.g., according to the instructions of block 707) that the transducers corresponding to the transducer graphical elements 502 along rows 510a and 510b are not acceptable for concurrent selection, which results in the non-display of the corresponding between graphical elements 504. However, between graphical elements 504 are displayed between transducer graphical elements 502 arranged in the other rows (including row 510c), because the transducer-to-transducer distances of the transducers corresponding to these transducer graphical elements 502 in these rows each are within a target distance. Therefore, in some embodiments, it is determined (e.g., according to the instructions of block 707) that the transducers corresponding to the transducer graphical elements 502 along the other rows (besides rows 510a and 510b) are acceptable for concurrent selection, which results in the display of the corresponding between graphical elements 504.

It should be noted that although the embodiments of FIG. 5K illustrate the unacceptability of concurrency of selection of various transducer pairs latitudinally arranged on a supporting structure due to excessive transducer-to-transducer distance, acceptability of concurrency of selection of transducer pairs or larger groups can be determined on an individual transducer-group basis and based on other factors or other factors in conjunction with transducer-to-transducer distance. For example, a transducer-based device (e.g., similar to transducer-based device 300) represented by a graphical representation in FIG. 5K may contort when placed in a bodily cavity, and therefore, transducer-to-transducer distances may vary between transducer pairs in some directions (e.g., across regions of space that do not include a physical portion of the supporting structure). Therefore, in some embodiments, the transducer-to-transducer distances are calculated in real time for each possible transducer pair via transducer data received according to the instructions of block 704, and based at least upon this transducer data, each possible transducer pair is identified as being acceptable or not acceptable for concurrent selection according to the instructions of block 707, and the corresponding between graphical elements are consequently displayed or not displayed in the graphical representation. In some embodiments, a particular transducer pair is identified as being acceptable or not acceptable for concurrent selection according to the instructions of block 707 on the basis of other factors in addition to the transducer-to-transducer distance associated with the particular transducer pair (e.g., location of the transducer pair to a particular anatomical feature).

Further, in some embodiments, acceptability of concurrency of selection need not be performed on a transducer-pair-basis. For example, in some of these embodiments, a group of three or more transducers that could form one possible ablation path could be evaluated as a group to determine whether all transducers within that group are acceptable for concurrent selection, e.g., to determine whether a possible ablation path is acceptable of activation (e.g., ablation). In this regard, in some embodiments, the instructions of block 707 are configured to cause identification, for each of a plurality of transducer sets of three or more transducers (e.g., each representing a possible ablation path), whether or not all transducers within the corresponding transducer set are acceptable for concurrent selection.

Having discussed the identification of transducer sets that are acceptable and transducer sets that are not acceptable for concurrent selection according to the instructions of block 707, a discussion of some embodiments of graphical element selection and activation according to the instructions of blocks 710 and 712 in FIG. 7A will now be discussed with respect to FIG. 7B.

Figure 7B:
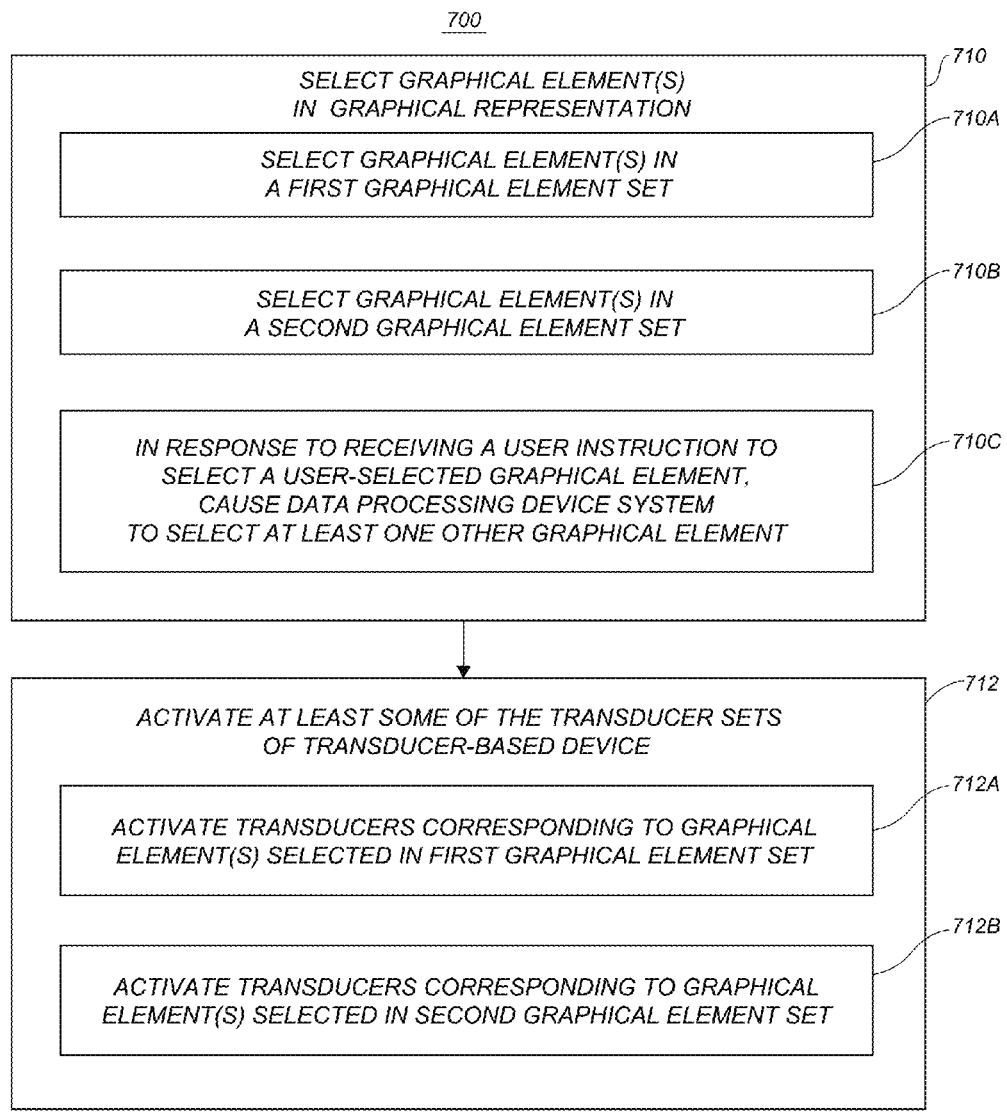
FIG. 7B illustrates an exploded view of some of the blocks of the block diagram of FIG. 7A according to some example embodiments.

FIG. 7B includes an exploded view of the selection instructions of block 710 and the activation instructions of block 712 according to some example embodiments. In some embodiments, all of the blocks shown in FIG. 7B may not be required. Block 710A includes first selection instructions (e.g., instructions provided in a program) configured to cause selection (e.g., a first selection) of at least one graphical element in a first graphical element set of a plurality of graphical element sets. In some embodiments, the first graphical element set is associated with a first one of the sets of two or more of the transducers whose respective transducers have been identified according to the instructions of block 707 to be acceptable for concurrent selection, and the first selection instructions are configured to cause concurrent selection, in response to the selection of the at least one graphical element in the first graphical element set, of the respective transducers of the first one of the sets of two or more of the transducers. However, identification of the respective transducers as acceptable for concurrent selection, and concurrent selection of the respective transducers may not be required in some embodiments.

For example, a user might directly select a between graphical element such as a between graphical element 504 or 604 (i.e., the between graphical element is a user-selected between graphical element), which might cause the first selection instructions to cause the data processing device system to (a) perform a machine-selection of the user-selected between graphical element (e.g., by changing its visual characteristics), and (b) perform a machine-selection (or in some embodiments, a concurrent selection) of the transducers in a transducer pair corresponding to the user-selected between graphical element. In some embodiments, the transducer pair is identified to be acceptable for concurrent selection. In some embodiments, the machine-based selection of the transducer pair may lead to an activation (or in some embodiments, a concurrent activation) of the transducers of that pair (e.g., block 712A, discussed below). In some embodiments, including, but not limited to embodiments where the user directly selects a between graphical element (i.e., the between graphical element is user-selected), the machine-selection(s) may or may not include a machine-selection of a transducer graphical element. In some embodiments, the first selection does not include a user-selected transducer graphical element. In some embodiments, including, but not limited to embodiments where the user directly selects a between graphical element, the selection of the at least one graphical element in the first graphical element set according to the instructions of block 710A is a selection, at one time, of each of the at least one graphical element in the first graphical element set. For example, the user directly selects, at one time, a between graphical element via a mouse click with the cursor above the between graphical element, which causes a corresponding machine selection, at one time, of the user-selected between graphical element, e.g., by changing a visual characteristic of the user-selected between graphical element. Although the above-discussion regarding block 710A includes examples involving both a user graphical element selection and a machine graphical element selection, some embodiments involve only a machine graphical element selection at block 710A.

Block 710B includes second selection instructions configured to cause selection (e.g., a second selection as opposed to the first selection discussed above with respect to block 710A) of at least one graphical element in a second graphical element set of the graphical element sets. In some embodiments, the second graphical element set is associated with a second one of the sets of two or more of the transducers whose respective transducers have been identified according to the instructions of block 707 to be not acceptable for concurrent selection, and the second selection instructions are configured to cause non-concurrent selection, in response to the selection of the at least one graphical element in the second graphical element set, of the respective transducers of the second one of the sets of two or more of the transducers. However, identification of the respective transducers as not acceptable for concurrent selection, and non-concurrent selection of the respective transducers are not required in some embodiments. In some embodiments, the selection of the at least one graphical element in the second graphical element set is a selection, over a time interval, of at least two of the graphical elements in the second graphical element set.

For example, a user might directly select a first transducer graphical element such as a first transducer graphical element 502 or 604 (i.e., the first transducer graphical element is a user-selected transducer graphical element), which might cause the second selection instructions to cause the data processing device system to (a1) perform a selection (or machine selection) of the user-selected first transducer graphical element (e.g., by changing its visual characteristics), and (b1) select the transducer corresponding to the user-selected first transducer graphical element. Then, the user might directly select a second transducer graphical element such as a second transducer graphical element 502 or 604 (i.e., the second transducer graphical element is a user-selected transducer graphical element), which might cause the second selection instructions to cause the data processing device system to (a2) perform a selection (or machine selection) of the user-selected second transducer graphical element (e.g., by changing its visual characteristics), and (b2) select the transducer corresponding to the user-selected second transducer graphical element. Accordingly, in some embodiments, the user-selections of the first and second transducer graphical elements over a time interval cause the corresponding machine-selections of the first and second transducer graphical elements over a time interval. In some embodiments, these machine selections (b1) and (b2) of the transducers corresponding to the user-selected first and second transducer graphical elements are non-concurrent selections. In some embodiments, the machine-based selections (b1) and (b2) of the transducers corresponding to the user-selected first and second transducer graphical elements may lead to an activation (or in some embodiments, a non-concurrent activation) of such transducers (e.g., block 712, discussed below).

In some embodiments, the second graphical element set selected according to the instructions of block 710B has a different number of graphical elements than the first graphical element set selected according to the instructions of block 710A. For example, the second graphical element set selected according to the instructions of block 710B could include two transducer graphical elements 502, while the first graphical element set selected according to the instructions of block 710A could include, in some embodiments, only a between graphical element 504 or, in other embodiments, two transducer graphical elements 502 and a between graphical element 504.

Block 712A shown in FIG. 7B includes activation instructions (e.g., instructions provided in a program) configured to cause activation of the transducers corresponding to the first graphical element set selected according to the instructions of block 710A. Block 712B shown in FIG. 7B includes activation instructions (e.g., instructions provided in a program) configured to cause activation of the transducers corresponding to the second graphical element set selected according to the instructions of block 710B.

In some embodiments, the activation instructions of block 712A include activation instructions configured to, in response to the concurrent selection of the respective transducers of the first one of the sets of two or more of the transducers cause concurrent activation, via the input-output device system (e.g., input-output device system 120 or 320), of each of the respective transducers of the first one of the sets of two or more of the transducers. In some embodiments, the concurrent activation may include monopolar activation of each of the respective transducers of the first one of the sets of two or more of the transducers. In some embodiments, the concurrent activation may include bipolar activation between the respective transducers of the first one of the sets of two or more of the transducers. The monopolar or bipolar activation of the respective transducers of the first one of the sets of two or more of the transducers may include sufficient energy being delivered from an energy source device system (e.g., energy source device system 340) to each of the respective transducers of the first one of the sets of two or more of the transducers, the energy sufficient to cause ablation of tissue in a bodily cavity. In some of these embodiments, conditions allow for the energy to be sufficient to cause an electrophysiological activity conduction block to be formed in the tissue between the respective transducers of the first one of the sets of two or more of the transducers.

In some embodiments, the activation instructions of block 712B include second activation instructions configured to, in response to the non-concurrent selection of the respective transducers of the second one of the sets of two or more of the transducers cause non-concurrent activation, via the input-output device system, of each of the respective transducers of the second one of the sets of two or more of the transducers. In some embodiments, the activation instructions of block 712B include second activation instructions configured to, in response to the non-concurrent selection of the respective transducers of the second one of the sets of two or more of the transducers, preclude bipolar activation, via the input-output device system, between the respective transducers of the second one of the sets of two or more of the transducers. In various embodiments, selection instructions (e.g., the selection instructions of block 808) allow for the concurrent selection of a pair of transducers by the selection of a particular between graphical element 504 made in accordance with various aspects of method 700.

In some embodiments associated with FIG. 7B, a first selection of at least one of the graphical elements 501 (e.g., between graphical element 504a shown in FIG. 5F, for example) from a first graphical element set is caused according to first selection instructions (e.g., instructions of block 710A) to select a first pair of transducers made up of a first transducer and a second transducer (e.g., transducers 306). FIG. 5F is considered to include a group of transducer graphical elements 502, and in some of these embodiments, the first selection may not include a user selection of any user-selected transducer graphical elements 502 in the group (e.g., the first selection could be for the between graphical element 504a in cases where the first selection is only for transducer pairs deemed to be concurrently selectable according to the instructions of block 707).

In some embodiments, a second selection of at least one of the graphical elements 501 in FIG. 5F is caused according to second selection instructions (e.g., instructions of block 710B) to select a second pair of the transducers made up of the first transducer and a third transducer. For example, in some embodiments, the second selection may not include a user selection of any user-selected transducer graphical elements 502 (e.g., the second selection could be for the between graphical element 504d in cases where the second selection is only for transducer pairs deemed to be concurrently selectable according to the instructions of block 707). In some embodiments, the second selection may not include a user selection of any user-selected between graphical elements 504 (e.g., the second selection could be for at least a selected transducer graphical element (e.g., transducer graphical element 502f shown in FIG. 5F) in cases where the second selection is only for transducer pairs deemed to be not-concurrently selectable according to the instructions of block 707). In various embodiments, each of the first, the second, and the third transducers are different transducers which respectively correspond to transducer graphical elements 502a, 502b and 502f. In various embodiments, each of the first pair of transducers and the second pair of transducers (each selected by respective ones of the first selection according to the instructions of block 710A and the second selection according to the instructions of block 710B, for example) is an adjacent pair of transducers in a distribution of transducers. In some embodiments, the second selection includes a selection of at least two transducer graphical elements in the group (e.g., transducer graphical elements 502f and 502a).

As stated above, a first spatial relationship between the plurality of transducer graphical elements 502 in the graphical representation of FIG. 5F, for example, may be consistent with a second spatial relationship between corresponding ones of the transducers in the distribution. In some embodiments, each of between graphical elements 504a and 504d is associated with a respective region of space that does not include a physical portion of a structure on which the transducers are located (e.g., structure 308). In other embodiments, at least one of the first pair and the second pair of transducers may correspond to a between graphical element 504 that is associated with a region of space that includes a physical portion of the structure. Such distinctions can be important, as discussed herein, in determining the acceptability of concurrency of selection of graphical elements and transducers, the acceptability of activation of transducers, the duration of activation, and for other reasons discussed herein.

As discussed above, the selections according to the instructions of blocks 710A and 710B can occur by way of any combination of one or more machine-based constituent selections and, optionally or additionally, user-based constituent selections. In some embodiments, each of the first selection (e.g., according to the instructions of block 710A) and the second selection (e.g., according to the instructions of block 710B) includes a user-selected graphical element 501 selected by a user according to a user instruction (e.g., a user-based constituent selection, as discussed above) to select the user-selected graphical element 501. In some embodiments, the first selection, the second selection, or each of the first selection and the second selection does not include a selection of a user-selected transducer graphical element 502 made in response to a user instruction to select the transducer graphical element. For instance, a user may instruct selection of a between graphical element 504, which can cause a machine-based selection of a pair of transducer graphical elements 502 that correspond to the user-selected between graphical element 504, and, optionally, a machine-based selection of a pair of transducers that correspond to the pair of transducer graphical elements 502. In some embodiments, the second selection does not include a selection of a user-selected transducer graphical element 502 made in response to a user instruction to select the transducer graphical element.

While in some embodiments, both the first selection (e.g., according to the instructions of block 710A) and the second selection (e.g., according to the instructions of block 710B) do not include a selection of a user-selected transducer graphical element made 502 in response to a user selection to select the user-selected transducer graphical element 502, in other embodiments, the second selection may include a selection of at least one user-selected between graphical element 504 (e.g., 504d) (e.g., made in response to a user-instruction to select the at least one user-selected between graphical element).

Block 710C shown in FIG. 7B includes third selection instructions employed in some embodiments, the third selection instructions configured to, in response to receiving a user instruction to select at least one user-selected graphical element, cause the data processing device system (e.g., data processing device system 110 or 310) to a select at least one other graphical element. In one particular embodiment, the third selection instructions are configured to cause the data processing device system to select at least a second graphical element (e.g., transducer graphical elements 502a and 502b) in response to a user instruction to select between graphical element 504a. In this particular embodiment, the third selection instructions are configured to select at least a third graphical element (e.g., transducer graphical elements 502a and 502o) in response to a user instruction to select the user-selected between graphical element 504d. Visual characteristics of user-selected graphical elements and graphical elements selected by the data processing device system in response to receiving a user instruction to select at least one user-selected graphical element may be changed as discussed above. In some embodiments, the first activation instructions of block 712A, the second activation instructions of block 712B or each of the first and the second activation instructions include instructions configured to cause activation of a corresponding one of the sets of two or more of the transducers in response to the selection of at least one graphical element made by the data processing device system in response to at least receiving a user instruction to select at least one user-selected graphical element.

Having discussed identifying the acceptability of concurrency of selection of transducer sets with respect to block 707 and corresponding subsequent selection of transducer graphical elements and activation of corresponding transducers pursuant to FIG. 7B, block 708 in FIG. 7A will now be described. Block 708 can include, in some embodiments, instructions provided by a program to cause the data processing device system to identify activation-ready transducers and not-activation-ready transducers based at least upon an analysis of transducer data (e.g., received according to the instructions of block 704). For example, in some embodiments, if the analysis of the transducer data indicates that certain transducers are located above an anatomical feature that should not be ablated, those certain transducers are identified according to the instructions of block 708 to be not-activation-ready transducers. Another example of not-activation-ready transducers includes those that have insufficient contact with tissue to properly ablate or acquire tissue characteristics, as determined, for example, according to measurements (e.g., various electrical, force, or pressure measurements) represented in the transducer data. The instructions according to block 708 include, in some embodiments, instructions configured to cause the graphical representation displayed according to the instructions of block 702 to visually distinguish the not-activation-ready transducers from the activation-ready transducers.

In this regard, block 708 includes, in some embodiments, instructions (e.g., identification instructions) provided by a program configured to cause the data processing device system to identify activation-ready transducers of the transducer-based device as transducers deemed, based at least on an analysis of the transducer data (e.g., received according to the instructions of block 704), acceptable for activation (e.g., activation according to the instructions of block 712), and not-activation-ready transducers of the transducer-based device as transducers deemed, based at least on the analysis of the transducer data, not acceptable for activation (e.g., activation according to the instructions of block 712).

Figure 8:
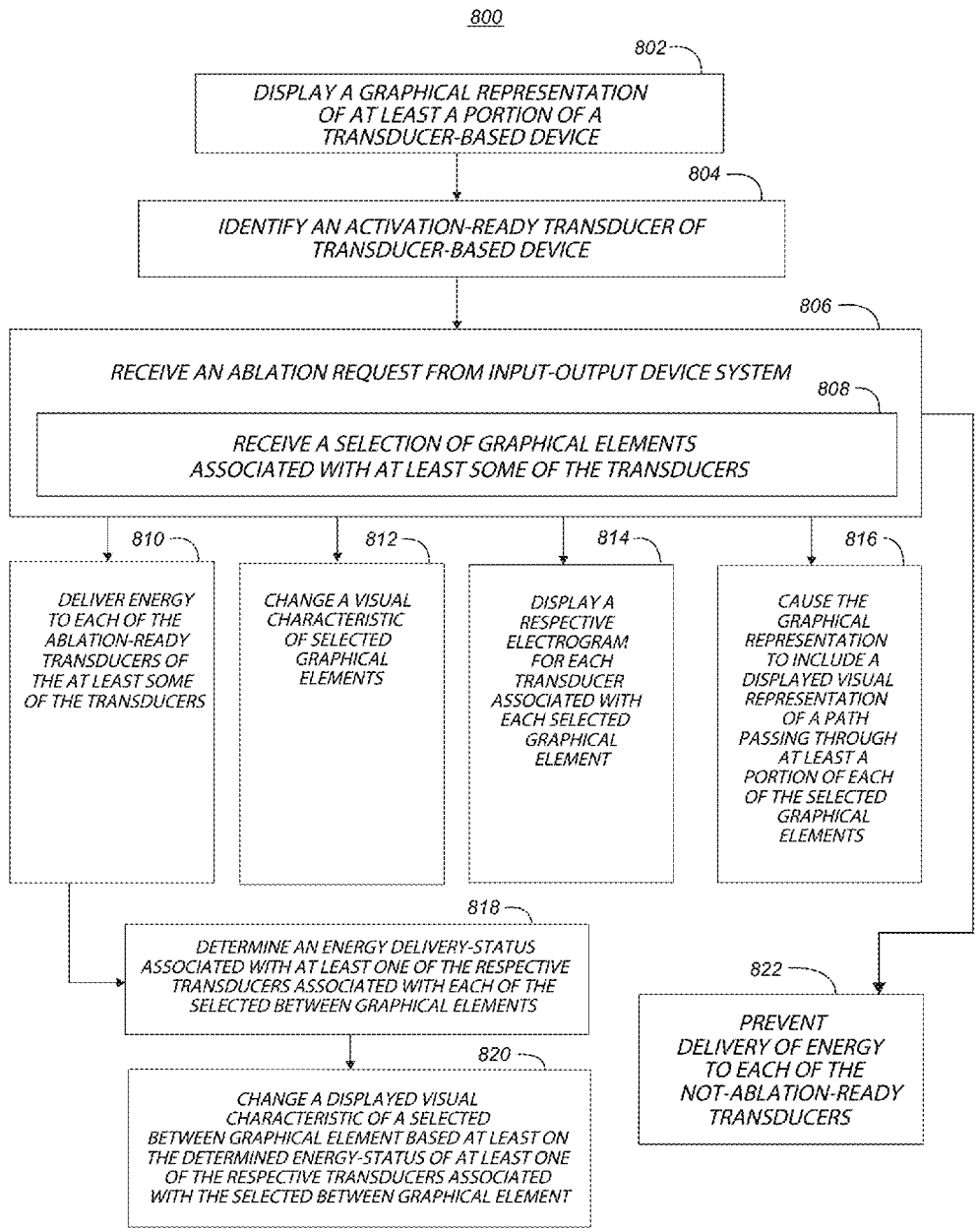
FIG. 8 illustrates a block diagram of a method for activating transducers of a transducer-based device according to various example embodiments.

As discussed above, the identification of activation-ready transducers and not-activation-ready transducers of a transducer-based device in accordance with the instructions of block 708 can take different forms. In this regard, block 804 in FIG. 8 provides an example of the instructions of block 708 in FIG. 7A, according to some embodiments. It should be noted that block 802 corresponds to block 702 in some embodiments, blocks 806 and 808 correspond to block 710 in some embodiments, and block 810 corresponds to block 712 in some embodiments. However, in some embodiments, FIG. 8 stands on its own independently of FIG. 7A. In this regard, the method 800 pertains to ablation-causing activations, although it is understood that other forms of activation may be employed in other embodiments. Reference to at least some of FIG. 5 continues with the discussion of FIG. 8 for convenience of discussion. In some embodiments, method 800, like method 700, may include a subset of the associated blocks or additional blocks than those shown. In addition, in some embodiments, method 800, like method 700, may include a different sequence between various ones of the associated blocks than those shown in FIG. 8.

The example of block 804, in some embodiments, includes instructions (e.g., identification instructions provided by a program) configured to identify an activation-ready transducer of the transducer-based device (e.g., transducer-based devices 100, 300, 400) as a transducer that is associated with or adjacent a region of space deemed, based at least on an analysis of the transducer data, acceptable for ablation. In some embodiments, this "adjacent region of space" is a region of space that includes matter that would be activated, ablated, or otherwise interacted with by the corresponding transducer due to ablation activation or other activation of the corresponding transducer. In some embodiments, a region of space is determined, in view of an analysis of the transducer data, to be acceptable for ablation or activation of a corresponding transducer set, when the region of space is not determined to be unacceptable for ablation or activation. In some embodiments, a region of space is determined, in view of an analysis of the transducer data, to be not acceptable for ablation or activation of a corresponding transducer set, when all or particular matter in the region of space may be negatively or unacceptably negatively impacted by the ablation or activation of the corresponding transducer set. In some embodiments, block 804 includes instructions (not shown, e.g., identification instructions provided by a program) configured to cause identification of an activation-ready transducer of the transducer-based device (e.g., transducer-based devices 100, 300, 400) as a transducer that is deemed, based at least on an analysis of the transducer data, to be located within sufficient proximity to a region of space, the sufficient proximity deemed acceptable for ablation. In some embodiments, this sufficient proximity is deemed to require contact between the transducer and the tissue to be ablated.

In some embodiments, block 804 also includes instructions (e.g., identification instructions provided by a program) configured to identify a not-activation-ready transducer of the transducer-based device as a transducer that is adjacent a region of space deemed, based at least on the analysis of the transducer data, not acceptable for ablation. In some embodiments, block 804 includes instructions (not shown, e.g., identification instructions provided by a program) configured to identify a not-activation-ready transducer of the transducer-based device (e.g., transducer-based devices 100, 300, 400) as a transducer that is deemed, based at least on an analysis of the transducer data, not within sufficient proximity to a region of space, the sufficient proximity deemed acceptable for ablation.

It is understood that a transducer may be identified as an activation-ready transducer or not-activation-ready transducer on the basis of other criteria in other embodiments. In some embodiments, activation-ready transducers are referred to as ablation-ready transducers and not-activation-ready transducers are referred to as not-ablation-ready transducers. In some embodiments, at least two of the ablation-ready transducers or at least two of the not-ablation-ready transducers may be located on a same structural member (e.g., an elongate member 304) of a transducer-based device. In some embodiments, at least two of the ablation-ready transducers or at least two of the not-ablation-ready transducers may be located on different structural members (e.g., different elongate members 304) of a transducer-based device. These differences can be important as transducers along a structural member may have different ablation characteristics than transducers located on different structural members that have no physical portion of the transducer based device between them. For example, ablation along structural members may have, for example, different insulating effects on ablation as compared to ablation between structural members.

In some embodiments where the transducer-based device or a portion thereof is receivable or positionable in a bodily cavity, the instructions of block 804 may include instructions configured to require that, in order for a region of space to be deemed acceptable for ablation, the region of space be determined, based at least on the analysis of the transducer data (e.g., received according to the instructions of block 704, which may be part of block 804 or between blocks 802 and 804 in some embodiments), to be associated with a tissue in the bodily cavity that is acceptable for ablation. The instructions of block 804 may include instructions configured to require that, in order for a region of space to be deemed not acceptable for ablation, the region of space be determined, based at least on the analysis of the transducer data, to be associated with a tissue in the bodily cavity that is not acceptable for ablation. In some embodiments, the bodily cavity is an intra-cardiac cavity and the tissue in the bodily cavity that is not acceptable for ablation is blood.

In some embodiments where the transducer-based device or a portion thereof is receivable or positionable in a bodily cavity, the instructions of block 804 may include instructions configured to require that, in order for a region of space to be deemed acceptable for ablation, the region of space be determined, based at least on the analysis of the transducer data, to be associated with an anatomical feature of the bodily cavity that is acceptable for ablation. The instructions of block 804 may include instructions configured to require that, in order for a region of space to be deemed not acceptable for ablation, the region of space be determined, based at least on the analysis of the transducer data, to be associated with an anatomical feature of the bodily cavity that is not acceptable for ablation (e.g., a pulmonary vein).

In some embodiments where the transducer-based device or a portion thereof is receivable or positionable in a bodily cavity that includes a tissue wall surface interrupted by one or more ports in fluid communication with the bodily cavity, the instructions of block 804 may include instructions configured to require that, in order for a region of space to be deemed not acceptable for ablation, the region of space be determined, based at least on the analysis of the transducer data, to overlie a least part of a port of the one or more ports.

Referring back to FIGS. 5C and 5D, the various regions 525 are associated with regions of space deemed not suitable or acceptable for ablation while various other regions of the graphical representation that exclude regions 525 are associated with regions of space deemed suitable for ablation in this illustrated embodiment. In some embodiments, like the above-discussion with respect to blocks 708 and 702, regions of space deemed suitable for ablation can be visually distinguished from the regions of space deemed not suitable for ablation in the graphical representation displayed according to the instructions of block 802. In this regard, the graphical representation instructions for visually distinguishing the regions of space deemed suitable for ablation from the regions of space deemed not suitable for ablation may reside in block 804 or in 802, according to some embodiments. In any event, these graphical representation instructions (e.g., graphical representation instructions included in a program) may be configured, in some embodiments, to cause an input-output device system (e.g., input-output device system 120 or 320) to display a graphical representation of at least a portion of a transducer-based device.

In some embodiments, like the above-discussion with respect to blocks 708 and 702, the graphical representation instructions may include instructions configured to cause the input-output device system to display the graphical elements 501 that are associated with transducer sets including the ablation-ready transducers with a first set of visual characteristics and to display the graphical elements 501 that are associated with transducer sets including the not-ablation-ready transducers with a second set of visual characteristics different than the first set of visual characteristics. In some embodiments, the first set of visual characteristics, the second set of visual characteristics, or both the first and the second sets of visual characteristics each includes a plurality of different visual characteristics. Different visual characteristics can include different colors, opacities, hues, intensities, shading, patterns, shapes or the addition or removal of any displayed information suitable for distinguishing an ablation-ready transducer from a not-ablation-ready transducer. In the embodiment of FIGS. 5C and 5D, transducer graphical elements 502 that are positioned over any of the regions 525 (e.g., transducer graphical elements 502 associated with not-ablation-ready transducers) are displayed with different visual characteristics (e.g., a thick line circle in this embodiment) than the transducers graphical elements 502 that are not positioned over any of the regions 525 (e.g., transducer graphical elements 502 associated with the ablation-ready transducers).

In the embodiment illustrated in FIGS. 5C and 5D, only the between graphical elements 504 that are each associated with a corresponding set of transducers (e.g., a corresponding pair of transducers in this embodiment) that includes only ablation-ready transducers are displayed. In the embodiment illustrated in FIGS. 5C and 5D, only the between graphical elements 504 that are each associated with a respective region of space that is located between a corresponding pair of transducers that includes only ablation-ready transducers are displayed. In the embodiment illustrated in FIGS. 5C and 5D, only the between graphical elements 504 that are each associated with a respective region of space that does not include any transducer and does not include any portion of a region of spaced deemed, based at least on the transducer data, not acceptable for ablation are displayed.

In the embodiment illustrated in FIGS. 5C and 5D, each of the between graphical elements 504 that is associated with a corresponding set of transducers (e.g., a corresponding pair of transducers in this embodiment) that includes at least one not-ablation-ready transducers is not displayed. In the embodiment illustrated in FIGS. 5C and 5D, each of the between graphical elements 504 that is associated with a region of space between a corresponding pair of transducers that includes at least one not-ablation-ready transducer is not displayed. In the embodiment illustrated in FIGS. 5C and 5D, each of the between graphical elements 504 that is associated with a region of space that does not include any transducer but does include a portion of a region of spaced deemed, based at least on the transducer data, not acceptable for ablation (e.g., a region 525) is not displayed.

Moving on to a discussion of blocks 806 and 808 in FIG. 8, which may correspond to block 710 in some embodiments, block 806 of method 800 includes ablation request instructions (e.g., instructions provided by a program) configured to cause the data processing device system (e.g., data processing device systems 110 or 310) to process an ablation request received from the input-output device system, the ablation request configured to request ablation by at least some of the plurality of transducers of the transducer-based device.

In some embodiments, the ablation request associated with block 806 may be considered part of a selection of one or more graphical elements according to the instructions of block 710 in FIG. 7A in some embodiments. Block 808 represents instructions associated with such a selection according to some embodiments. As discussed above, the selection instructions associated with block 710 may configure the data processing device system to receive a selection, via the input-output device system (e.g., again exemplified by input-output device system 120 or 320) of at least some of the graphical elements (e.g., graphical elements 501, 601) provided in the graphical representation. In some embodiments, the selection instructions associated with block 710 cause the data processing device system to receive, via the input-output device system, a selection of at least some of the graphical elements 501 associated with the transducers including activation-ready transducers. Block 808, in some embodiments, includes selection instructions (e.g., instructions provided in a program), which configure the data processing device system (e.g., again exemplified by data processing device systems 110 or 310) to cause selection of various graphical elements. In some embodiments, the caused selection includes receiving, via the input-output device system (e.g., again exemplified by input-output device systems 120, 320) a selection of the graphical elements 501 associated with at least some of the transducers, the at least some of the transducers including ablation-ready transducers. In some embodiments, each of the graphical elements 501 associated with the at least some of the transducers is independently selectable. For example, as shown in FIG. 5E, first between graphical element 504a positioned between the first and the second transducer graphical elements 502a, 502b respectively identified by identification labels 513 as "Q:6" and "R:6" has been selected via the input-output device system. In this example embodiment, the ablation request instructions of block 806 include the instructions of block 808. In this example embodiment, the ablation request associated with the instructions of block 806 is made at least in part by making a selection of the at least some of the graphical elements 501 associated with the instructions of block 808.

It is noted that in some embodiments (e.g., embodiments where ablation-ready transducers and not-ablation-ready transducers are selectable in accordance with blocks 806 or 808), the method 800 may include determination instructions (e.g., instructions provided by a program) (not shown, but could be shown connected (immediately) downstream of block 806 and (immediately) upstream of block 822) configured to cause the data processing device system to determine whether an ablation-requested transducer set including the at least some of the plurality of transducers selected in accordance with blocks 806 or 808 includes a not-ablation-ready transducer. In this case, the method 800 may include ablation denial instructions (e.g., instructions provided in a program) configured to, if it is determined according to the determination instructions that the ablation-requested transducer set includes the not-ablation-ready transducer, deny the ablation request. In some embodiments, the ablation denial instructions are configured to deny the ablation request at least with respect to the not-ablation-ready transducer in the ablation-requested transducer set if it is determined according to the determination instructions that the ablation-requested transducer set includes the not-ablation-ready transducer. In some embodiments, the ablation denial instructions can take a form of non-activation instructions (e.g., instructions provided by a program) associated with block 822 in FIG. 8, which, in some embodiments, are configured to cause the data processing device system to prevent energy from the energy source device system from being delivered to each of the plurality of not-ablation-ready transducers identified according to block 804 or block 708. An example of preventing energy from being delivered would be for the data processing device system to reject all or a portion of an instruction received, for example, from a user via the input-output device system, to perform ablation involving not-ablation ready transducers.

Block 812 of method 800 includes instructions (e.g., instructions provided in a program) configured to, in response to receiving independent selections of graphical elements in accordance with block 808, cause the input-output device system to change a visual characteristic of the selected graphical elements 501 during a time interval that occurs during the receiving of the independent selections, after a completion of the receiving of the independent selections, or both during the receiving of the independent selections and after a completion of the receiving of the independent selections. In some embodiments, the selected graphical elements 501 include a selected between graphical element 504a as shown in FIG. 5E. Changing the visual characteristic of the selected between graphical element 504a may include changing a color, opacity, hue, intensity, shading, pattern, shape or the addition or removal of any displayed information suitable for indicating that the selection has occurred. In this embodiment, the selected between graphical element 504a is modified to include an elongated graphical portion 530 having differing visual characteristics. In some embodiments, block 812 can include additional instructions configured to cause the input-output device system to change a visual characteristic of at least one (e.g., both in this illustrated embodiment) of the first and the second transducer graphical elements 502a, 502b respectively identified by identification labels 513 as "Q:6" and "R:6" during the time interval. In this example embodiment a thicker border is provided around each of the first and the second transducer graphical elements 502a, 502b upon receiving the selection.

In a similar fashion, a visual characteristics of others of the graphical elements 501 (e.g., including transducer graphical elements 502) may change upon their selection in accordance with the instructions of block 808. For example, as shown in FIG. 5F additional between graphical elements 504 (e.g., including second between graphical 504b) have been selected in accordance with the instructions of block 808 with the visual characteristics of the selected additional between graphical elements 504 changing in accordance with the instructions of block 812. For clarity, only the identification labels 513 associated with the transducer graphical elements 502 associated with the pair of transducers associated with each of the selected between graphical elements 504 is shown in FIGS. 5E and 5F. In this illustrated embodiment, each of the selected between graphical elements 504 in FIGS. 5E and 5F were independently selected.

It should be noted that, although the above discussion regarding changing of visual characteristics occurs within the context of FIG. 8, block 812, such discussion can also apply to any discussions herein regarding changing of visual characteristics in some embodiments.

Block 814 of method 800 includes instructions (e.g., instructions provided in a program) configured to cause the input-output device system to display a respective electrogram 535 (only two called out in each of FIGS. 5E and 5F) for each transducer of the pair of transducers associated with each of the selected between graphical elements 504 (e.g., selected according to the instructions of block 808 or 710). In this example embodiment, each electrogram 535 is identified with an identifier 536 that provides information corresponding to the identification label 513 associated with a respective one of the transducer graphical elements 502. In this example embodiment, each electrogram 535 is provided on the basis of transducer data provided by a transducer of the respective pair of transducers associated with a selected between graphical element 504. In this example embodiment, a single electrogram 535 would also be displayed if a transducer graphical element 502 were to be individually selected, the single electrogram 535 being provided on the basis of transducer data provided by the respective transducer associated with the selected single transducer graphical element 502. In some example embodiments, block 814 includes instructions configured to cause the input-output device system to display a combined electrogram (e.g., a bipolar electrogram) from the pair of transducers associated with each of the selected between graphical elements 504. It is noted that some of the electrograms 535 not shown in the graphical representation shown in FIG. 5F may be viewed by operation of scroll bar 528 via the input-output device system. It is also noted that, although block 814 is shown as immediately following an ablation request according to block 806, block 814, in some embodiments, is not dependent upon receipt of an ablation request, and may operate independently any time a graphical element is selected.

Block 816 of method 800 includes path-display instructions (e.g., instructions provided in a program) configured to, in response to receiving the independent selections (e.g., selected according to the instructions of block 808 or 710) of between graphical elements 504, cause the graphical representation to include a displayed visual representation of a path 537 passing through at least a portion of each of the selected between graphical elements 504, during a time interval that occurs (a) during the receiving of the independent selections, (b) after a completion of the receiving of the independent selections, or both (a) and (b). In this embodiment, the displayed visual representation of the path extends between at least two of the plurality of rows 510 and between at least two of the plurality of columns 512. In this embodiment, path 537 surrounds a region 525 (e.g., one of the regions 525c, which may represent a port interrupting a tissue wall of a bodily cavity). In this example embodiment, path 537 is a contiguous path. In this example embodiment, path 537 is a closed path. In this embodiment, the path display instructions of block 816 are further configured to cause the displayed visual representation of the path 537 to pass through at least some of the transducer graphical elements 502 associated with the transducers between which the regions of space associated with the selected between graphical elements 504 respectively reside. In some example embodiments (e.g., a visual or graphical representation (e.g., 600 in FIG. 6) provided by a graphical interface (e.g., FIG. 6)), the displayed visual representation of the path 537 includes a path segment that proceeds diagonally between a first node located at a first junction of a first one of the plurality of columns (e.g., columns 612) and a first one of the plurality of rows (e.g., rows 610) and a second node located at a second junction of a second one of the plurality of columns (e.g., columns 612) and a second one of the plurality of rows (e.g., rows 610), the first junction being different than the second junction. In this embodiment the path-display instructions of block 816 include instructions configured to cause the displayed graphical representation to change, during the time interval, a visual characteristic of the selected between graphical element 504 at least as part of forming the displayed visual representation of the path 537 (e.g., via elongated portion 530 in this embodiment). In this example embodiment, the path-display instructions of block 816 include instructions configured to cause the displayed graphical representation to change, during the time interval, a visual characteristic of at least some of the transducer graphical elements 502 associated with the transducers in the pairs of the transducers between which the regions of space associated with the selected between graphical elements 504 respectively reside. In some embodiments, the path 537 represents an ablation path or proposed or intended ablation path.

Block 810 of method 800 (which could represent a particular subset of implementations of block 712 in FIG. 7A in some embodiments) includes activation instructions (e.g., instructions provided in a program) configured to, in response to receiving the ablation request from the input-output device system, cause, via the input-output device system, energy from an energy source device system (e.g., energy source device system 340) to be delivered to each of the ablation-ready transducers of the at least some of the transducers in which ablation was requested by as per block 806, the activation instructions configured to cause the energy delivery to occur during the time interval. In this example embodiment, a selection of the control button 538 (called out in FIG. 5G) identified as "Ablate" in response to a user action via the input-output device system can cause execution of the activation instructions. In this example embodiment, the activation instructions of block 810 of method 800 include instructions (e.g., instructions provided in a program) configured to, in response to receiving the independent selections of between graphical elements 504 in accordance with selection instructions included in block 808, cause activation, via the input-output device system, of each of the pairs of the transducers between which the respective regions of space associated with the selected between graphical elements 504 respectively reside, the activation instructions configured to cause the activation to occur during the time interval. In this embodiment, the activation instructions include instructions configured to, in response to receiving the independent selections of the between graphical elements 504 cause energy from the energy source device system (e.g., energy source device system 340) to deliver energy to each of the pairs of the transducers between which the regions of space associated with the selected between graphical elements 504 respectively reside, the activation instructions configured to cause the energy delivery to occur during the time interval. In this example embodiment, the energy is tissue-ablation energy and the path 537 is representative of an ablation path. In some embodiments, the activation instructions include instructions configured to, in response to receiving the independent selections of the between graphical elements 504 cause monopolar activation of the transducers in each of the pairs of the transducers between which the regions of space associated with the selected between graphical elements 504 respectively reside, the activation instructions configured to cause the monopolar activation to occur during the time interval. In some embodiments, the activation instructions include instructions configured to, in response to receiving the independent selections of the between graphical elements 504 cause bipolar activation between the respective transducers in each of the pairs of the transducers between which the regions of space associated with the selected between graphical elements 504 respectively reside, the activation instructions configured to cause the bipolar activation to occur during the time interval. In this regard, the energy may be delivered in a manner that (a) a portion of the energy delivered to a first transducer of each pair of the transducers is transmitted by the first transducer, (b) a portion of the energy delivered to a second transducer of each pair of the transducers is transmitted by the second transducer, or both (a) and (b). In this regard, an indifferent electrode (e.g., 326) may be arranged to receive a portion of the energy delivered to at least one of the transducers of each of the pairs of the transducers between which the regions of space associated with the selected between graphical elements 504 respectively reside.

Figure 9:
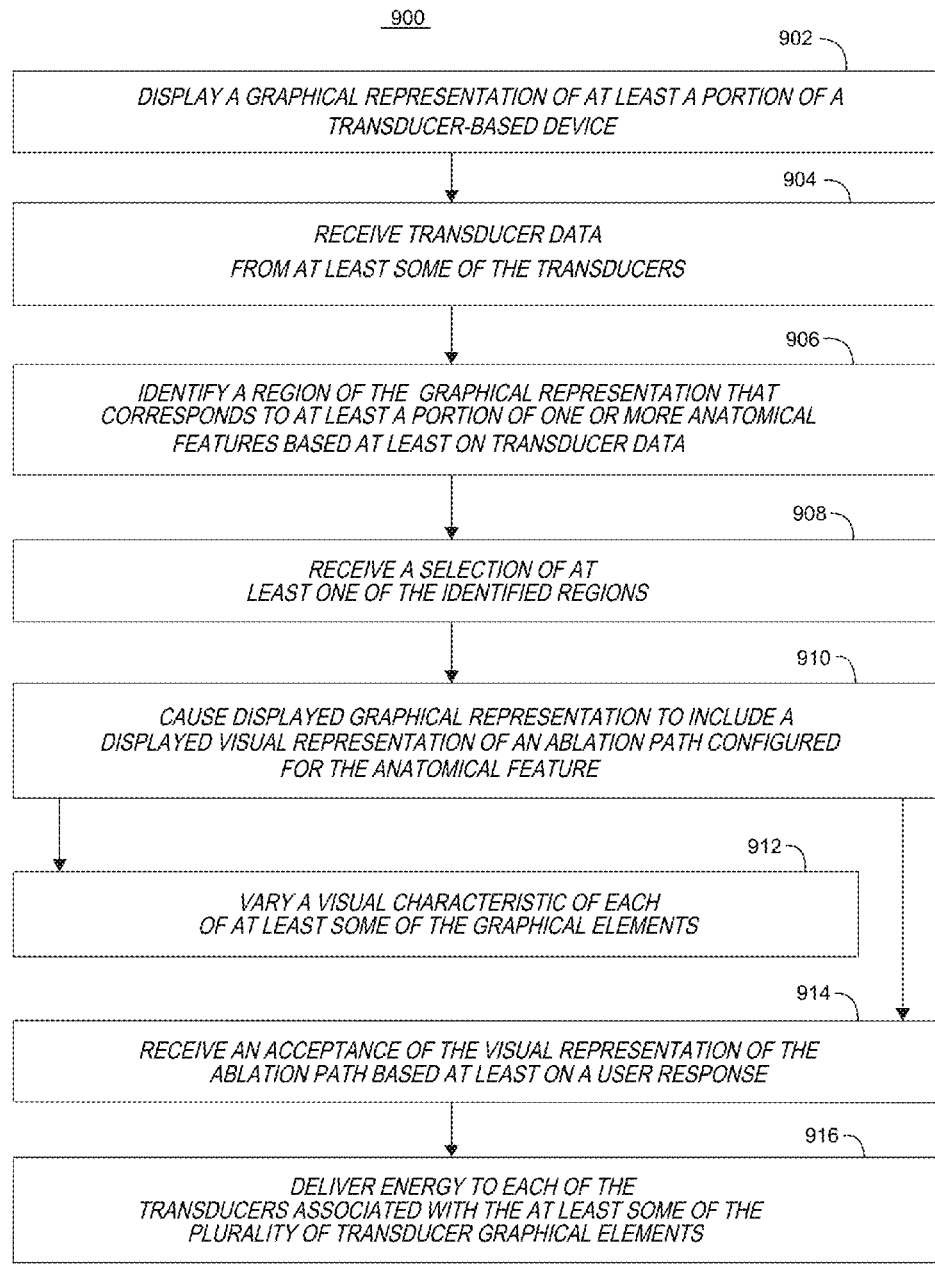
FIG. 9 illustrates a block diagram of a method for displaying a visual representation of an ablation path according to various example embodiments.

In some embodiments, selection of various graphical elements (e.g., graphical elements 501, 601) is not required to provide a visual representation of an ablation path (e.g., path 537). For example, FIG. 9 is a block diagram showing a method 900 including instructions (e.g., instructions provided in a program) for displaying a visual representation of an ablation path. Reference to the instructions provided by at least some of the blocks associated with method 700 is made for comparison purposes. Reference to various ones of FIG. 5 including transducer graphical elements 502 and between graphical elements 504 continues to be made for convenience of discussion. In some embodiments, method 900 may include a subset of the associated blocks or additional blocks than those shown in the FIG. 9. In some embodiments, method 900 may include a different sequence between various ones of the associated blocks than those shown in FIG. 9.

In a manner similar to block 702, block 902 of method 900 includes instructions (e.g., graphical representation instructions or graphical interface instructions included in a program) configured to cause an input-output device system (e.g., input-output device system 120 or 320) to display a graphical representation of at least a portion of a transducer-based device (e.g., transducer-based devices 200, 300, or 400). FIG. 5A illustrates a graphical interface provided by the input-output device system according to one example embodiment provided in accordance with block 902. The graphical interface of FIG. 5A includes a graphical representation 500 that includes a plurality of transducer graphical elements 502 and a plurality of between graphical elements 504, each characterized as per above. In a manner similar to block 704, block 904 of method 900 includes instructions (e.g., input instructions included in a program) that cause the data processing device system (e.g., data processing device systems 110 or 310) to receive transducer data from at least some of the transducers via the input-output device system.

In a manner similar to block 706, block 906 of method 900 includes instructions (e.g., identification instructions included in a program) that are configured to identify a region of the graphical representation that corresponds to at least a portion of one or more anatomical features based at least on the transducer data. In this example embodiment, a plurality of identified regions 525 is shown in the three-dimensional graphical representation provided by the graphical representation 500 of FIG. 5C and the two-dimensional graphical representation provided by the graphical representation 500 of FIG. 5D, each of the identified regions corresponding to a particular anatomical feature as previously discussed (e.g., ports related to various pulmonary veins, left lateral appendage and mitral valve).

Block 908 of method 900 includes selection instructions (e.g., instructions provided in a program) configured to cause the data processing device system (e.g., data processing device systems 110 or 310) to receive a selection from the input-output device system of at least one of the identified regions 525. Block 910 of method 900 includes path-display instructions (e.g., instructions provided in a program) configured to, in response to receiving the selection of the at least one of the identified regions, causes the displayed graphical representation to include a displayed visual representation of an ablation path configured for the anatomical feature.

Referring to FIG. 5D, a region 525 (e.g., region 525c) corresponding to a pulmonary vein of the left pulmonary vein group has been selected via the input-output device system. Again, various input-output device system components including a touch screen, keyboard or computer mouse may be employed to make the selection by way of non-limiting example. A path 537 defining an ablation path around the selected region 525c is automatically generated in response to the selection of region 525c in accordance with the path display instructions of block 910.

Unlike the embodiment of FIG. 8, where an ablation path is defined by a user, the ablation path associated with the embodiment of FIG. 9 is defined by the data-processing device system. This can be accomplished in various ways. In this example embodiment, transducer data from the transducer-based device is used to help define each of the particular regions 525 as well as additional regions other than the regions 525 that can accommodate an ablation path configured for the anatomical feature corresponding to a selected region. In this example embodiment, the visual representation of the ablation path (e.g., represented by path 537) passes at least proximate to each of at least some the transducer graphical elements 502 associated with the transducers associated with the particular ones of the additional regions positioned at least proximate region 525c. In some example embodiments, the visual representation of the ablation path passes at least proximate to each of at least some of the between graphical elements 504 (e.g., through the between graphical elements 504 in this embodiment) associated with pairs of the transducers associated with the particular ones of the additional regions positioned at least proximate region 525c. In some example embodiments, at least some of the transducers are deemed anatomical feature-specific transducers (e.g., transducers associated with a particular one of the anatomical features) based at least on the transducer data while others of the transducers are deemed not-anatomical feature-specific transducers (e.g., transducers not associated with a particular one of the anatomical features) based at least on the transducer data. In various example embodiments, method 900 includes instructions (not shown) (e.g., instructions provided in a program) configured to cause the data processing device system to determine the ablation path based at least on a determination of a proximity of various ones of the not-anatomical feature-specific transducers to various ones of the anatomical feature-specific features associated with an anatomical feature corresponding to selected region 525. In some of these various example embodiments, the path-display instructions of block 910 includes instructions configured to, in response to receiving the selection of the at least one of the identified regions, cause the displayed graphical representation to include the displayed visual representation of an ablation path configured for the anatomical feature based at least on (a) an identification of the transducer graphical elements 502 associated with the various ones of the not-anatomical feature-specific transducers, (b) an identification of the between graphical elements 504 associated with pairs of the various ones of the not-anatomical feature-specific transducers, or both (a) and (b).

In this example embodiment, the path-display instructions are configured to, in response to receiving the selection of the identified region 525c, cause the displayed visual representation of the ablation path to surround the identified region 525c. In this example embodiment, the path-display instructions are configured to, in response to receiving the selection of the identified region 525c, cause the displayed visual representation of the ablation path to continuously surround the identified region 525c. In some example embodiments, the respective ablation paths associated with different ones of at least two selected ones of the identified regions 525 may have different configurations (e.g., shape, continuity). In some example embodiments, the transducer data includes data associated with an electrical characteristic (e.g., impedance) of tissue within a bodily cavity in which the transducer based-device or a portion thereof is receivable or positionable. In some example embodiments, the transducer data includes data associated with a flow characteristic of fluid within a bodily cavity in which the transducer-based device or a portion thereof is receivable or positionable.

In this example embodiment, block 912 of method 900 includes instructions (e.g., instructions provided in a program) configured to, in response to receiving the selection of the identified region 525, cause the input-output device system to vary a visual characteristic of each of at least some of the graphical elements 501. In this example embodiment, a visual characteristic of each of at least some of the transducer graphical elements 502 and each of at least some of the between graphical elements 504 is changed.

In this example embodiment, block 914 of method 900 includes path-acceptance instructions (e.g., instructions provided in a program) configured to cause the data processing device system to receive an acceptance of the visual representation of the ablation path based at least on a user response via the input-output device system.

In this example embodiment, block 916 of method 900 includes activation instructions (e.g., instructions provided in a program) configured to, in response to receiving the acceptance, cause, via the input-output device system, energy from an energy source device system (e.g., energy source device system 340) to be delivered to each of the transducers associated with the at least some of the plurality of transducer graphical elements 502, the energy sufficient for ablating tissue. Ablation can include monopolar ablation, or bipolar ablation or combinations thereof.

Figure 10:
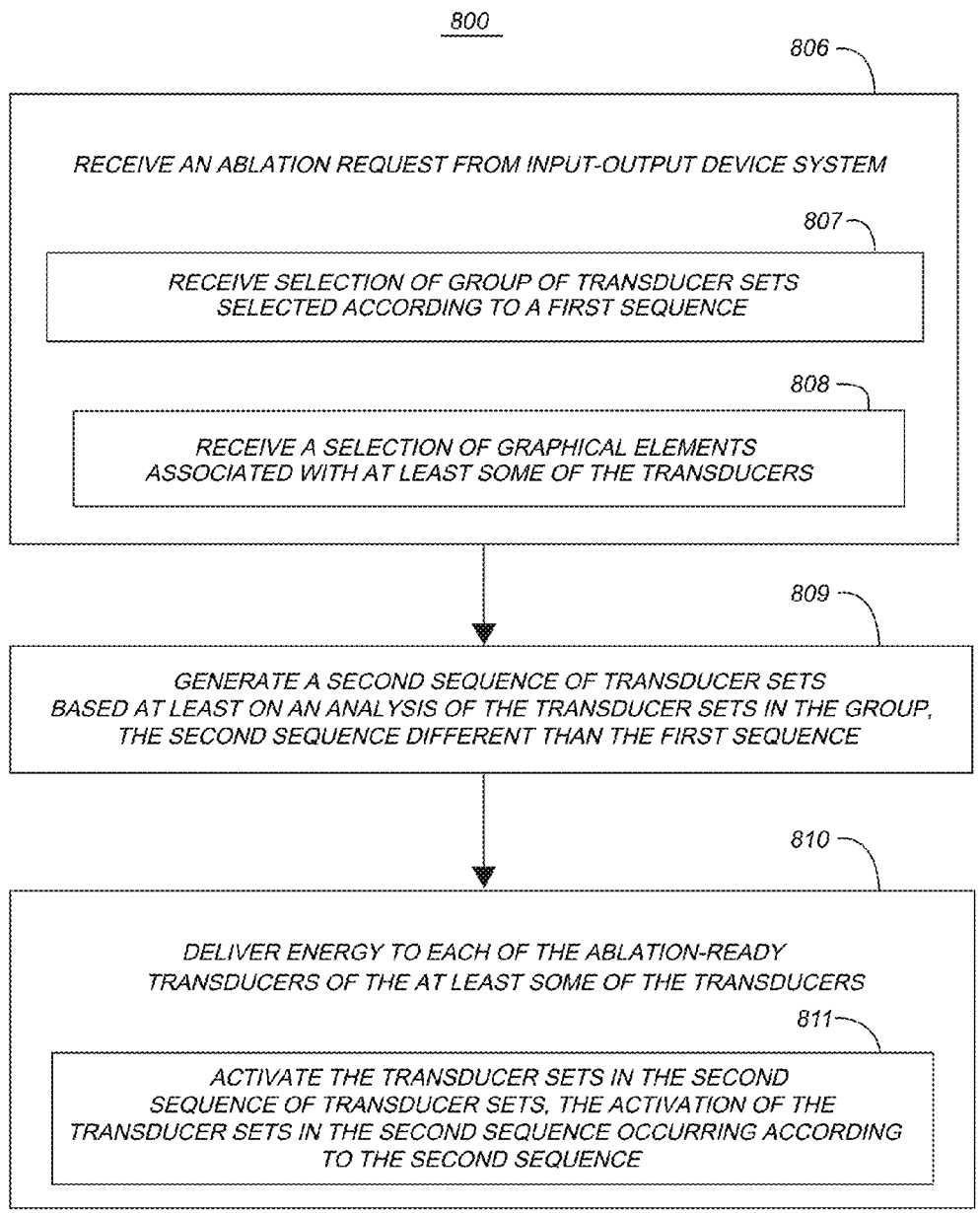
FIG. 10 illustrates an exploded view of some of the blocks of the block diagram of FIG. 8, according to some example embodiments.

FIG. 10 is an exploded view of the blocks 806 and 810 of a version of method 800 according to some example embodiments. In some embodiments, the ablation request instructions of block 806 include instructions (e.g., reception instructions provided in a program) as per block 807 configured to receive a selection from the input-output device system of a group of transducer sets, each of the sets of the group of the transducer sets including at least one of the transducers of the transducer-based device (e.g., transducer-based devices 200, 300, or 400). In these embodiments, each of the transducer sets is selected according to a first sequence. In some embodiments, at least part of the selection according to block 807 occurs by a selection of graphical elements, such that the instructions of block 808 are configured to cause the data processing device system (e.g., again exemplified by data processing device systems 110 or 310) to receive, via the input-output device system (e.g., again exemplified by input-output device systems 120, 320) a selection of at least some of the graphical elements 501 associated with some or all of the plurality of transducer sets discussed above with respect to block 807. In some example embodiments, each of the transducer graphical elements 502 associated with the plurality of transducer sets is selected according to the first sequence. For example, as shown in FIG. 5F, the transducer graphical elements 502 associated with path 537 may be selected in a sequential fashion in the following order (e.g., each selected transducer graphical element 502 indicated by the corresponding identification labels 513: "R:6", "Q:6", "P:6", "P:7" "O:7" "O:8", "O:9", "P:9", "P:10", "Q:10", "R:10", "R:9", "S:9", "S:8", "S:7", and "R:7" to select the plurality of transducer sets according to the first sequence. In such embodiments, each transducer set may be considered to have a single transducer. Also, as shown in FIG. 5F, the between graphical elements 504 associated with path 537 may be selected in a sequential fashion in the following order (e.g., each selected between graphical element 504 herein identified by the corresponding pair of identification labels 513 associated with the transducer graphical elements 502 in which the selected between graphical element 504 is positioned between): "R:6-Q:6", "Q:6-P:6", "P:6-P:7", "P:7-O:7", "O:7-O:8", "O:8-O:9", "O:9-P:9", "P:9-P:10", "P:10-Q:10", "Q:10-R:10", "R:10-R:9", "R:9-S:9", "S:9-S:8", "S:8-S:7", "S:7-R:7" and "R:7-R:6" to select the plurality of transducer sets according to the first sequence. In such embodiments, each transducer set may be considered to have at least two transducers. In this embodiment, each of the selected between graphical elements 504 is associated with a region of space between a pair of transducers that include the respective first and second transducers which make up a respective set of group of transducer sets. It is noted that the first sequence can take other forms in other embodiments. For example, the transducer sets may be selected randomly or pseudo-randomly according to the first sequence. In other embodiments, the first sequence may not require successively adjacent transducers in a distribution of the transducers to be selected as described above.

In various embodiments, each of the transducer sets in the first sequence form part of a group of the transducer sets. In various embodiments, various transducer sets in a group of transducer sets are selected according to a first sequence (e.g., the first sequence described above with regard to block 807) with at least two of the transducer sets in the group sequentially selected. In accordance with the discussion above, in at least some of these various embodiments, each of at least some of the selected transducer sets in the group includes at least one transducer different than each of the other transducer sets in the group. In at least some of these various embodiments, each of at least some of the transducer sets in the group includes at least two transducers. In at least some of these various embodiments, each of at least some of the transducer sets in the group includes a respective pair of adjacent ones of the transducers in a distribution of the transducers. The respective pair of adjacent ones of the transducers of each of the at least some of the transducer sets in the group may have a same transducer as the respective pair of adjacent ones of the transducers of another of the at least some of the of the transducer sets in the group. In some of these various embodiments, at least a first transducer set in the group has a same transducer as a second transducer set in the group. In at least some of these various embodiments, two or more of the transducers in a given one of the transducer sets may be selected concurrently (e.g., a pair of transducers selected by a selection of a between graphical element 504, 604 as described above). In at least some of these various embodiments, two or more of the transducer sets in the group may also be selected concurrently in the first sequence. In at least some of these various embodiments, an additional transducer set may be selected concurrently with one of the at least two of the transducer sets sequentially selected according to the first sequence. Transducer sets in the group that include different numbers of transducers or different transducers may be selected according to the first sequence. For example, the first sequence may indicate at least (a) a selection (e.g., by a selection of a transducer graphical element 502, 602) of a first transducer in a first transducer set in the group followed by a selection (e.g., by a selection of a between graphical element 504, 604) of a pair of second and third transducers in a second transducer set in the group, (b) a selection (e.g., by a selection of a between graphical element 504, 604) of a pair of fourth and fifth transducers in a third transducer set in the group followed by a selection (e.g., by a selection of a transducer graphical element 502, 602) of a sixth transducer in a fourth transducer set in the group, or both (a) and (b).

In some embodiments, the activation instructions of block 810 of method 800 includes activation instructions as per block 811 (e.g., instructions provided in a program) configured to cause sequential activation, initiated during or after completion of a generation of a second sequence of transducer sets (discussed below), of the transducer sets in the second sequence of transducer sets. The activation of the transducer sets in the second sequence occurs according to the second sequence, and the activation instructions are configured to cause activation of at least one transducer in each of the sequentially activated sets. In one particular embodiment, the activation of instructions of block 811 are configured to cause activation of the transducer sets of a group of transducer sets according to a second sequence different than the first sequence in which the transducer sets of the group of transducers sets were selected.

The second sequence may be determined in various manners. For example, in some embodiments, method 800 may include a block 809 (e.g., shown in FIG. 10, not shown in FIG. 8) that includes generation instructions (e.g., instructions provided in a program) configured to, in response to receiving at least part of the first sequence, cause a generation (e.g., via a data processing device system such as data processing device systems 110 or 310) of the second sequence of transducer sets based at least on an analysis of the transducer sets in a group that the transducer sets in the first sequence form part of. Accordingly, in some embodiments, the selection of the transducer sets according to the first sequence may include user-based selections, and the generation of the second sequence may be machine-performed (e.g., via a data processing device system such as data processing device systems 110 or 310) involving machine-based selections. The generation of the second sequence can be initiated in response to receiving part of the first sequence, such that generation of the second sequence is initiated during the receiving of the first sequence. Or, the generation of the second sequence can be initiated after receiving the entirety of the first sequence. Some examples of the analysis of the transducer sets in the group, upon which the generation of the second sequence of transducer sets can be based, are described below with respect to at least FIGS. 11-16 and any other embodiment in which a transducer-activation sequence is generated based at least on an analysis of transducer sets or data associated with transducer sets identified in a transducer-selection sequence and, consequently, the transducer-activation sequence might be different than the transducer-selection sequence (although the invention is not limited to these examples). In some embodiments, the transducer sets in the second sequence include all or only the transducers in the group of transducers sets selected in accordance with the first sequence.

In various embodiments, ablation request instructions (e.g., instructions provided by block 806) include reception instructions (e.g., provided in a program) (not shown in the Figures) configured to receive a selection of a path (e.g., path 537 in FIG. 5F) along which tissue of a bodily cavity (e.g., an intra-cardiac cavity) is to be ablated by various transducers. The selection may include an indication of a first order of transducer sets along the path, each of transducer sets in the first order including at least one transducer (e.g., identified by transducer graphical elements 502: "R:6", "Q:6", "P:6", "P:7", "O:7", "O:8", "O:9", "P:9", "P:10", "Q:10", "R:10", "R:9", "S:9", "S:8", "S:7", and "R:7" in FIG. 5F). In at least some of these various embodiments, at least some of the transducer sets in the first order include two or more transducers (e.g., pairs of transducers associated with between graphical elements 504: "R:6-Q:6" "Q:6-P:6", "P:6-P:7" "P:7-O:7" "O:7-O:8", "O:8-O:9", "O:9-P:9", "P:9-P:10", "P:10-Q:10", "Q:10-R:10", "R:10-R:9", "R:9-S:9", "S:9-S:8", "S:8-S:7", "S:7-R:7" and "R:7-R:6" in FIG. 5F). In at least some of these various embodiments, at least some of the transducer sets in the first order include a respective pair of adjacent transducers in a distribution of the transducers. Several respective pairs of adjacent transducers may include a same transducer in the distribution (e.g., pairs of transducers associated with between graphical elements 504: "S:9-S:8", "S:8-S:7"). In at least some of these various embodiments, at least some of the transducer sets in the first order include at least one different transducer than each of the other transducer sets in the first order. In at least some of these various embodiments, two or more of the transducer sets in the first order are sequentially selected. Sequential selection of the two or more of the transducer sets in the first order may occur in various ways including those previously described in this detailed description by way of non-limiting example. In at least some of these various embodiments, an additional transducer set may be selected concurrently with one of the two or more sequentially selected transducer sets. In at least some of these various embodiments, two or more of the transducer sets in the first order may be concurrently selected. For example, in some embodiments associated with method 900, all of the transducer sets associated with a particular ablation path may be concurrently selected by an acceptance of the visual representation of the path based at least on a user response via an input-output device system in accordance with the instructions of block 914.

Generation instructions (not shown in the Figures, but similar to the generation instructions associated with block 809) may be configured to, in response to receiving at least part of the selection of the ablation path (e.g., path 537), cause generation of a second order of transducer sets different than the first order based at least on an analysis of the transducer sets in the first order. In this regard, the generation of the second order can be initiated in response to receiving part of the selection of the ablation path, such that it is initiated during the receiving of the selection of the ablation path. Or, the generation of the second order can be initiated after receiving the entirety of the selection of the ablation path. Like the above-discussion with respect to block 809, FIGS. 11-16 and other embodiments provide some examples of the analysis of the transducer sets in the first order, upon which the generation of the second order of transducer sets can be based (although the invention is not limited to these examples). The transducer sets in the second order may include all the transducers in the first order. In some embodiments, the transducer sets in the second order may collectively only include transducers in the first order. Activation instructions (not shown in the Figures, but similar to the activation instructions associated with block 811) can be provided, which are configured to cause ablation, initiated during or after completion of the generation of the second order according to generation instructions, of the selected ablation path at least by ablation-activating transducers in the second order according to the second order with at least two of the ablation-activating transducers in the second order activated sequentially. In some embodiments, the ablation-activating transducers in the second order do not include any transducers not present in the second order. In some embodiments, the ablation-activating transducers in the second order include all or only the transducers in the first order.

In regard to the analysis that might lead to the above-discussed generation of the second sequence or second order based on an analysis of transducer sets in the respective first sequence and first order, situations may arise that make it undesirable to activate various transducer sets in a group concurrently, and at least two of the transducer sets in the group may, therefore, need to be activated sequentially or a delay between the activation of at least two of the transducer sets in the group may be required. Consequently, if the first sequence or first order includes these various transducer sets in the group, the second sequence or second order could be generated according to some embodiments to indicate an activation sequence or order that does not activate such various transducer sets in the group concurrently.

Figure 11:
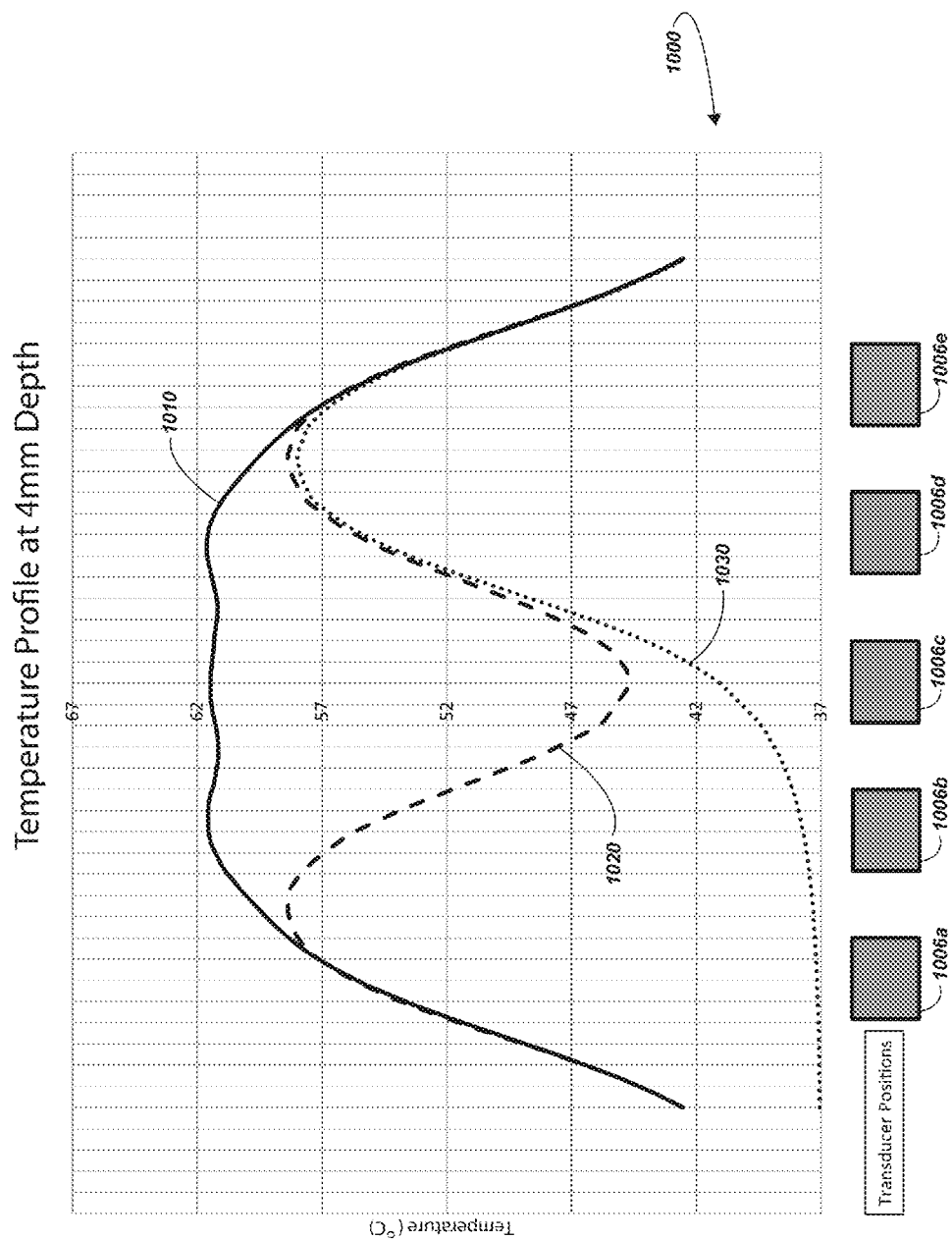
FIG. 11 illustrates a graph that compares (a) a temperature profile associated with concurrent activation of five transducers, (b) a temperature profile associated with concurrent activation of two pairs of adjacent transducers, the two pairs of adjacent transducers separated by a non-activated transducer, and (c) activation of a single pair of transducers.

For example, FIG. 11 is a graph 1000 that compares (a) a temperature profile 1010 associated with concurrent activation of five transducers 1006a, 1006b, 1006c, 1006d and 1006e (collectively transducers 1006), (b) a temperature profile 1020 associated with concurrent activation of two pairs of adjacent transducers 1006 (e.g., a pair of transducers 1006a, 1006b and a pair of transducers 1006d, 1006e), the two pairs of adjacent transducers separated by a non-activated transducer (e.g., transducer 1006c), and (c) activation of a single pair of transducers (e.g., a pair of transducers 1006d, 1006e). Each temperature profile was generated using data generated by Multiphysics® 4.1, Version 4.1.0.88 software provided by Comsol Inc. Each of the temperature profiles 1010, 1020 and 1030 is associated with a four millimeter tissue ablation depth. Various activated pairs of adjacent transducers are modeled with bipolar activation conditions. Temperature profile 1020 indicates that leaving at least one transducer between concurrent bipolar activation of the two transducer pairs results in a temperature profile having a maximum temperature similar to a maximum temperature provided by bipolar activation of the single transducer pair associated with temperature profile 1030. This contrasts with the much higher maximum temperature with the concurrent activation of the five electrodes 1006. Graph 1000 implies that ablation temperatures are higher in the absence of "at least a one-transducer gap" between two concurrently bipolar activated pairs of the transducers, whereas with the presence of the at least one transducer gap, the maximum temperature of each of the two concurrently bipolar activated transducer pairs is substantially similar to the maximum temperature associated with the bipolar activation of a single transducer pair. Graph 1000 implies that "at least a one-transducer gap" separating the concurrently bipolar activated transducer pairs allows each of the separated transducer pairs to be treated relatively independently of one another. This independence may advantageously lead to more consistent and uniform ablated regions being associated with each of the separated transducer pairs. This independence may advantageously lead to the use of more uniform operating parameters for each of the separated transducer pairs.

It should be noted that the reference to the "at least one-transducer gap", above, may be a function of the distance between transducers. Accordingly, FIG. 11 can be viewed from the standpoint that a sufficient distance between transducer sets (e.g., pairs of transducers) may be required in order to concurrently activate transducer sets within this distance. If this sufficient distance is not met between two transducer sets indicated in the first sequence or first order discussed above, the second sequence or second order could be generated according to some embodiments to ensure that these two transducers sets are not concurrently activated.

It should also be noted that the "at least one-transducer gap", above, need not only be applied to the context where a first sequence or first order of transducer sets is selected, and can apply anytime a transducer-set-activation schedule is generated from a pool of transducer sets.

Figure 12:
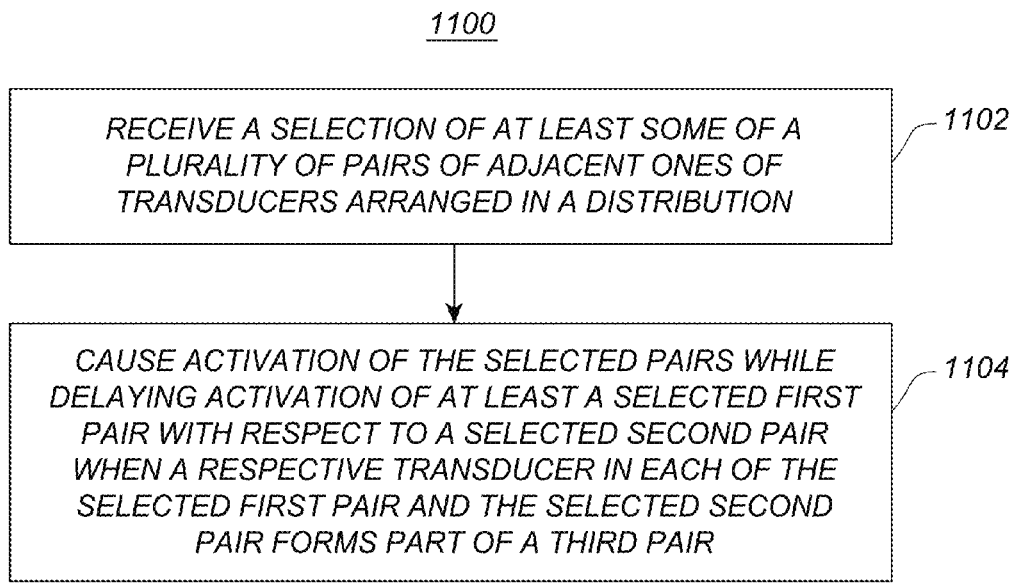
FIG. 12 illustrates a block diagram of a method for activating transducers of a transducer-based device according to various example embodiments.

FIG. 12 is a block diagram showing a method 1100 including instructions provided by various blocks (e.g., instructions provided in a program) for selecting and activating transducers in a transducer-based device such as transducer-based device 300 according to an example embodiment. In some embodiments, method 1100 may include a subset of the associated blocks or additional blocks than those shown in FIG. 12.

Block 1102 includes selection instructions configured to cause a reception from an input-output device system (e.g., input-output device system 120 or 320) of a selection of at least some of a plurality of pairs of adjacent ones of the transducers arranged in a distribution by a transducer-based device (e.g., transducers 306 shown in FIG. 3B). Reference is herein made to the transducers 306 for convenience and it is understood that other transducer-based devices employing other transducers may be employed in other embodiments employing aspects of method 1200.

In one example embodiment, a first pair of the transducers 306 and a second pair of the transducers 306 is selected. This selection could be according to the above-discussed first sequence or first order, in some embodiments. Block 1104 includes activation instructions configured to cause activation of the selected at least some of the plurality of adjacent ones of the transducers 306 in the distribution, subject to delay instructions configured to cause a delay in the activation of the first pair of adjacent ones of the transducers 306 in the distribution with respect to a starting of the activation of the second pair of adjacent ones of the transducers 306 in the distribution in response to a circumstance where a respective transducer in each of the first and the second pairs of adjacent ones of the transducers 306 forms part of a third pair of adjacent ones of the transducers 306 in the distribution.

For example, in FIG. 3B, transducer-based device 300 includes transducers 306d, 306e, 306f, 306g and 306h located on a same elongate member 304 and arranged along a path extending between the proximal and distal ends (307, 305, not called out in FIG. 3B) of the elongate member 304. If the first pair of adjacent transducers 306 selected includes transducers 306d and 306e and the second pair of adjacent transducers 306 includes transducers 306f and 306g, then activation of transducers 306d, 306e forming the first pair of adjacent transducers 306 could be delayed with respect to a starting of the activation of transducers 306f, 306g forming the second pair of adjacent transducers 306 since, in accordance with the instructions of block 1104, a respective transducer in the first pair of adjacent transducers 306 (e.g., transducer 306e) and a respective transducer in the second pair of transducers 306 (e.g., transducer 306f) forms part of a third pair of adjacent ones of transducers 306 in the distribution. If the second pair of adjacent transducers 306, instead, includes transducers 306g and 306h, then activation of transducers 306d, 306e forming the first pair of adjacent transducers 306 would not be delayed, according to these embodiments, with respect to a starting of the activation of transducers 306g, 306h forming the second pair of adjacent transducers 306, because no respective transducer in each of the first pair of adjacent transducers 306 and the second pair of adjacent transducers 306 forms part of third pair of adjacent ones of transducers 306 in the distribution.

In various embodiments, activation in accordance with method 1100 can ensure the above-discussed "at least one-transducer gap" and, therefore, may allow each of the selected transducer pairs to be treated independently of one another in ablation activation embodiments and may lead to more consistent and uniform ablated regions or the use of more uniform operating parameters as discussed above. In addition, in some embodiments, an activation sequence or order, which may be the above-discussed second sequence or second order, respectively, may be generated based on an analysis of transducer sets in an initial transducer-selection sequence or order, which may be the above-discussed first sequence or first order, respectively, according to the delay instructions associated with block 1104. For example, in some embodiments, a user might initially select a sequence of the following four transducers sets, each set including a single transducer: 306d, 306e, 306f, and 306g (e.g., FIG. 3B), where transducers 306d and 306e may, in some embodiments, be considered a selected pair pursuant to block 1102 in FIG. 12, and transducers 306f and 306g may be considered another selected pair pursuant to block 1102. In this example, a generated activation sequence might indicate a transducer set of transducers 306f-306g, followed by a transducer set of transducers 306d-306e, where both of transducers 306f and 306g are to be activated concurrently, and both of transducers 306d-306e are to be activated concurrently in a delayed manner with respect to the concurrent activation of transducers 306f and 306g, pursuant to block 1104.

In some embodiments, each of the transducers 306 in the first pair of adjacent ones of the transducers 306 according to block 1104 is different than each of the transducers 306 in the second pair of adjacent ones of the transducers 306 according to block 1104. In some embodiments, each of the first and the second pairs of adjacent ones of the transducers 306 share a same transducer 306. For example, the first pair might include transducers 602b and 602c in FIG. 6, while the second pair might include transducers 602b and 602a, and the third pair might include transducers 602c and 602a.

It is noted that in various embodiments, method 1100 may be employed not only with pairs of adjacent ones of the transducers located on a same elongate member 304 but may be employed with transducer pairs located on different elongate members 304. For example, if the selected first pair of adjacent transducers 306 includes transducers 306d and 306i, and the selected second pair of adjacent transducers 306 includes transducers 306j and 306k, then activation of transducers 306d, 306i forming the first pair of adjacent transducers 306 may be delayed with respect to a starting of the activation of transducers 306j, 306k forming the second pair of adjacent transducers 306 since, in accordance with the instructions of block 1104, a respective transducer in the first pair of adjacent transducers 306 (e.g., transducer 306i) and a respective transducer in the second pair of adjacent transducers 306 (e.g., transducer 306j) forms part of a third pair of adjacent ones of transducers 306 in the distribution. In some embodiments, diagonally arranged pairs of adjacent ones of the transducers 306 are also considered in method 1100. In some embodiments, the transducers 306 of the selected first pair of adjacent ones of the transducers 306 in the distribution are located on a first elongate member 304 and the transducers 306 of the selected second pair of adjacent ones of the transducers 306 in the distribution are located on a second elongate member 304, the second elongate member 304 different than the first elongate member 304. In some embodiments, a region of space associated with a physical part of the transducer-based device 300 is between the transducers 306 of (a) the selected first pair of adjacent ones of the transducers 306 in the distribution, (b) the selected second pair of adjacent ones of the transducers 306 in the distribution, or (c) each of (a) and (b), and a region of space not associated with any physical part of the transducer-based device 300 is between the transducers 306 of the third pair of adjacent ones of the transducers 306 in the distribution.

In some embodiments, the delay instructions of block 1104 include instructions configured to cause a delay of the activation of the first pair of adjacent ones of the transducers 306 in the distribution until after completion of the activation of the second pair of adjacent ones of the transducers 306 in the distribution. In some embodiments, the third pair of transducers 306 may form part of the selected pairs of adjacent transducers 306. For example, each of the first, the second, and the third pairs of adjacent ones of the transducers 306 may be selected by a selection of a respective between graphical element (e.g., between graphical element 504, 604) associated with each pair. In some embodiments, method 1100 may include instructions (not shown) configured to cause a delay of the activation of a selected third pair of adjacent ones of the transducers 306 in the distribution with respect to a starting of the activation of each of the selected first pair and the selected second pair of adjacent ones of the transducers 306 in the distribution in response to the circumstance where a respective transducer 306 in each of the selected first and the second pairs of adjacent ones of transducers 306 in the distribution forms part of the selected third pair of adjacent ones of the transducers 306 in the distribution. In various embodiments, method 1100 includes instructions (not shown) configured to cause the starting of the activation of the selected third pair of adjacent ones of the transducers 306 in the distribution after completion of the activation of each of the selected first and the selected second pair of adjacent ones of the transducers 306 in the distribution.

In some embodiments, the delay instructions of block 1104 are configured to cause a delay of the starting of the activation of the first pair of adjacent ones of the transducers 306 in the distribution until after expiry of a time interval, the time interval commencing after completion of the activation of the second pair of adjacent ones of the transducers 306 in the distribution. The use of a time interval may be motivated for different reasons. For example, the time interval may provide a cool down time period to further promote more uniform ablation region characteristics. In some embodiments, the third pair of adjacent ones of the transducers 306 in the distribution is not selected in accordance with the instructions of block 1102. In some embodiments, a predetermined delay is employed by the delay instructions of block 1104.

In various embodiments, the activation instructions of block 1104 cause energy from an energy source device system (e.g. energy source device system 340) to be delivered to each of at least some of the selected pairs of adjacent ones of the transducers in the distribution. In some of these various embodiments, the delivered energy is sufficient for tissue ablation. In some of these various embodiments, the input-output device system includes a sensing device system (e.g., sensing device system 325) configured to detect at least one tissue characteristic (e.g., tissue impedance) at respective locations at least proximate each of the selected pairs of adjacent ones of the transducers 306 in the distribution with the energy delivered to each of at least some of the selected pairs of adjacent ones of transducers 306 in the distribution (e.g., in some embodiments, tissue impedance may be measured between transducers on the structure 308 or between a transducer on the structure 308 and the indifferent electrode 326). The activation instructions of block 1104 may include instructions (not shown) configured to cause bipolar activation of at least the selected first pair of adjacent ones of the transducers 306 in the distribution and the selected second pair of adjacent ones of the transducers 306 in the distribution. The activation instructions of block 1104 may include instructions (not shown) configured to cause monopolar activation of at least the selected first pair of adjacent ones of the transducers 306 in the distribution and the selected second pair of adjacent ones of the transducers 306 in the distribution.

In various embodiments, the activation instructions of block 1104 include instructions (not shown) configured to cause activation of at least the selected first pair of adjacent ones of the transducers 306 in the distribution for a first time interval and cause activation of at least the second pair of adjacent ones of the transducers 306 in the distribution for a second time interval, a duration of the second time interval being different than a duration of the first time interval. In some of these various embodiments, the first time interval, the second time interval, or each of the first and the second time interval is a predetermined time interval. Example reasons for having these different activation time intervals are discussed below with respect to FIG. 14. Also, each of the transducers 306 in the distribution can be spaced apart from each of the other transducers 306 in the distribution, according to some embodiments.

Figure 13:
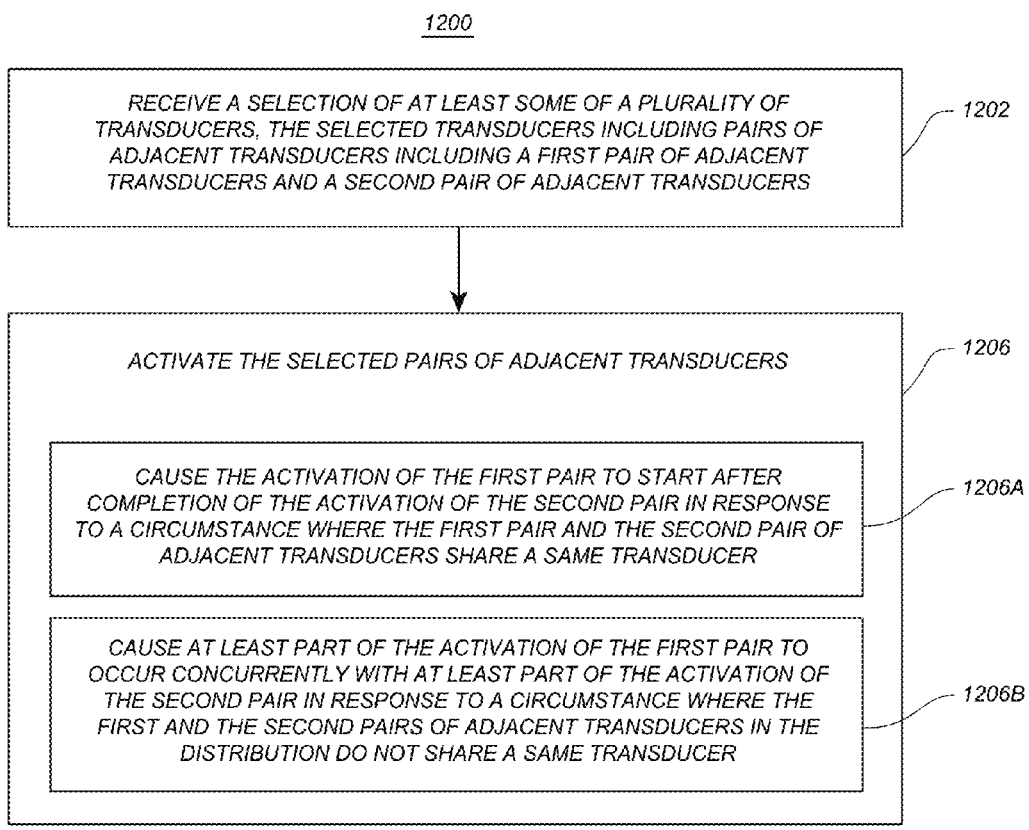
FIG. 13 illustrates a block diagram of a method for activating transducers of a transducer-based device according to various example embodiments.

FIG. 13 is a block diagram showing a method 1200 including instructions provided by various blocks (e.g., instructions provided in a program) for selecting and activating transducers in a transducer-based device such as transducer-based device 300 according to some embodiments. Block 1202 includes selection instructions configured to cause a reception from an input-output device system (e.g., input-output device system 120 or 320) of at least some of a plurality of transducers arranged in a distribution by a transducer-based device (e.g., transducers 306 shown in FIG. 3B), the selected transducers including pairs of adjacent transducers including at least a first pair of adjacent ones of transducers arranged in the distribution and a second pair of adjacent ones of the transducers arranged in the distribution. This selection could be according to the above-discussed first sequence or first order, in some embodiments. In some embodiments, method 1200 may include a subset of the associated blocks or additional blocks than those shown in FIG. 13. Reference is herein made to the transducers 306 for convenience and it is understood that other transducer-based devices having other transducers may be associated with other embodiments employing aspects of method 1200. Block 1206 includes activation instructions configured to cause activation of the selected pairs of adjacent transducers 306 in the distribution. In various embodiments, the instructions of block 1206 can include one or both of the two sets of instructions respectively associated with blocks 1206A and 1206B, each of which can be employed in response to a particular circumstance.

Block 1206A includes instructions configured to cause the activation of the first pair of adjacent ones of the transducers 306 in the distribution to start after completion of the activation of the second pair of the adjacent ones of the transducers 306 in the distribution in response to a circumstance where the first pair and the second pair of adjacent ones of the transducers 306 in the distribution share a same transducer 306. Block 1206B includes instructions configured to cause at least part of the activation of the first pair of adjacent ones of the transducers 306 in the distribution to occur concurrently with at least part of the activation of the second pair of adjacent ones of the transducers 306 in the distribution in response to a circumstance where the first and the second pair of adjacent ones of the transducers 306 in the distribution do not share a same transducer 306. For example, if the selected first pair of adjacent transducers 306 includes transducers 306*d* and 306*e* and the selected second pair of adjacent transducers 306 includes transducers 306*e* and 306*f*, each of the selected first and the second pairs of adjacent transducers shares a same transducer 306*e* and the activation of the first pair of adjacent transducers 306 may occur after the completion of the activation of the second pair of adjacent transducers 306 in accordance with the instructions of block 1206A. If the selected first pair of adjacent transducers 306 includes transducers 306*d* and 306*e* and the selected second pair of adjacent transducers 306 includes transducers 306*g* and 306*h*, each of the first and the second pairs of adjacent transducers does not share a same transducer 306 and at least part of the activation of the first pair of adjacent transducers 306 may occur concurrently with at least part of the activation of the second pair of adjacent transducers 306 in accordance with the instructions of block 1206B. Ablation activation embodiments carried out in accordance with the instructions of method 1200 may allow for more uniform ablation characteristics.

In some embodiments, an activation sequence or order, which may be the above-discussed second sequence or second order, respectively, may be generated based on an analysis of transducer sets in an initial transducer-selection sequence or order, which may be the above-discussed first sequence or first order, respectively, can occur according to the instructions of block 1206A, block 1206B, or both blocks 1206A and 1206B.

In some embodiments, aspects of method 1200 may be combined with aspects of method 1100. For example, the activation instructions of block 1206 may further include instructions (not shown) configured to cause the activation of the selected first pair of adjacent transducers 306 to start after a completion of the activation of the selected second pair of adjacent transducers 306 in response to a circumstance where a respective transducer 306 in each of the selected first and the second pairs of adjacent transducers 306 forms part of another pair of adjacent ones of the transducers 306 in the distribution.

In some embodiments, the activation instructions of block 1206 include instructions (not shown) configured to cause activation of at least the selected first pair of the adjacent transducers 306 for a first time interval and cause activation of at least the selected second pair of adjacent transducers for a second time interval, a duration of the second time interval being different than a duration of the first time interval. Activation of selected pairs of adjacent transducers 306 may include an activation resulting in tissue ablation, an activation resulting in the determination of a tissue characteristic (e.g., tissue impedance), or other forms of activation. Activation of the selected pairs of adjacent transducers 306 may include bipolar activation or monopolar activation or combinations thereof. Selection of the pairs of adjacent transducers 306 may be accomplished by the selection of various graphical elements as previously described in this detailed description.

As discussed above, in some embodiments, generation of the above-discussed second sequence or second order in accordance with the generation instructions of block 809 may be based at least in part on various aspects of FIGS. 11-16 and any other embodiment in which a transducer-activation sequence is generated that might be different than a transducer-selection sequence (although the invention is not limited to these examples).

In some embodiments, generation of a second sequence of transducer sets or a second order of transducer sets in accordance with the generation instructions of block 809 may be based at least on the analysis that reduces an overall activation time of various transducer sets in a selected group. An analysis of the transducers sets in a selected group to determine the second sequence may take various factors into account especially when a reduction in, or the optimization of, the overall activation time of various ones or all of the transducer sets in the group is desired. For example, in some embodiments that employ relatively large numbers of transducers (e.g., a hundred or more transducers), economic constraints may prevent having a one-to-one correspondence between a respective one of a plurality of energy source devices (e.g., power source drivers) and a respective one of the plurality of transducers. Generation of a second sequence or second order in accordance with the generation instructions of block 809 may be based at least on an analysis of a connection arrangement between each of at least some of the transducer sets in the group and the plurality of energy source devices. For example, generation of a second sequence or second order in accordance with the generation instructions of block 809 may be based at least on an analysis of availability of a particular one of the plurality of energy sources during a desired activation of an associated one of the transducer sets.

Other factors may include differing activation time intervals. Different activation time intervals may be associated with different transducer sets for various reasons. As described above, in some embodiments, activation of a first transducer set may occur after a completion of the activation of a second transducer set. In some embodiments, an employed memory device system (e.g., memory device systems 130, 330) may store information associated with a respective activation time interval for each of at least two of the selected transducer sets, the respective activation time intervals having different durations. The analysis may include an analysis of each of the respective activation time intervals or other factors associated with these time intervals.

Figure 14:
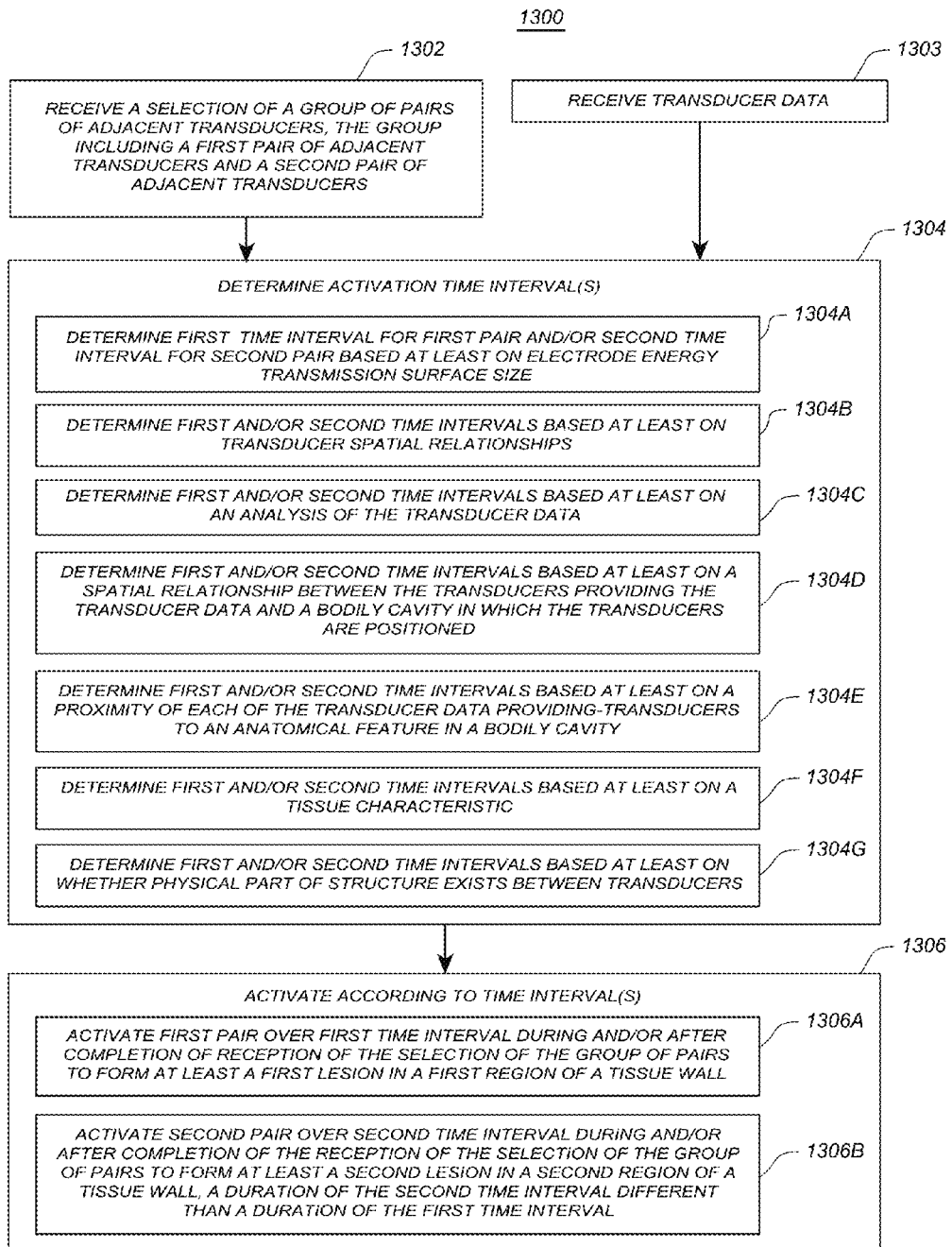
FIG. 14 illustrates a block diagram of a method for activating transducers of a transducer-based device according to various example embodiments.

FIG. 14 is a block diagram showing a method 1300 including instructions provided by various blocks (e.g., instructions provided in a program) for selecting and activating transducers in a transducer-based device according to some embodiments. In some embodiments, method 1300 may include a subset of the associated blocks or additional blocks than those shown in FIG. 14. In some embodiments, method 1300 may include a different sequence between various ones of the associated blocks than those shown in FIG. 14.

Block 1302 includes reception instructions configured to cause a reception from an input-output device system (e.g., input-output device system 120 or 320) of a selection of a group of pairs of adjacent transducers arranged in a distribution by a transducer-based device (e.g., transducer-based device 300 shown in FIG. 3B). This selection could be according to the above-discussed first sequence or first order, in some embodiments. Reference is herein made to the transducers 306 for convenience for describing various embodiments and it is understood that other transducer-based devices having other transducers may be associated with other embodiments employing aspects of method 1300. In various embodiments, the selected group of pairs of adjacent ones of the transducers 306 includes at least a first pair of adjacent ones of the transducers 306 in the distribution and a second pair of adjacent ones of the transducers 306 in the distribution.

In this example embodiment, block 1306 includes activation instructions, which in this example embodiment, are configured to cause energy from an energy source device system (e.g., energy source device system 340) to be delivered to the transducers 306 of various ones of the selected pairs of adjacent transducers 306 in the distribution. In this embodiment, the instructions of block 1306 include instructions associated with blocks 1306A and 1306B. Block 1306A includes first delivery instructions configured to cause a first delivery of energy to be provided by the energy source device system to each of the transducers 306 of the first pair of the adjacent ones of the transducers 306 in the distribution, the first delivery of energy configured to occur over a first interval (a) during the reception of the selection of the group of pairs of adjacent transducers 306, (b) after a completion of the reception of the selection of the group of pairs of adjacent transducers 306, or both (a) and (b) to form at least a first lesion in a first region of a tissue wall. In other words, in some embodiments, the energy provided to each of the transducers of the first pair of adjacent ones of the transducers is sufficient for forming at least the first lesion in the first region of the tissue wall over the first time interval. Block 1306B includes second delivery instructions configured to cause a second delivery of energy to be provided by the energy source device system to each of the transducers 306 of the second pair of the adjacent ones of the transducers 306 in the distribution, the second delivery of energy configured to occur over a second interval (c) during the reception of the selection of the group of pairs of adjacent transducers 306, (d) after a completion of the reception of the selection of the group of pairs of adjacent transducers 306, or both (c) and (d) to form at least a second lesion in a second region of a tissue wall. In other words, in some embodiments, the energy provided to each of the transducers of the second pair of adjacent ones of the transducers is sufficient for forming at least the second lesion in the second region of the tissue wall over the second time interval. In some embodiments, a duration of the second time interval is different than a duration of the first time interval. In some embodiments, the first lesion extends continuously across the first region between the transducers 306 of the first pair of adjacent transducers 306. In some embodiments, the second lesion extends continuously across the second region between the transducers 306 of the second pair of adjacent transducers 306. In some embodiments, each of the first lesion, the second lesion, or both the first and the second lesions act as an electrophysiological activity conduction block that blocks electrophysiological activity in a respective one of the first region and the second region of the tissue wall. In some embodiments, the energy provided to each of the transducers of the first pair of adjacent ones of the transducers has a magnitude for ablating tissue of a tissue wall over the first time interval to a first depth, and the energy provided to each of the transducers of the second pair of adjacent ones of the transducers has a magnitude for ablating tissue of a tissue wall over the second time interval to the first depth.

The duration of activation time intervals (e.g., the first and the second time intervals in this example embodiment) may vary based on various factors, such as those described below with respect to blocks 1304A-1304G. In some embodiments, block 1304 includes instructions configured to cause a determination of various ones of the activation time intervals. In some embodiments, block 1304 includes first determination instructions configured to cause a determination of a duration of a first time interval for a first pair of transducers (selected, e.g., according to block 1302) and second determination instructions configured to cause a determination of a duration of a second time interval for a second pair of transducers (selected, e.g., according to block 1302). It should be noted, however, that the determinations described herein with respect to block 1304 need not apply only to the activation intervals for transducer pairs, and equally pertain to the determination of activation intervals for single transducers. Blocks 1304A-1304G provide examples of factors that can be used individually or in combination to determine one or more activation time intervals.

In some embodiments, the duration of the first time interval is determined in accordance with the instructions of block 1304A based at least on the respective corresponding size of the energy transmission surface 319 of each of at least one of the electrodes 315 of the first pair of adjacent transducers 306, and additionally or alternatively, the duration of the second time interval is determined based at least on the respective corresponding size of the energy transmission surface 319 of at least one of the electrodes 315 of the second pair of adjacent transducers 306. In some embodiments, a duration of the second time interval may be different than the duration of the first time interval at least because of a difference in a magnitude between a determined corresponding size of at least one of the respective electrodes 315 of the first pair of adjacent transducers 306 and a determined corresponding size of at least one of the respective electrodes 315 of the second pair of adjacent transducers 306.

For example, with respect to FIG. 3B, when energy is delivered to each of a pair of transducers during an activation resulting in ablation (e.g., bipolar ablation), tissue ablation depths may be dependent on the size of the electrodes 315 associated with the pair of the transducers 306, with transducer pairs having relatively larger electrodes 315 reaching a desired ablation depth in a shorter duration than transducer pairs having relatively smaller electrodes 315.

In this example embodiment, three transducers 306 including a first transducer 306*m*, a second transducer 306*l*, and a third transducer 306*n* are shown. In this example embodiment, the selected first pair of adjacent transducers 306 includes transducers 306*l* and 306*m* and the selected second pair of transducers 306 includes transducers 306*m* and 306*n*. It is understood that selected first and second pairs of adjacent transducers 306 need not share a same transducer 306 and, in some embodiments, each of the transducers in the selected first pair of adjacent transducers 306 is different from each of the transducers in the selected second pair of adjacent transducers 306. In this example embodiment, each of the first, the second, and the third transducers 306*m*, 306*l* and 306*n* includes a respective electrode (i.e., a respective one of first electrode 315*m*, second electrode 315*l*, and third electrode 315*n*) having a respective energy transmission surface 319 (i.e., a respective one of first energy transmission surface 319*m*, second energy transmission surface 319*l* and third energy transmission surface 319*n*). In this example embodiment, each of the energy transmission surfaces 319 has a corresponding size and a corresponding shape. In this particular embodiment, a magnitude of a surface area size of an exposed conductive portion of the first energy transmission surface 319*m* associated with first electrode 306*m* is less than a magnitude of a surface area size of an exposed conductive portion of the second energy transmission surface 319*l* associated with the second transducer 306*l*. In this particular embodiment, the magnitude of the surface area size of the exposed conductive portion of the first energy transmission surface 319*m* is greater than a magnitude of a surface area size of an exposed conductive portion of the third energy transmission surface 319*n* associated with the third transducer 306*n*. Magnitude differences between the corresponding sizes of various transducers 306 employed in various embodiments may be motivated by various factors. In this example embodiment, electrodes 315 having smaller sizes are employed in regions where the elongate members 304 are spaced closer with respect to one another or overlap one another.

As discussed above, the energy transmission surface 319*l* of electrode 315*l* of the first pair of adjacent transducers 306 has a greater surface area than the energy transmission surface 319*n* of electrode 315*n* of the second pair of adjacent transducers 306, and, therefore, the duration of the second time interval is greater than the duration of the first time interval. In this example embodiment, each of the first and the second pairs of adjacent electrodes 315 has an electrode (e.g., electrode 315*m*) having a same corresponding size.

In some embodiments, a determination of a particular duration of the first and the second time intervals is based on various relationships between the respective transducers 306 of an associated one of the selected first and the second pairs of adjacent transducers 306. For example, as shown by block 1304B in FIG. 14, other factors associated with duration differences between the first and the second time intervals may include various spatial relationships between the transducers of the first and the second pairs of adjacent transducers 306. For instance, in FIG. 3B, transducers 306*o* and 306*n* can form a selected first pair of adjacent ones of the transducers that are spaced with respect to one another by a first transducer-to-transducer distance (not called out) while transducers 306*p* and 306*l* can form a selected second pair of adjacent transducers that are spaced with respect to one another by a second transducer-to-transducer distance (not called out) that is different than the first transducer-to-transducer distance. In some embodiments, differences between the respective transducer-to-transducer distances may result from inherent design features. In some embodiments, differences between the respective transducer-to-transducer distances may occur as transducers are positioned to conform to a bodily cavity of a particular size. In some embodiments, the duration of the first time interval is determined in accordance with the instructions of block 1304B based at least on the first transducer-to-transducer distance and the duration of the second time interval is determined based at least on the second transducer-to-transducer distance. In some embodiments, a duration of the second time interval may be different than the duration of the first time interval at least because the second transducer-to-transducer distance is longer than the first transducer-to-transducer distance. For example, longer ablation times may be required for increased spacings between a respective pair of adjacent transducers. In this example embodiment, the second transducer-to-transducer distance is greater than the first transducer-to-transducer distance and the duration of the second time interval is greater than the first time interval.

With respect to block 1304G in FIG. 14, other factors associated with duration differences between the first and the second time intervals may include whether or not physical structure exists between the selected first pair of adjacent transducers and between the selected second pair of adjacent transducers. In this regard, in some example embodiments, a first region of space (e.g., region of space 360) that is associated with a physical part of structure 308 (e.g., FIG. 3B) is located between the respective transducers 306*b*, 306*c* of a selected first pair of adjacent ones of the transducers 306 while a second region of space (e.g., region of space 350) that is not associated with any physical part of the structure 308 is located between the respective transducers 306*b*, 306*a* of a selected second pair of adjacent ones of the transducer 306. In various ones of these example embodiments, each of the first and the second regions of space do not include any transducer. In some embodiments, a duration of the first time interval is determined in accordance with the instructions of block 1304G based at least on a result that the first region of space being associated with a physical part of structure 308 and a duration of the second time interval is determined in accordance with the instructions of block 1304G based at least as a result of the second region of space being not associated with any physical part of structure 308. In some embodiments, a duration of the second time interval may be different than the duration of the first time interval at least because the first region of space is associated with a physical part of structure 308 and the second region of space is not associated with any physical part of structure 308. For example, tissue ablated adjacent the first region of space (e.g., region of space 360) may be relatively shielded from cooling effects associated with fluid flow (e.g., blood flow) within the bodily cavity by a physical part of structure 308 while tissue adjacent the second region of space (e.g., region of space 350) is relatively exposed to the cooling effects of the fluid flow due to the absence of a physical part of structure 308 thereby possibly requiring longer activation durations. In one example embodiment, the first region of space associated with a physical part of the structure 308 is between the transducers 306*b*, 306*c* and the second region of space that is not associated with any physical part of structure 308 is between the transducers 306*b*, 306*a* of the second pair of adjacent transducers and the duration of the second time interval is greater than the duration of the first time interval.

In some example embodiments, the first time interval (for activating the first pair of transducers, e.g., selected according to block 1302), the second time interval (for activating the second pair of transducers, e.g., selected according to block 1302) or both the first and the second time intervals may be determined at least in part from transducer data. For example, in various embodiments, block 1303 may include data request instructions configured to cause a reception of transducer data via the input-output device system, the transducer data indicating data acquired by at least some of the plurality of transducers 306. In some of these various embodiments, duration instructions provided by block 1304C are configured to cause a determination of the first time interval, the second time interval, or both the first and the second time intervals based at least on an analysis of the transducer data. In some of these embodiments the first delivery instructions of block 1306A are configured to cause the first delivery of energy to be provided by the energy source device system to each of the transducers 306 of the first pair of adjacent transducers 306 during or after completion of the reception of the transducer data. In some of these embodiments, the second delivery instructions of block 1306B are configured to cause the second delivery of energy to be provided by the energy source device system to each of the transducers 306 of the second pair of adjacent transducers 306 during or after the completion of the reception of the transducer data.

Various analyses of the transducer data may be performed. In some embodiments, positional determination instructions associated with block 1304D may be configured to cause, based at least on an analysis of the transducer data, a determination of a spatial relationship between the transducers 306 providing the transducer data and a bodily cavity in which the transducers 306 are positioned. In this regard, the first time interval, the second time interval, or both the first and the second time intervals can be determined based at least on the determined spatial relationship at block 1304D.

In some embodiments, proximity determination instructions associated with block 1304E may be configured to cause, based at least on an analysis of the transducer data, a determination of a proximity of each of the transducer data providing-transducers 306 to an anatomical feature in a bodily cavity in which the transducers 306 are positioned. In this regard, the first time interval, the second time interval, or both the first and the second time intervals can be determined according to block 1304E based at least on the determined proximity of each of the transducer data providing-transducers to the anatomical feature.

In some embodiments, tissue determination instructions associated with block 1304F are configured to cause, based at least on an analysis of the transducer data, a determination of a tissue characteristic (e.g., tissue thickness, tissue type). In this regard, the first time interval, the second time interval, or both the first and the second time intervals can be determined according to block 1304F based at least on the determined tissue characteristic.

For example, in regard to blocks 1304D, 1034E, and 1304F, the transducer data might include impedance or other information that indicates that a first pair of transducers is in contact with thinner tissue than is a second pair of transducers. Thicker tissue, in some embodiments, requires a longer ablation duration than thinner tissue and, therefore, the first pair of transducers might be activated, e.g., by delivery of ablative energy, according to the instructions of block 1306 for a first interval longer than a second interval by which the second pair of transducers is activated (assuming the transducers of the first and second pairs have roughly equivalent sizes and energy delivery capabilities).

In some embodiments, the determination instructions associated with block 1304 (or any sub-block therein) are configured to determine the duration of the first time interval, the second time interval or both the first and the second time intervals based at least in part from a selection of data stored in a memory device system (e.g., memory device system 130, 330). In some example embodiments, predetermined values (e.g., default values) associated with the first time interval, the second time interval, or both the first and the second time intervals are provided by data stored in the memory device system. In this regard, the time intervals can be pre-calculated (instead of being calculated in real-time) in some embodiments and stored in the memory device system, such that the determination at, for example, any of blocks 1304A-G, could merely be a retrieval of the appropriate time intervals from the memory device system.

In some embodiments, generation of a second sequence or second order in accordance with the generation instruction of block 809 may be based at least in part on various aspects of the determinations described with respect to block 1304, which can generate activation time intervals and then cause transducer activation according to the generated time intervals according to the above-discussed second sequence or second order in a time-efficient manner.

In various embodiments, a particular transducer may form part of each of at least two sets of transducers arranged in a distribution by a transducer-based device, each of the at least two sets of transducers independently selectable, (e.g., by a graphical interface described herein). In various embodiments, an activation of a particular transducer may vary based at least on which of the at least two selectable sets of transducers the particular transducer forms part of.

Figure 15A:
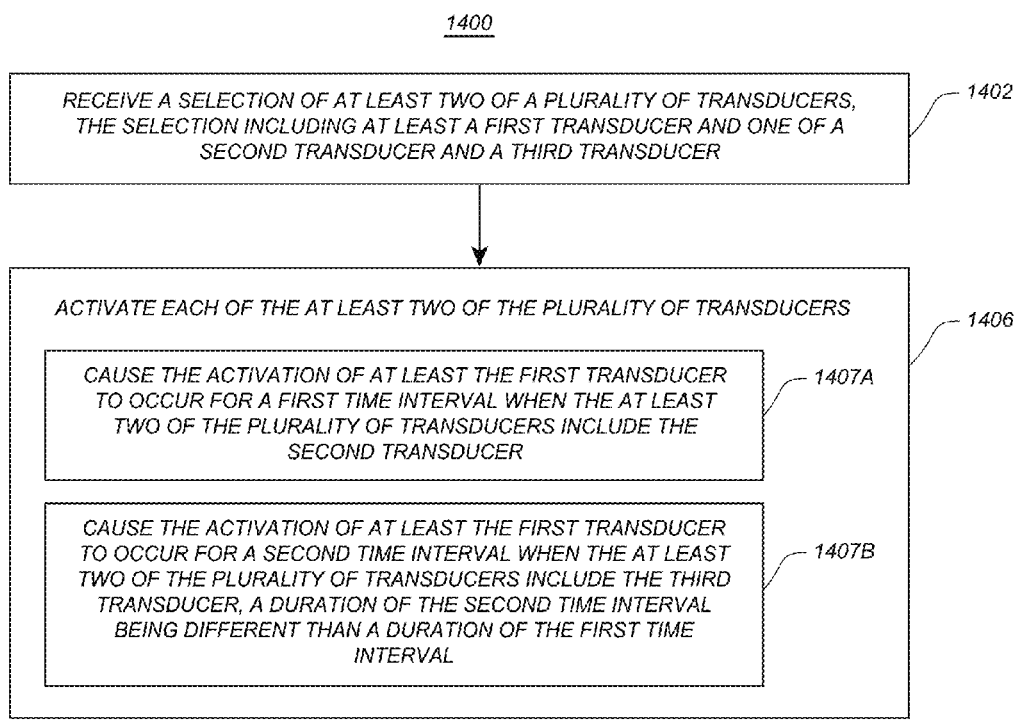
FIG. 15A illustrates a block diagram of a method for activating transducers of a transducer-based device according to various example embodiments.

For example, FIG. 15A includes a block diagram showing a method 1400 including instructions provided by various blocks (e.g., instructions provided in a program) for selecting and activating transducers in a transducer-based device according to some embodiments. In some embodiments, method 1400 may include a subset of the associated blocks or additional blocks than those shown in FIG. 15A. Block 1402 includes reception instructions configured to cause a reception from an input-output device system (e.g., input-output device system 120 or 320) of a selection of at least two of a plurality of transducers arranged in a distribution by a transducer-based device (e.g., transducer-based device 300 shown in FIG. 3B). This selection could be according to the first sequence or first order described above with respect to FIG. 10, in some embodiments. In this example embodiment, the selected at least two of the plurality of transducers include at least a first transducer and one of a second transducer and a third transducer in the distribution. Each of the first, the second, and the third transducers are different transducers in the distribution. In various embodiments, each of the first transducer and the second transducer form a first pair of adjacent ones of the transducers in the distribution and each of the first transducer and the third transducer form part of a second pair of adjacent ones of the transducers in the distribution. Reference is herein made to the transducers 306 for convenience of describing various embodiments but it is understood that other transducer-based devices having other transducers may be associated with other embodiments employing aspects of method 1400. In some embodiments, independent selections of each of at least some of a plurality of graphical elements provided by a display are employed to select at least the first transducer 306, the second transducer 306 or the third transducer 306. In some embodiments, a selection of a single graphical element (e.g., between graphical element 504, 604) provided by a display is employed to select either a first transducer set that includes at least the first transducer 306 and the second transducer 306, or a second transducer set that includes at least the first transducer 306 and the third transducer 306. In some embodiments, the selection is a first selection in which the first and the second transducers 306, but not the third transducer 306, are selected. The reception instructions of block 1402 may be further configured to cause a reception of a second selection from the input-output device system after receiving the first selection and after initiation of an activation of at least the first transducer, with the second selection being a selection of at least the third transducer 306 in the distribution. In some embodiments, each of the first and the second transducers 306 are located on a first elongate member 304 of the transducer-based device 300 and the third transducer 306 is located on a second elongate member 304, the second elongate member 304 different from the first elongate member 304.

Block 1406 includes activation instructions configured to cause activation via the input-output device system of each of the selected at least two of the plurality of transducers 306. In some example embodiments, block 1406 includes blocks 1407A and 1407B. Block 1407A includes instructions configured to cause the activation of at least the first transducer 306 to occur for a first time interval when the selected at least two of the plurality of transducers 306 includes the second transducer 306 in the distribution. Block 1407B includes instructions configured to cause the activation of at least the first transducer 306 to occur for a second time interval when the selected at least two of the plurality of transducers 306 includes the third transducer 306 in the distribution. In this embodiment, a duration of the second time interval is different than a duration of the first time interval. Activation of the selected at least two of the plurality of transducers 306 may include an activation resulting in tissue ablation, an activation resulting in the determination of a tissue characteristic (e.g., tissue impedance), or other forms of activation. Activation of the selected at least two of the plurality of transducers 306 may include bipolar activation or monopolar activation or combinations thereof.

As previously described in this detailed description, various factors may have a bearing on the use of different activation time intervals. In some embodiments, each of the first, the second, and the third transducers 306 includes a respective electrode 315 having an energy transmission surface 319, each energy transmission surface 319 having a respective corresponding size, with the respective corresponding size associated with the second transducer 306 having a different magnitude than the respective corresponding size associated with the third transducer 306. Such may occur, for example in one particular embodiment, when the first transducer is transducer 306$m$, the second transducer is transducer 306$l$, and the third transducer is transducer 306$n$ as shown in FIG. 3B. In this particular embodiment, a duration of the second time interval is greater than a duration of the first time interval when the selected at least two of the plurality of transducers 306 includes third transducer 306$n$ whose energy transmission surface 319$n$ has a smaller surface area than the surface area of the energy transmission surface 319$l$ associated with the second transducer 306$l$.

In various embodiments, the first transducer 306 is spaced from the second transducer 306 by a first distance in the distribution, and the first transducer 306 is spaced from the third transducer 306 by a second distance in the distribution, the second distance being longer than the first distance. In some of these various embodiments, a duration of the second time interval associated with a selection of the third transducer 306 is longer than a duration of the first time interval associated with a selection of the second transducer 306.

In various embodiments, a first region of space that is associated with a physical part of the structure 308 of the transducer-based device 300 is located between the second transducer 306 and the first transducer 306 and a second region of space is that is not associated with any physical part of the structure 308 is located between the first transducer 306 and the third transducer 306. Such may occur, for example, when the first transducer is transducer 306b, the second transducer is transducer 306c and the third transducer is transducer 306a as shown in FIG. 3B. In this particular embodiment, a duration of the second time interval is greater than the duration of the first time interval when the selected at least two of the plurality of transducers 306 includes the third transducer (e.g., transducer 306a) which is spaced from the first transducer (e.g., transducer 306b) across the second region of space not associated with any physical part of structure 308.

In some embodiments, each of at least one of the first time interval and the second time interval is a predetermined time interval. In various example embodiments, a sensing device system (e.g., sensing device system 325) detects a detectable attribute (e.g., temperature, a tissue or non-tissue electrical characteristic) at each of a plurality of locations, each of at least two of the plurality of locations at least proximate a respective one of the selected at least two of the plurality of transducers 306. In some of these various embodiments, method 1400 may include instructions (not shown) configured to cause a determination of each of the at least one of the first and the second time intervals based at least on the detected attributes at each of at least some of the plurality of locations. Determination of any of the first and the second time intervals may be based at least on transducer data indicating data acquired by at least some of the plurality of transducers 306. For example, duration determination instructions (not shown) may be provided to cause determination of the duration of the first time interval, the second time interval, or both the first and the second time intervals based at least on a spatial relationship caused to be determined based at least on the transducer data by positional determination instructions (not shown, but similar to the instructions of block 1304D). In some embodiments, the duration determination instructions may be provided to cause determination of the duration of the first time interval, the second time interval, or both the first and the second time intervals based at least on a determined proximity of each of at least some of the plurality of transducers to an anatomical feature in a bodily cavity, the determined proximity caused to be determined based at least on the transducer data by proximity determination instructions (not shown but similar to the proximity determination instructions of block 1304E). In some embodiments, the duration determination instructions may be provided to cause determination of the duration of the first time interval, the second time interval, or both the first and the second time intervals based at least on a determined tissue characteristic caused to be determined based at least on the transducer data by tissue determination instructions (not shown but similar to the instructions of block 1304F). In some embodiments, the activation instructions of block 1406 are configured to cause activation of each of the at least two of the plurality of transducers 306 during or after completion of the reception of the transducer data. In some embodiments, as discussed above, generation of a second sequence or second order in accordance with the generation instruction of block 809 may be based at least in part on various aspects of method 1400.

Figure 15B:
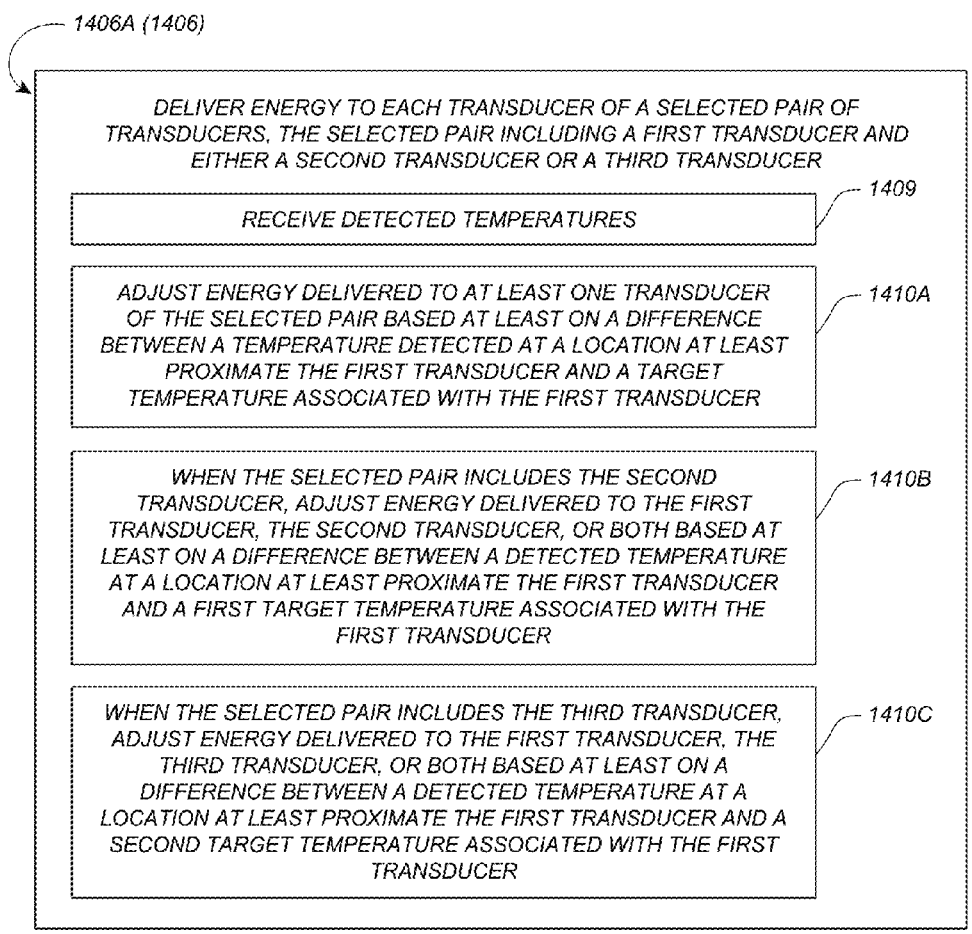
FIG. 15B illustrates a block diagram of a method for activating transducers of a transducer-based device according to various example embodiments.

In some embodiments, other forms of variances in the activation of a particular transducer may occur depending on which of at least two selectable sets of transducers the particular transducer forms part of. For example, FIG. 15B is an exploded diagram of the activation instructions provided by block 1406 according to various embodiments. In some embodiments, the activation instructions provided by block 1406 may include a subset of the associated blocks or additional blocks than those shown in FIG. 15B. The various embodiments associated with block 1406 in FIG. 15A may or may not include various aspects of instructions included in FIG. 15B, and accordingly block 1406 is herein referred to as block 1406A in FIG. 15B. Block 1406A includes various instructions that may be provided by instructions in a program by way of non-limiting example.

In some particular embodiments, block 1406A includes energy delivery instructions configured to selectively cause energy from an energy source device system (e.g., energy source device system 340) to be delivered to each transducer of a selected pair of transducers 306 that includes the first transducer 306 and one of a second transducer 306 and a third transducer 306 selected as per block 1402. Again, each of the first, the second, and the third transducers 306 are different transducers 306. In various embodiments, each of the first transducer 306 and the second transducer 306 form a first pair of adjacent ones of the transducers 306 in the distribution, and each of the first transducer 306 and the third transducer 306 form a second pair of adjacent ones of the transducers 306 in the distribution. It is noted that other transducer-based devices employing other transducers may be employed in other embodiments associated with block 1406A. In some embodiments, the energy delivered from the energy source device system is sufficient for tissue ablation (e.g., bipolar tissue ablation).

In various embodiments associated with block 1406A, a memory device system (e.g., memory device system 130, 330) stores information associated with a respective set of one or more target temperatures for each of a number of the transducers 306 in the distribution of transducers 306 provided by transducer-based device 300 (e.g., at least the first transducer 306 and the second transducer 306 or the third transducer 306 selected according to block 1402). In this regard, thermal sensing instructions provided by block 1409 may be configured to cause reception of detected temperature information indicating respective temperatures detected by a sensing device system (e.g., sensing device system 325) at respective locations at least proximate each of at least some of the transducers 306 in a selected set of transducers 306 (e.g., from block 1402). This detected temperature information can be for comparison with the target temperatures, in some embodiments.

For example, in various embodiments, the energy delivery instructions of block 1406A include adjustment instructions provided by block 1410A configured to cause the energy delivered to at least one transducer 306 of a selected pair of transducers 306 (e.g., from block 1402) to be adjusted based at least on a difference between a respective temperature detected by a sensing device system (e.g., sensing device system 325) at a respective location at least proximate the first transducer 306 of the selected pair of transducers 306 and the respective target temperature associated with the first transducer 306. In some embodiments, the energy delivery instructions of block 1406A are configured to control the energy provided to the at least one transducer 306 of the selected pair of transducers 306 to maintain the temperature detected by the sensing device system at the location at least proximate the first transducer 306 of the selected pair of transducers 306 at or near the respective target temperature associated with the first transducer 306 of the selected pair of transducers 306. In some embodiments, the at least one transducer 306 of the selected pair of transducers 306 includes the first transducer 306 of the selected pair, or the first transducer of the selected pair and either the second transducer 306 or the third transducer 306, whichever is selected according to block 1402.

In some embodiments, the respective set of one or more target temperatures associated with the first transducer 306 of the selected pair of transducers 306 includes a first target temperature and a second target temperature having a different value than the first target temperature. The first target temperature or the second target temperature may be utilized for energy delivery control depending upon what other transducer the first transducer 306 is paired with. For example, the first target temperature may be selected for energy delivery control when the first transducer 306 is paired with the second transducer 306. On the other hand, the second target temperature may be selected for energy delivery control when the first transducer 306 is paired with the third transducer 306. Such an arrangement may be beneficial for temperature control in circumstances where the second transducer 306 and the third transducer 306 have different characteristics, such as size, location, distance from the first transducer 306, relationship with respect to a bodily cavity, or whether a physical part of the transducer-based device (e.g., 300) or a region of space not associated with any physical part of the transducer-based device is between the respective transducer and the first transducer 306, et cetera.

In this regard, block 1406A may include first adjustment instructions provided by block 1410B, the first adjustment instructions configured to, when the selected pair of transducers 306 includes the second transducer 306, cause adjustment of the energy delivered from the energy source device system to the first transducer 306, the second transducer 306, or both the first transducer 306 and the second transducer 306 based at least on a difference between (a) the temperature detected by a sensing device system (e.g., sensing device system 325) at a location at least proximate the first transducer 306 and (b) the first target temperature. On the other hand, block 1406A may include second adjustment instructions provided by block 1410C, the second adjustment instructions configured to, when the selected pair of transducers 306 includes the third transducer 306, cause adjustment of the energy delivered from the energy source device system to the first transducer 306, the third transducer 306 or both the first and the third transducers 306 based at least on a difference between (c) the temperature detected by the sensing device system at a location proximate the first transducer 306 and (d) the second target temperature.

In some embodiments, the selected pair is considered a selected first pair of transducers 306, and the memory device system stores target temperature information associated with a respective target temperature for each transducer 306 of at least a second pair of transducers 306 in the distribution, at least one of the respective target temperatures associated with the transducers 306 of the second pair of transducers 306 having a different value than each of the respective target temperatures associated with the transducers 306 of the first pair of transducers 306. In some embodiments, the respective target temperatures associated with the transducers 306 of the second pair of transducers 306 have different values. In some embodiments, each of the respective target temperatures associated with the transducers 306 of the second pair of transducers 306 has a different value than each of the respective target temperatures associated with the transducers 306 of the first pair of transducers 306. For example, different transducer characteristics (location, size, relationship with respect to another transducer or a bodily cavity, material or lack thereof between transducers) can lead to respectively different target temperatures.

In some embodiments, the respective set of one more target temperatures associated with each of the number of transducers 306 in the distribution may be such that the memory device system stores target temperature information for each transducer 306 of a first pair of the transducers 306 in the distribution, the respective target temperatures associated with the transducers 306 of the first pair of transducers 306 in the distribution having different values. In various embodiments, the first pair of transducers 306 is a first pair of adjacent ones of the transducers 306 in the distribution. For example, when the selected first pair of the transducers 306 includes the first transducer 306 and the second transducer 306 described above, a value of a target temperature associated with the second transducer 306 may be different than a value of a target temperature associated with the first transducer 306. In some embodiments, a respective set of one or more target temperatures associated with the first transducer 306 may include only a single target temperature value.

In a manner similar to at least some of the embodiments employing different activation time intervals, various factors may have a bearing on the use of different target temperatures. For example, in some embodiments, different transducer-electrode energy transmission surface sizes, shapes, or both cause differences in energy-delivery characteristics, which raise the need for different target temperatures. In this regard, in some embodiments, each of the first, the second, and the third transducers 306 includes a respective electrode 315 having an energy transmission surface 319, each energy transmission surface having a respective corresponding size, with the respective corresponding size associated with the second transducer 306 having a different magnitude than the respective corresponding size associated with the third transducer 306. Also, in some embodiments, the energy transmission surface 319 may have a respective shape, the respective shape of the energy transmission surface 319 of the second transducer 306 being different than the respective shape of the energy transmission surface 319 of the third transducer 306. In various embodiments, a respective size or respective shape of the energy transmission surface 319 of at least one of the second transducer 306 and the third transducer 306 may be different than the respective corresponding size or the respective shape of the first transducer 306. Consequently, in some embodiments involving different electrode sizes, shapes, or both sizes and shapes, different target temperatures are associated with the respective transducer sets.

For another example, in some embodiments, different transducer spacings, different types of material between transducers, or both cause differences in energy-delivery characteristics, which raise the need for different target temperatures. In this regard, in various embodiments, the first transducer 306 is spaced from the second transducer 306 by a first distance in the distribution and the first transducer 306 is spaced from the third transducer 306 by a second distance in the distribution, the second distance being different than the first distance. In various embodiments, a first region of space that is associated with a physical part of the structure 308 of the transducer-based device 300 is located between the second transducer 306 and the first transducer 306 and a second region of space is that is not associated with any physical part of the structure 308 is located between the first transducer 306 and the third transducer 306. Consequently, in some embodiments involving different transducer spacings, different types of material between transducers, or both different transducer spacings and different types of material between transducers, different target temperatures are associated with the respective transducer sets.

In some embodiments, a value of various ones of the target temperatures is predetermined. In various example embodiments, a sensing device system (e.g., sensing device system 325) detects a detectable attribute (e.g., temperature, a tissue or non-tissue electrical characteristic) at each of a plurality of locations, each of at least two of the plurality of locations at least proximate a respective transducer 306 of the selected pair of transducers 306 (e.g., selected according to block 1402). In some of these various embodiments, determination instructions (not shown) may be configured to cause a determination of a value of each of at least one of the first and the second target temperatures of the respective set of one or more target temperatures associated with the first transducer 306 based at least on the detected attribute at each of at least some of the plurality of locations. In some of these various embodiments, determination instructions (not shown) may be provided that may be configured to cause a determination of a value of each of at least one of the respective target temperatures associated with various transducers 306 based at least on the detected attribute at each of at least some of the plurality of locations. Determination of a particular target temperature may be based at least on transducer data indicating data acquired by at least some of the plurality of transducers 306. For example, target temperature determination instructions (not shown) may be provided to cause determination of a value of the first target temperature, the second target temperature, or both the first and the second target temperatures of the respective set of one or more target temperatures associated with the first transducer 306 or any of the target temperatures associated with any other of the sets of one or more target temperatures based at least on a spatial relationship caused to be determined based at least on the transducer data by positional determination instructions (not shown, but similar to the instructions of block 1304D). In some embodiments, the target temperatures determination instructions may be provided to cause determination of a value of a particular target temperature based at least on a determined proximity of each of at least some of the plurality of transducers 306 to an anatomical feature in a bodily cavity, the determined proximity caused to be determined based at least on the transducer data by proximity determination instructions (not shown but similar to the proximity determination instructions of block 1304E). In some embodiments, determination instructions may be provided to cause determination of a value of a particular target temperature based at least on a determined tissue characteristic caused to be determined based at least on the transducer data by tissue determination instructions (not shown but similar to the instructions of block 1304F). In some embodiments, the energy delivery instructions of block 1406A are configured to cause activation of each of the selected transducers during or after completion of the reception of the transducer data. In various embodiments, different target temperatures may result in different activation time intervals.

Figure 17:
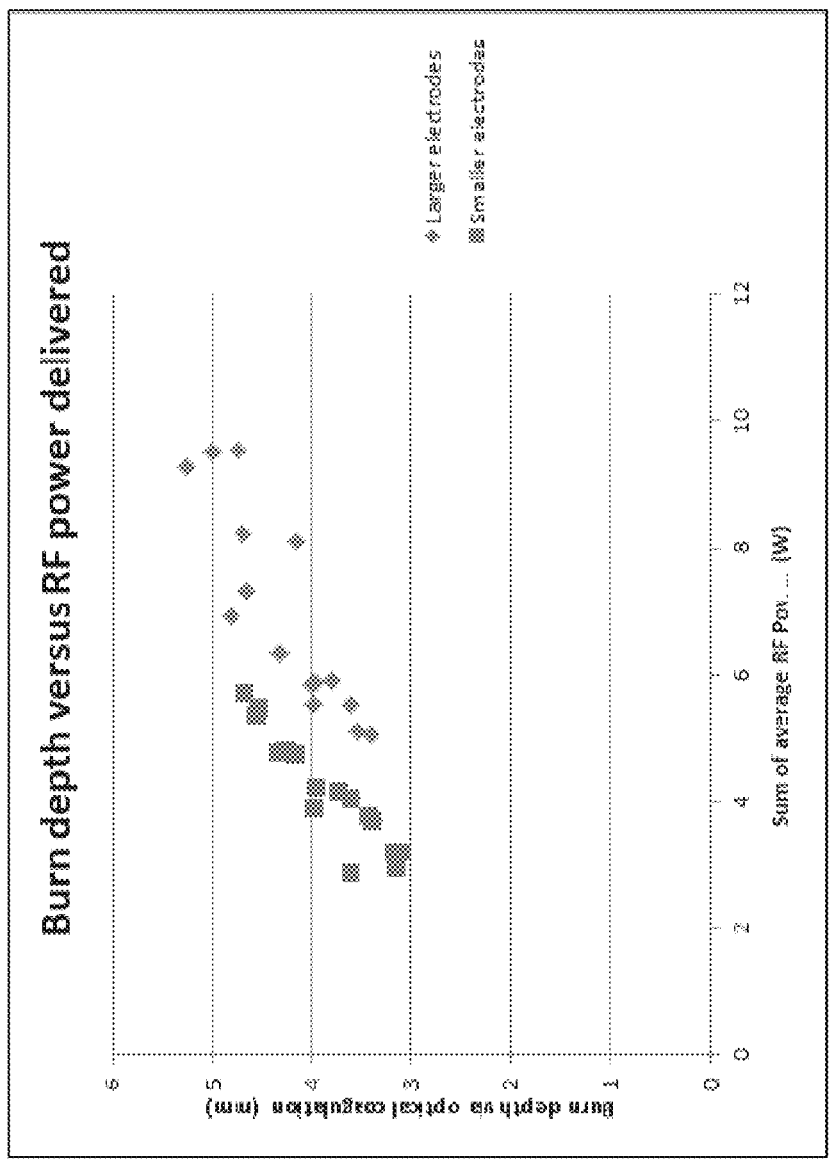
FIG. 17 provides measured data points for ablation depth (i.e., indicated as burn depth) versus RF power that may be expected according to various non-limiting examples.

In view of at least the above-discussion with respect to block 1406A and FIG. 15B, it can be seen that energy delivered to a transducer (e.g., to an electrode thereof) that is sufficient for tissue ablation may be embodied as a target temperature associated with such transducer, and energy that is sufficient for tissue ablation may be dependent upon factors including transducer (or its electrode's) location, size, shape, relationship with respect to another transducer (or its electrode) or a bodily cavity, material or lack thereof between transducers (or their respective electrodes), et cetera. FIG. 17 provides measured data points for ablation depth (i.e., indicated as burn depth) versus RF power that may be expected according to various non-limiting examples, the RF power delivered to the electrodes associated with various pairs of transducers present along a same structural member (e.g., an elongate member 304 in FIG. 3B). The plotted data in FIG. 17 includes data for a pair of "large" electrodes, each of the large electrodes having a surface area of 19.5 mm$^2$, and a pair of "small" electrodes having respective surface areas of 10.9 mm$^2$ and 13.2 mm$^2$.

In another non-limiting example, a pair of electrodes that each are approximately 10 mm$^2$ in surface area and present along a same structural member (e.g., an elongate member 304 in FIG. 3B) may be expected, in some circumstances, to sufficiently ablate intra-cardiac tissue to a depth of approximately 3.1 mm with 2 W of power and to a depth of approximately 4.4 mm with 4 W of power. For yet another non-limiting example, if each electrode in this pair instead has approximately 20 mm$^2$ of surface area, it may be expected that such pair of electrodes will sufficiently ablate intra-cardiac tissue to a depth of approximately 3.1 mm with 4 W of power and to a depth of approximately 4.4 mm with 8 W of power. In these non-limiting examples and in the non-limiting examples illustrated by FIG. 17, power refers to the average power of each electrode summed together, and the depth and power values may be different depending upon the particular shapes of the respective electrodes, the particular distance between them, a degree of electrode-to-tissue contact, and other factors. It is understood, however, that for the same control or target temperature, a larger electrode will achieve a given ablation depth sooner than a smaller electrode. A smaller electrode (e.g., an electrode with a smaller surface area) may need to operate at a higher target temperature to achieve the same ablation depth as compared to a larger (e.g., surface area) electrode (a phenomenon driven by a greater divergence of heat flux of smaller electrodes), which is a compensation not explicitly reflected in FIG. 17. Put differently, a maximum ablation depth (e.g., reached when the temperature profile approaches steady state) of a relatively smaller electrode is typically shallower than that of a relatively larger electrode when ablating at the same control or target temperature, and consequently, a given, less than maximum, ablation depth typically is a larger proportion of the final, maximum, ablation depth for a relatively smaller electrode and typically is reached later in the ablation as compared to a relatively larger electrode. This circumstance may be associated with a lower total power provided to the relatively smaller electrode as compared to a relatively larger electrode, but, nonetheless, the power density present in the relatively smaller electrode may be expected to be somewhat higher as compared to the relatively larger electrode. The phrase "power density" in this context means output power divided by electrode area. Note that power density approximately drives the realized control or target temperature, but in various cases, this is a simplification, and as indicated above, the relationship between power density and realized control or target temperature may be modified by such factors as electrode size, shape, separation, and so forth. It is further noted that when a comparison is made between a relatively larger electrode operated at a lower control temperature versus a relatively smaller electrode operated at a higher temperature, further complications may arise when limits on compensation for electrode size with temperature are also dictated, at least in part, by a desire to reduce occurrences of thermal coagulation of blood or steam formation in the ablated tissue. It is noted that power levels in irrigated electrode systems are typically higher (i.e., in the tens of Watts) than those described above.

Returning for a moment to the above-discussions regarding method 800 of FIG. 10, it was noted that, in some embodiments, generation of the above-discussed second sequence or second order in accordance with the generation instructions of block 809 may be based at least in part on various aspects of FIGS. 11-16 and any other embodiment in which a transducer-activation sequence is generated that might be different than a transducer-selection sequence (although the invention is not limited to these examples).

Figure 16:
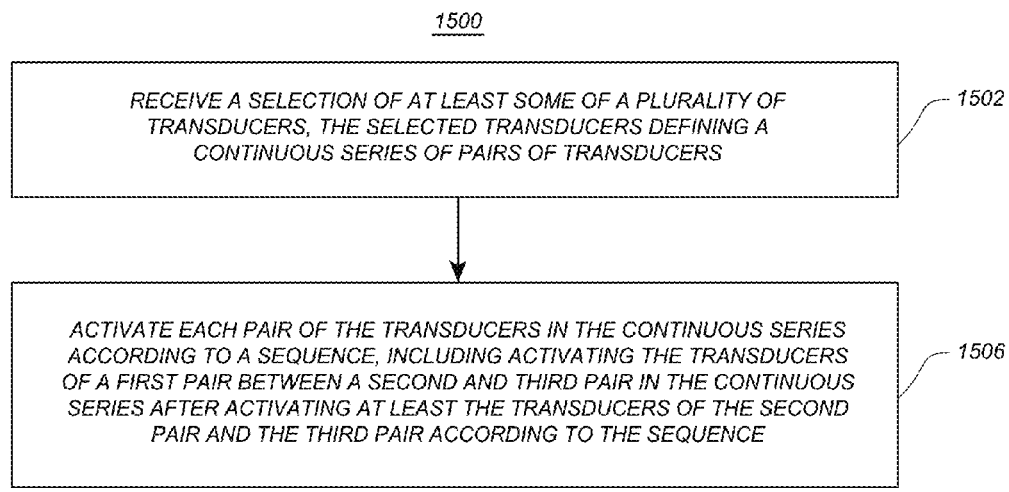
FIG. 16 illustrates a block diagram of a method for activating transducers of a transducer-based device according to various example embodiments.

In this regard, FIG. 16 illustrates another example of how a transducer-activation sequence could be generated from an analysis of transducers in a transducer-selection sequence, which can cause the activation sequence to be different than the selection sequence. It should be noted, however, that the embodiments of FIG. 16 (as well as FIGS. 11-15B) need not exist only in this context of FIG. 10, but can stand independently in their own context.

Accordingly, FIG. 16 is a block diagram showing a method 1500 including instructions provided by various blocks (e.g., instructions provided in a program) for selecting and activating transducers in a transducer-based device according to various embodiments. In some embodiments, method 1500 may include a subset of the associated blocks or additional blocks than those shown in FIG. 16. Block 1502 includes reception instructions configured to cause reception from an input-output device system (e.g., input-output device system 120 or 320) of at least some of a plurality of transducers of a transducer-based device, the plurality of the transducers arranged in a distribution positionable in a bodily cavity. The selected at least some of the transducers define a continuous series of pairs of the transducers. The continuous series includes at least a first pair of the transducers, a second pair of the transducers and a third pair of the transducers. In some of these various embodiments, at least the first pair of the transducers is arranged in the continuous series between the second and the third pairs of the transducers in the continuous series. In some of these various embodiments, each pair of the transducers in the continuous series has a same transducer as another pair in the continuous series. For example, in an embodiment associated with FIG. 5F, the selected between graphical elements 504 identified by corresponding pairs of identification labels: "R:6-Q:6", "Q:6-P:6", "P:6-P:7" "P:7-O:7" "O:7-O:8", "O:8-O:9", "O:9-P:9", "P:9-P:10", "P:10-Q:10", "Q:10-R:10", "R:10-R:9", "R:9-S:9", "S:9-S:8", "S:8-S:7", "S:7-R:7" and "R:7-R:6" are associated with a continuous series of selected pairs of transducers (e.g., transducers 306 of transducer based-device 300), each pair of the transducers in the continuous series having a same transducer as another pair of the transducers in the continuous series. In this embodiment, a visual characteristic of each selected between graphical element 504 changes upon selection of the between graphical element. In this example embodiment, the respective transducers of at least one of the pairs of transducers are located on a same elongate member of a structure of the transducer-based device (e.g., structure 308) and the respective transducers of at least another of the pairs of the transducers are located on different elongate members of the structure. In this example embodiment, a region of space is between two transducers of the selected at least some of the plurality of transducers in the distribution, the two transducers defining one of the pairs of the transducers in the continuous series, the region of space not associated with any physical part of the transducer-based device. In some embodiments, each pair of the transducers in the continuous series is arranged in the continuous series between a respective two adjacent pairs of the transducers in the continuous series. In some embodiments, each pair of the transducers in the continuous series has a same transducer as an adjacent pair of the transducers in the continuous series. In some embodiments, each pair of the transducers in the continuous series is associated with a different respective set of two pairs of the transducers in the continuous series, each of the transducers in each pair of the transducers in the continuous series included in a different pair of the respective set of two pairs of the transducers in the continuous series. In some embodiments, each pair of the transducers in the continuous series is positioned in the continuous series between the two pairs of the transducers of the respective set of two pairs of the transducers in the continuous series. In some example embodiments, the pairs of the transducers in the continuous series are arranged one after another in spatial succession in the distribution. In other embodiments, other forms of visual representations (e.g., tabular or ordered representations) may be employed to provide an operator with information representing, or associated with, the continuous series of the pair of the transducers. In some embodiments, the continuous series is an ordered list of the pairs of the transducers, the ordered list stored by a memory device system (e.g., memory device system 130, 330). In this regard, in some embodiments, the continuous series need not be a spatially-continuous series of adjacent transducers like that shown in FIG. 5F, but could be another ordered representation of transducers, such as an ordered list stored by a memory device system.

Block 1506 includes activation instructions configured to, in response to receiving at least part of the selection (e.g., a sufficient number of the selected at least some of the plurality of transducers (selected, e.g., according to block 1502) to define at least some pairs of the transducers), cause activation of the transducers of each pair of the transducers in the continuous series according to a sequence, the activation including activating the transducers of the first pair of the transducers after activating at least the transducers of the second pair of the transducers and the third pair of the transducers according to the sequence. For example, as compared between FIGS. 5G and 5H, the activation instructions associated with block 810 may in one embodiment include aspects of the activation instructions of block 1506 that in response to at least part of a selection of various transducers that define the continuous series of pairs of the transducers, cause activation of the transducers of each pair of the transducers in the continuous series according to a sequence in which the activation includes activating the transducers of a first pair of the transducers (e.g., the pair of transducers associated with the between graphical element 504 identified as "S:7-R:7") after activating at least the transducers of a second pair of the transducers (e.g., the pair of the transducers associated with the between graphical element 504 identified as "R:6-Q:6") and a third pair of the transducers (e.g., the pair of the transducers associated with the between graphical element 504 identified as "P:10-Q:10") according to the sequence, each of the first, the second and the third pairs forming at least part of the defined pairs.

In this example embodiment, the continuous series is associated with a desired ablation path and the first pair of the transducers is spatially arranged in the continuous series between the second and the third pairs of the transducers in the continuous series. In this example embodiment, the first pair of the transducers (e.g., the pair of the transducers associated with the between graphical element 504 identified as "S:7-R:7") has different transducers than each of the second pair of the transducers (e.g., the pair of transducers associated with the between graphical element 504 identified as "R:6-Q:6") and the third pair of the transducers (e.g., a pair of the transducers associated with the between graphical element 504 identified as "P:10-Q:10"). In some embodiments, the first pair of the transducers has different transducers than the second pair of the transducers, the third pair of the transducers, or both the second and the third pairs of the transducers. In some example embodiments, the sequence is predetermined.

In some embodiments, at least part of the activating of (a) the second pair of the transducers (e.g., the pair of the transducers associated with the between graphical element 504 identified as "R:6-Q:6"), (b) the third pair of the transducers (e.g., the pair of the transducers associated with the between graphical element 504 identified as "P:10-Q:10"), or both (a) and (b) does not occur during the activating of the first pair of the transducers (e.g., the pair of the transducers associated with the between graphical element 504 identified as "S:7-R:7"). In some embodiments, the activating of the first pair of the transducers (e.g., the pair of the transducers associated with the between graphical element 504 identified as "S:7-R:7") occurs after completing the activation of (c) the second pair of the transducers (e.g., a pair of transducers associated with the between graphical element 504 identified as "R:6-Q:6"), (d) the third pair of the transducers (e.g., a pair of transducers associated with the between graphical element 504 identified as "P:10-Q:10"), or both (c) and (d) as shown in FIG. 5H. In this example embodiment, a completion of the activating of (c), (d), or both (c) and (d) is a completion of an ablation of tissue between the respective pair or pairs of the transducers in the continuous series. In this example embodiment, the transducers of the pairs of the transducers are arranged to form a continuous lesion upon completion of activation of the transducers of the pairs of the transducers. In this embodiment, activating of the pairs of the transducers causes energy from an energy source device system (e.g., energy source device system 340) to each of the transducers in each pair of the transducers to form a series of ablated regions in a tissue wall of the bodily cavity in which the transducers are positioned. Each of the ablated regions is positioned one after the other in spatial succession and each of the ablated regions corresponds to one of the plurality of the pairs of the transducers. In this embodiment, each pair of the transducers is an adjacent pair of the transducers in the distribution. Each pair of the transducers is activated in a sequence that causes at least one of the ablated regions in the series of ablated regions to be formed in a region of the tissue wall that has not been previously ablated, the region in the tissue wall that has not been previously ablated being positioned between at least two previously formed ones of the ablated regions in the series of ablated regions. In this embodiment, at least one of the ablated regions in the series of ablated regions is spatially separated from at least one of the at least two previously formed ones of the ablated regions in the series of the ablated regions. In this embodiment, each of the ablated regions in the series of ablated regions is positioned one after the other in spatial succession to form a continuous ablated region. In this example embodiment, each of the ablated regions in the series of ablated regions is adjacently positioned in the series between a respective pair of the ablated regions in the series of the ablated regions. In some embodiments, ablation of the tissue is bipolar ablation. In some embodiments, ablation of the tissue is monopolar ablation. In some embodiments, the activation of the transducers of each pair of the transducers in the continuous series includes bipolar activation between the transducers of each pair of the transducers in the continuous series. In some embodiments, the activation of the transducers of each pair of the transducers in the continuous series includes monopolar activation of the transducers of each pair of the transducers in the continuous series.

In some embodiments, the input-output device system includes a sensing device system (e.g., sensing device system 325) arranged to detect at least one tissue characteristic (e.g., a tissue impedance characteristic) at respective locations at least proximate each of the selected at least some of the plurality of transducers with the energy delivered to each of the selected at least some of the plurality of transducers (e.g., in some embodiments, tissue impedance may be measured between transducers on the structure 308 or between a transducer on the structure 308 and the indifferent electrode 326). In some embodiments, the activating of the first pair of the transducers (e.g., the pair of the transducers associated with the between graphical element 504 identified as "S:7-R:7") occurs after expiry of a time interval, the time interval commencing after completing: (a) the activating the transducers of the second pair (e.g., a pair of the transducers associated with the between graphical element 504 identified as "R:6-Q:6"), (b) the transducers of the third pair (e.g., a pair of the transducers associated with the between graphical element 504 identified as "P:10-Q:10"), or both (a) and (b). In some embodiments, the time interval is a predetermined time interval. In some embodiments, the input-output device system includes a sensing device system and instructions (e.g., instructions provided in a program) configured to cause the sensing device system to detect a detectable attribute (e.g., temperature, an electrical characteristic, a tissue electrical characteristic) at each of one or more locations, each of the one or more locations at least proximate to a respective one of one or more of the transducers in the distribution. Instructions (not shown) may be provided to cause the data processing device system (e.g., data processing device system 110 or 310) to determine at least an end of the time interval based at least on the detected attribute. The use of a time interval in various embodiments may be motivated by various factors. For example, a time interval sufficient to allow for a cool down period may be employed.

In some embodiments, each of the second and the third pairs of the transducers are activated concurrently as exemplified by the respective pairs of the transducers associated with the between graphical element 504 identified as "R:6-Q:6" and the between graphical element 504 identified as "P:10-Q:10" in FIG. 5G. In some embodiments, the activation instructions include instructions configured to, in response to receiving at least part of the selection, cause a starting of the activating of at least one transducer of the second pair of the transducers to occur at a different time than a starting of the activating of at least one transducer of the third pair of the transducers. In some embodiments, the activation instructions include instructions configured, in response to receiving at least part of the selection, cause a completion of the activating of at least one transducer of the second pair of the transducers to occur at a different time than a completion of the activating of at least one transducer of the third pair of the transducers. In some example embodiments, the activation instructions include instructions configured to, in response to receiving at least part of the selection, cause the activating of the transducers of the second pair to occur for a different duration than the activating of the transducers of the third pair.

In some embodiments, block 806 in FIG. 10 includes reception instructions configured to cause reception of a selection from the input-output device system 120 of at least some of a plurality of transducers of a transducer-based device (e.g., 200, 300, or 400), the plurality of transducers arranged in a distribution, the distribution positionable in a bodily cavity. In some embodiments, block 809 in FIG. 10 includes generation instructions configured to, in response to receiving at least part of the selection according to the reception instructions of block 806, cause generation of a plurality of transducer sets from the at least some of the plurality of transducers. The plurality of transducer sets may include at least a first transducer set and one or more other transducer sets. In some embodiments, the first transducer set includes at least a first transducer of the at least some of the plurality of transducers and a second transducer of the at least some of the plurality of transducers. In some embodiments, each of the one or more other transducer sets includes the first transducer, the second transducer, or both the first transducer and the second transducer. In some embodiments, the first transducer is included in the one or more other transducer sets, and the second transducer is included in the one or more other transducer sets. In some embodiments, each of at least one of the plurality of transducer sets includes a different transducer than each of at least one other set of the plurality of transducer sets.

For example, with respect to FIGS. 5G-5I, a first particular one of the one or more other transducer sets may include a transducer set "A" including transducers associated with transducer graphical elements R:6 and Q:6, a second particular one of the one or more other transducer sets may include a transducer set "B" including transducers associated with transducer graphical elements R:7 and S:7, and the first transducer set may include a transducer set "C" including a first transducer and a second transducer respectively associated with transducer graphical elements R:6 and R:7. In this regard, transducer set "A" includes the first transducer associated with transducer graphical element R:6, and transducer set "B" includes the second transducer associated with transducer graphical element R:7. In addition, at least transducer set "A" includes a transducer associated with graphical element Q:6 that is different than those included in each of transducer sets "B" and "C".

In some embodiments, initiation of activation of transducer set "A" (e.g., initiation of activation of the transducers associated with transducer graphical elements R:6 and Q:6 concurrently) occurs at a time T1, according to the activation instructions associated with block 811, just prior to the state shown in FIG. 5G, which shows a during-energy delivery state of transducer set "A". Initiation of activation of transducer set "B" (e.g., initiation of activation of the transducers associated with transducer graphical elements R:7 and S:7 concurrently) may occur at a time T2, according to the activation instructions associated with block 811, sometime after time T1, as shown in FIG. 5H. However, in some embodiments, initiation of activation of transducer set "B" occurs concurrently with that of transducer set "A", such that time T2 equals time T1. In some embodiments, initiation of activation of transducer set "C" (e.g., initiation of activation of the transducers associated with transducer graphical elements R:6 and R:7 concurrently) occurs at a time T3, according to the activation instructions associated with block 811, sometime after times T1 and T2, as indicated by a comparison of at least FIGS. 5H and 5I. For example, in FIG. 5H, transducer set "A" is in a post-energy-delivery state, transducer set "B" is in a during-energy-delivery state, and transducer set "C" is in a pre-energy-delivery state. In FIG. 5I, for example, all of transducer sets "A", "B", and "C" are in a post-energy delivery state, thereby indicating that transducer set "C" initiated activation after transducer sets "A" and "B". In this regard, activation of each respective transducer in transducer set "C" is delayed with respect to a start of the activation of each respective transducer of each of transducer sets "A" and "B", as shown by the comparison of FIG. 5I with FIGS. 5G and 5H. In this regard, it is noted that the transducers associated with transducer graphical elements R:6 and R:7 experience two activation initiations over the time period spanning the activations of transducer sets "A", "B", and "C". The transducer associated with transducer graphical element R:6 experiences activation initiations with transducer sets "A" and "C", and the transducer associated with transducer graphical element R:7 experiences activation initiations with transducer sets "B" and "C".

With respect to FIG. 5G, multiple sets of transducers may be activated concurrently. For example, in FIG. 5G, transducers associated with transducer graphical elements R:6 and Q:6 are concurrently activated with transducers associated with transducer graphical elements Q:10 and P:10. In this regard, when transducers associated with transducer graphical elements R:6 and Q:6 of one transducer set are activated, each respective transducer in at least another particular one of the transducer sets (e.g., transducers associated with transducer graphical elements Q:10 and P:10 shown in FIG. 5G) may be concurrently activated with the transducers associated with transducer graphical elements R:6 and Q:6. However, a transducer set need not be limited to a sequence of adjacent transducers. In this regard, in the immediately previous example, the "one" transducer set may be deemed to include transducers associated with transducer graphical elements R:6, Q:6, Q:10, and P:10, instead of the transducers associated with transducer graphical elements R:6 and Q:6 being considered a separate transducer set from the transducers associated with transducer graphical elements Q:10 and P:10. In this regard, while all transducers in a transducer set may be activated concurrently, this need not be the case. For example, if transducer set "A" is deemed to include transducers associated with transducer graphical elements R:6, Q:6, S:9, and R:9 pursuant to the example embodiments of FIGS. 5G and 5H, the transducers associated with transducer graphical elements R:6 and Q:6 may be activated at time T1 just before FIG. 5G, and the transducers associated with transducer graphical elements S:9 and R:9 may be activated later at time T2 shown in FIG. 5H.

Now assume that transducer set "A" includes transducers associated with transducer graphical elements S:7 and R:7; transducer set "B" includes transducers associated with transducer graphical elements S:9 and R:9; and transducer set "C" includes transducers associated with transducer graphical elements S:7, S:8, and S:9, which may occur according to some embodiments. In some of these embodiments, initiation of activation of transducer set "A" occurs concurrently with initiation of activation of transducer set "B" at a time T1, according to the activation instructions associated with block 811 and indicated in FIG. 5H. Initiation of activation of transducer set "C" occurs after time T1, according to the activation instructions associated with block 811 and shown in FIG. 5I.

In some embodiments, columns 512 are considered rows, and rows 510 are considered columns at least in FIGS. 5G-5I. In this case, each particular column may be identified by the numerical portion of the alpha-numeric identifier of the transducer graphical element 502 arranged along the particular column, and each particular row may be identified by the alphabetic portion of the alpha-numeric identifier of the transducer graphical element 502 arranged along the particular row. In this case (continuing the preceding example), assume that the transducers associated with transducer graphical elements S:7 and S:9 in transducer set "C" are a first transducer and a second transducer, respectively. In this case, the first transducer (associated with transducer graphical element S:7) may be considered to be in a first particular one of the columns (i.e., column "7"), and the second transducer (associated with transducer graphical element S:9) may be considered to be in a second particular one of the columns (i.e., column "9"), where a column (i.e., column "8") is between them. Also in this case, the first transducer (associated with transducer graphical element S:7) and the second transducer (associated with transducer graphical element S:9) are located in a same particular one of the rows (i.e., row "S"). In addition, in this case, the transducer associated with transducer graphical element R:7 in transducer set "A", and the transducer associated with transducer graphical element R:9 in transducer set "B" are located on a row (i.e., row "R") other than the same particular one of the rows (i.e., row "S"). Further, in this case, the transducer associated with transducer graphical element R:7 in transducer set "A" is in the first particular one of the columns (i.e., column "7", which is the same column in which the first transducer associated with transducer graphical element S:7 is located).

Accordingly, in view of the descriptions here, it can be seen that the invention is not limited to any particular arrangement or composition of transducer sets or transducer set activation sequences. FIG. 5J further illustrates this point and shows a symbolic representation of some transducer graphical elements (shown as squares) and between graphical elements (shown connecting the larger squares), which may be displayed according to any of the graphical representations of FIGS. 5A-5I, 5K, and 6, according to various example embodiments. In other words, although FIG. 5J shows a two-dimensional representation of transducer graphical elements and between graphical elements that may be presented in accordance with the two-dimensional representation of FIG. 5D, such transducer graphical elements and between graphical elements may instead appear in a three-dimensional representation like that shown in any of FIGS. 5A-5C, 5E-5I, 5K, and 6 (further including diagonal between graphical elements not shown in FIG. 5J, but which may be included). The transducer graphical elements in FIG. 5J will be referenced by row and column, e.g., E:3, according to the same convention used with respect to FIGS. 5A-5I, 5K, and 6. As with earlier discussions regarding columns 512 and rows 510, which may correspond to those in FIG. 5J, adjacent ones of the rows in FIG. 5J may represent rows along a transducer-based system separated from each other at least by a physical portion (e.g., not including any transducer) of the transducer-based system, and adjacent ones of the columns in FIG. 5J may represent columns along the transducer-based system separated from each other at least by a non-physical portion of the transducer-based system.

With reference to FIG. 5J, assume that the above-mentioned transducer set "A", the above-mentioned transducer set "B", and the above-mentioned transducer set "C" include transducers associated with the transducer graphical elements shown in Table I, below, forming a row across row three:

TABLE I

| Transducer Set | Transducer Graphical Elements |
|---|---|
| A (e.g., "first particular other set") | A:3, B:3, C:3, D:3 |
| B (e.g., "second particular other set" activated at same or later time than transducer set "A") | G:3, H:3, I:3, J:3, A:3 |
| C (e.g., "first transducer set" activation delayed with respect to transducer sets "A" and "B") | D:3, E:3, F:3, G:3 |

Also, in these embodiments, assume that the transducer associated with transducer graphical element J:3 is adjacent the transducer associated with transducer graphical element A:3 (e.g., that column "J" is right next to column "A", because the transducers associated with the transducer graphical elements depicted in FIG. 5J are arranged circumferentially, such as shown by the transducer graphical elements in any of FIGS. 5A-5C, 5E-5I, 5K, and 6). In this regard, transducer set "A" and transducer set "B" both include the same transducer, i.e., the transducer associated with transducer graphical element A:3, which is not included in transducer set "C". However, it should be noted that transducer sets "A" and "B" may include at least a same transducer in other circumstances where the transducers are not arranged circumferentially such that last and first columns are adjacent. Accordingly, the following discussions may include but do not require that columns "J" and "A" be adjacent.

In embodiments including the configuration of Table I applied to FIG. 5J, it may be considered that the transducer associated with transducer graphical element D:3 is a first transducer of transducer set "C", and that the transducer associated with transducer graphical element G:3 is a second transducer of transducer set "C". In such a case, it can be seen that the first transducer and the second transducer are located on a same particular row (i.e., row "3"). In addition, it can be seen that transducer sets "A" and "B" include at least one transducer (e.g., associated with one or more of transducer graphical elements A:3, B:3, C:3, H:3, I:3, J:3) other than the first transducer (e.g., associated with transducer graphical element D:3) and the second transducer (e.g., associated with transducer graphical element G:3) located in the same row (i.e., row "3") as the first transducer and the second transducer. It can be considered that the first transducer is in a first particular column (i.e., column "D"), the second transducer is in a second particular column (i.e., column "G"), and there is at least one other column (e.g., column "E" and column "F") between the first particular column and the second particular column. Also, it can be seen that transducer sets "A" and "B" include at least one transducer (e.g., associated with one or more of transducer graphical elements A:3, B:3, C:3, H:3, I:3, J:3) other than the first transducer (e.g., associated with transducer graphical element D:3) and the second transducer (e.g., associated with transducer graphical element G:3) located on a column other than the first particular column (i.e., column "D") and the second particular column (i.e., column "G").

With reference to FIG. 5J, now assume that the above-mentioned transducer set "A", the above-mentioned transducer set "B", and the above-mentioned transducer set "C" include transducers associated with the transducer graphical elements shown in Table II, below:

TABLE II

| Transducer Set | Transducer Graphical Elements |
|---|---|
| A (e.g., "first particular other set") | B:3, C:3, D:3 |
| B (e.g., "second particular other set" activated at same or later time than transducer set "A") | F:4, G:4 |
| C (e.g., "first transducer set" activation delayed with respect to transducer sets "A" and "B") | D:3, E:3, E:4:F4 |

In embodiments including the configuration of Table II applied to FIG. 5J, it may be considered that the transducer associated with transducer graphical element D:3 is a first transducer of transducer set "C", and that the transducer associated with transducer graphical element F:4 is a second transducer of transducer set "C". In this regard, the first transducer is located on a first particular one of the columns (i.e., column "D") and the second transducer is located on a second particular one of the columns (i.e., column "F"), at least one other of the columns (i.e., column "E") arranged between the first particular one of the columns and the second particular one of the columns. It can be seen that transducer sets "A" and "B" include at least one transducer (e.g., associated with one or more of transducer graphical elements B:3, C:3, and G:4) other than the first transducer (e.g., associated with transducer graphical element D:3) and the second transducer (e.g., associated with transducer graphical element F:4) located on a column other than the first particular column (i.e., column "D") and the second particular column (i.e., column "F"). In addition, the first transducer (i.e., associated with transducer graphical element D:3) is located on a first particular one of the rows (i.e., row "3") and the second transducer (i.e., associated with transducer graphical element F:4) is located on a second particular one of the rows (i.e., row "4") other than the first particular one of the rows (i.e., row "3").

With reference to FIG. 5J, now assume that the above-mentioned transducer set "A", the above-mentioned transducer set "B", and the above-mentioned transducer set "C" include transducers associated with the transducer graphical elements shown in Table III, below:

TABLE III

| Transducer Set | Transducer Graphical Elements |
|---|---|
| A (e.g., "first particular other set") | D:3, D:4 |
| B (e.g., "second particular other set" activated at same or later time than transducer set "A") | F:3, G:3 |
| C (e.g., "first transducer set" activation delayed with respect to transducer sets "A" and "B") | D:3, E:3, F:3 |

In embodiments including the configuration of Table III applied to FIG. 5J, it may be considered that the transducer associated with transducer graphical element D:3 is a first transducer of transducer set "C", and that the transducer associated with transducer graphical element F:3 is a second transducer of transducer set "C". In this regard, the first transducer is located on a first particular one of the columns (i.e., column "D") and the second transducer is located on a second particular one of the columns (i.e., column "F"), at least one other of the columns (i.e., column "E") arranged between the first particular one of the columns and the second particular one of the columns. In addition, the first transducer and the second transducer are located on a same particular one of the rows (i.e., row "3"). Further, transducer set "A" includes a transducer other than the first transducer (and the second transducer) associated with transducer graphical element D:4 located on the first particular one of the columns (i.e., column "D"), and transducer set "B" includes a transducer other than the first transducer and the second transducer associated with transducer graphical element G:3 located on the same particular one of the rows (i.e., row "3"). Further still, the transducer associated with transducer graphical element D:4 of transducer set "A" is located on one of the rows (i.e., row "4") other than the same particular one of the rows (i.e., row "3").

With reference to FIG. 5J, now assume that the above-mentioned transducer set "A", the above-mentioned transducer set "B", and the above-mentioned transducer set "C" include transducers associated with the transducer graphical elements shown in Table IV, below:

TABLE IV

| Transducer Set | Transducer Graphical Elements |
|---|---|
| A (e.g., "first particular other set") | E:3 |
| B (e.g., "second particular other set" activated at same or later time than transducer set "A") | B:3, C:3 |
| C (e.g., "first transducer set" activation delayed with respect to transducer sets "A" and "B") | C:3, D:3, E:3 |

In embodiments including the configuration of Table IV applied to FIG. 5J, it may be considered that the transducer associated with transducer graphical element C:3 is a first transducer of transducer set "C", and that the transducer associated with transducer graphical element E:3 is a second transducer of transducer set "C". In this regard, it can be seen that transducer set "A" includes only a single transducer, the single transducer associated with transducer graphical element E:3.

Accordingly, in view of the descriptions here, it can be seen that the invention is not limited to any particular arrangement or composition of transducer sets or transducer set activation sequences. The particular configurations in FIG. 5J are provided merely to illustrate this point, and the invention is not limited to the particular configurations in FIG. 5J or any other particular configuration described herein.

We now turn to embodiments that vary visual characteristics of graphical elements during transducer activation processes. For example, the activation instructions as per block 811 in method 800 in FIG. 10, can include activation instructions configured to, in response to receiving at least part of a selection of various between graphical elements 504 associated with each of a plurality of transducer sets selected according to a first sequence, cause, via the input-output device system, energy from an energy source device system (e.g., energy source device system 340) to be delivered to each of the transducer sets according to a second sequence different than the first sequence. In some embodiments, during this energy delivery process, visual characteristics of the selected between graphical elements 504 can be varied to illustrate to a user a status of the energy delivery process. It should be noted, however, that the variances of visual characteristics described herein need not apply only to the method 800 or to the selection of between graphical elements 504, but can also apply to any activation process and to any graphical element according to the various embodiments described herein. The method of 800 and between graphical elements 504 are only used for illustration purposes.

In this regard, FIGS. 5G and 5H, show example sequential variances in visual characteristics of respective ones of the between graphical elements 504 associated with at least some of the transducers sets as they are activated according to the second sequence. Changes in the visual characteristics are highlighted in accordance with a KEY provided in each of FIGS. 5G, 5H and 5I. It is understood that the KEY is provided for illustrative purposes and does not form part of the graphical representation in this example embodiment. As discussed above, variances in visual characteristics may include changing a color, opacity, hue, intensity, shading, pattern, shape or the addition or removal of any displayed information.

FIG. 5G is associated with a condition in which energy is being delivered (e.g., according to the second sequence) to the respective transducer set associated with the first between graphical element 504a (e.g., previously identified as "R:6-Q:6" and to the respective transducer set associated with another between graphical element 504 (e.g., previously identified as "P:10-Q:10") while energy is not delivered to the respective transducer sets associated with the remaining ones of the selected between graphical elements 504. It is noted that the energy delivered to the transducer set associated with the between graphical element 504 previously identified as "P:10-Q:10" is not delivered according to the sequence it was selected with respect to the other of the transducer sets. It is noted that the respective electrograms 535 associated with the respective transducers of at least some of the transducer sets to which energy is delivered (e.g., the transducer set associated with the between graphical element 504 previously identified as "P:10-Q:10") are repositioned in the graphical representation for enhanced viewing during the energy delivery (e.g., as best compared between FIGS. 5F and 5G).

FIG. 5H is associated with a condition in which the energy delivery has been completed to respective transducer sets associated with each of the between graphical elements 504 previously identified as "R:6-Q:6" and "P:10-Q:10". FIG. 5H is associated with a condition in which energy is being delivered to the respective transducer sets associated with the between graphical elements 504 previously identified as "R:9-S:9" and "S:7-R:7" while energy is not delivered to the other respective transducer sets that have not yet received energy or the other respective transducer sets in which the energy delivery has been completed. Again, it is noted that the energy delivered to the transducer sets associated with the between graphical elements 504 previously identified as "R:9-S:9" and "S:7-R:7" is not delivered according to the first sequence in which these transducer sets were selected with respect to the others of the group of transducer sets. In this example embodiment, the energy delivery process according to the remainder of the second sequence continues, until energy has been delivered to all of the remaining selected transducer sets as exemplified in FIG. 5I. It is noted that for brevity of illustration, energy delivery to every one of the selected remaining transducer sets in accordance with the remainder of the second sequence has not been shown.

In this example embodiment, the activation instructions of blocks 810, 811 cause the transmission of energy-delivery instructions (not shown) to cause energy from the energy source device system to be delivered to each of the respective first transducer and second transducer of the corresponding transducer set associated with each of the selected between graphical elements 504. FIG. 8 includes a block 818 that includes determination instructions (e.g., instructions provided by a program) configured to determine an energy-delivery status associated with at least one of the respective first transducer and the respective second transducer associated with each of the selected between graphical elements 504, the energy delivery status indicating a status of the energy delivery by the energy source device system to the at least one of the respective first transducer and the respective second transducer. In some embodiments, the energy delivery status includes a status of a portion of the energy delivered by the energy source device system to the at least one of the respective first transducer and the respective second transducer, the portion of the energy transmitted by the at least one of the respective first transducer and the respective second transducer. FIG. 8 includes a block 820 that includes energy delivery indication instructions configured to cause the input-output device system to change a displayed visual characteristic of a selected between graphical element 504 based at least on the determined energy-status of the at least one of the respective first transducer and the respective second transducer. For example, referring to FIG. 5G, the energy delivery status associated with the at least one of the respective first and the respective second transducers associated with the selected between graphical element 504a previously identified as "R:6-Q:6" includes a during-energy delivery status associated with a state during the energy delivery by the energy source device system to the at least one of the first transducer and the second transducer associated with the selected between graphical element 504a previously identified as "R:6-Q:6". The energy delivery status associated with the at least one of the respective first and second transducers associated with the selected between graphical element 504 previously identified as "S:7-R:7" includes a pre-energy-delivery status associated with a state before a start of energy delivery by the energy source device system to the at least one of the first transducer and the second transducer associated with the selected between graphical element 504 previously identified as "S:7-R:7". As shown in FIG. 5G, a first displayed visual characteristic of the between graphical elements 504 is associated with the pre-energy-delivery status (e.g., the selected between graphical element 504 previously identified as "S:7-R:7") and a second displayed visual characteristic of the between graphical elements 504 is associated with the during-energy-delivery status (e.g., the selected between graphical element 504 previously identified as "R:6-Q:6"), the second displayed visual characteristic being different than the first displayed visual characteristic. Differences in the displayed visual characteristics may include different colors, opacities, hues, intensity, shading, patterns, shapes or any suitable addition or removal of any displayed information sufficient for characterizing the difference. In some embodiments, the first displayed visual characteristic of a between graphical element 504 associated with the pre-energy delivery status is different than a visual characteristic of the between graphical element 504 resulting upon a selection of the between graphical element 504 (e.g., as per block 812). In this embodiment, the first displayed visual characteristic of a between graphical element 504 associated with the pre-energy delivery status is the same as a visual characteristic of the between graphical element 504 resulting upon a selection of the between graphical element 504. It is noted that in this example embodiment that the between graphical element 504a previously identified as "R:6-Q:6" included the first displayed visual characteristic prior to energy delivery to the corresponding ones of the transducers.

In FIG. 5H, the energy delivery status associated with the at least one of the first transducer and the second transducer associated with the between graphical element 504a previously identified as "R:6-Q:6" includes a post-energy-delivery status associated with a state after a completion of the energy delivery from the energy source device system to the at least one of the first transducer and the second transducer associated with the between graphical element 504a previously identified as "R:6-Q:6". In FIG. 5H, a pre-energy-delivery status is associated with at least some of the between graphical elements (e.g., the between graphical element 504 previously identified as "P:7-O:7") and a during-energy-delivery status is associated with at least some of the between graphical elements (e.g., the between graphical element 504 previously identified as "S:7-R:7"). In this example embodiment, a third displayed visual characteristic of the between graphical elements 504 associated with the post-energy delivery-state (e.g., the between graphical element 504a previously identified as "R:6-Q:6") is different than at least one (e.g., both in this example embodiment) of the first displayed visual characteristic of the between graphical elements 504 associated with the pre-energy delivery-state (e.g., the between graphical element 504 previously identified as "P:7-O:7") and the second displayed visual characteristic of the between graphical elements 504 associated with the during-energy delivery-state (e.g., the between graphical element 504 previously identified as "S:7-R:7"). In FIG. 5I all of the selected between graphical elements 504 are shown with the third displayed visual characteristic, indicating that completion of the energy delivery to their respective transducer sets has occurred. In this example embodiment, the displayed visual characteristics of at least some of the respective transducer graphical elements 502 associated with the respective first and the second transducers associated with each selected between graphical elements undergo changes in accordance with changes in the energy-delivery state. The displayed visual characteristics associated with the various energy-delivery states are depicted in accordance with the KEY provided in each of FIGS. 5G, 5H and 5I. And, in some embodiments, energy-delivery state may include a type of energy delivery, such as the delivery of energy for monopolar ablation or the delivery of energy for bipolar ablation. In this regard, the visual characteristics associated with the delivery of energy for monopolar ablation may be different than the visual characteristics associated with the delivery of energy for bipolar ablation.

While some of the embodiments disclosed above are described with examples of cardiac mapping, the same or similar embodiments may be used for mapping other bodily organs, for example gastric mapping, bladder mapping, arterial mapping and mapping of any lumen or cavity into which the devices of the present invention may be introduced.

While some of the embodiments disclosed above are described with examples of cardiac ablation, the same or similar embodiments may be used for ablating other bodily organs or any lumen or cavity into which the devices of the present invention may be introduced.

Subsets or combinations of various embodiments described above can provide further embodiments.

These and other changes can be made to the invention in light of the above-detailed description. In general, in the following claims, the terms used should not be construed to limit the invention to the specific embodiments disclosed in the specification and the claims, but should be construed to include other transducer-based device systems including all medical treatment device systems and all medical diagnostic device systems in accordance with the claims. Accordingly, the invention is not limited by the disclosure, but instead its scope is to be determined entirely by the following claims.

What is claimed is:

1. A transducer-activation system comprising:
   a data processing device system;
   an input-output device system communicatively connected to the data processing device system and a transducer-based device; and
   a memory device system communicatively connected to the data processing device system and storing a program executable by the data processing device system, the program comprising:
   display instructions configured to cause the input-output device system to concurrently display:
      at least a map depicting a surface of a tissue wall of the bodily cavity, the surface interrupted by one or more ports, and
      a plurality of transducer graphical elements, each transducer graphical element of the plurality of transducer graphical elements corresponding to at least part of a respective one of a plurality of transducers of the transducer-based device, the plurality of transducers arranged in a distribution, the distribution positionable in a bodily cavity, and a first spatial relationship between the displayed plurality of transducer graphical elements consistent with a second spatial relationship between the plurality of transducers in the distribution;
   selection instructions configured to cause selection, via the input-output device system, of selected transducer graphical elements representing less than all of the plurality of transducer graphical elements, the selected transducer graphical elements corresponding to selected transducers representing less than all of the plurality of transducers, the selected transducers defining a plurality of transducer sets including at least a first transducer set; and
   activation instructions configured to cause activation, via the input-output device system, of the plurality of transducer sets according to a sequence, the activation according to the sequence including an initiation of an activation of each transducer in the first transducer set after activation of each transducer in each of at least a second transducer set of the plurality of transducer sets has completed, the first transducer set comprising a first transducer included in the second transducer set,
   wherein the display instructions are configured to cause the input-output device system to display the selected transducer graphical elements surrounding at least one of the one or more ports depicted in the map.

2. The transducer-activation system of claim 1 wherein the plurality of transducer sets comprises a third transducer set, the third transducer set excluding the first transducer, and wherein the activation according to the sequence includes the initiation of the activation of each transducer in the first transducer set after activation of each transducer in the third transducer set has completed.

3. The transducer-activation system of claim 2 wherein the activation according to the sequence includes the initiation of the activation of each transducer in the third transducer set after activation of each transducer in the second transducer set has completed.

4. The transducer-activation system of claim 1 wherein the plurality of transducer sets comprises at least three transducer sets, and wherein the activation according to the sequence includes the initiation of the activation of each transducer in the first transducer set after activation of each transducer in each of the other transducer sets of the plurality of transducer sets has completed.

5. The transducer-activation system of claim 1 wherein the activation according to the sequence comprises a completion of each of at least two activations of each of at least two of the selected transducers during the activation according to the sequence.

6. The transducer-activation system of claim 1 wherein the activation instructions are configured to cause, via the input-output device system, completion of the activation according to the sequence when each of the selected transducers has been activated at least once during the activation according to the sequence and each of at least some of the selected transducers has been activated at least twice during the activation according to the sequence.

7. The transducer-activation system of claim 1 wherein, during the activation according to the sequence, the display instructions are configured to cause the input-output device system to display each respective selected transducer graphical element with a respective first visual characteristic set during activation of the respective selected transducer and with a respective second visual characteristic set after completion of the activation of the respective selected transducer, the respective second visual characteristic set different than the respective first visual characteristic set.

8. The transducer-activation system of claim 1 wherein the display instructions are configured to cause the input-output device system to display the selected transducer graphical elements surrounding at least some of the plurality of transducer graphical elements other than the selected transducer graphical elements.

9. The transducer-activation system of claim 1 wherein the program further comprises information reception instructions configured to cause reception via the input-output device system of information from each of the plurality of transducers, and wherein the display instructions are configured to cause the input-output device system to display the map based at least on the information received from the each of the plurality of transducers.

10. The transducer-activation system of claim 1 wherein the display instructions are configured to cause the input-output device system to display the selected transducer graphical elements in a manner different than the display of others of the transducer graphical elements.

11. The transducer-activation system of claim 1 wherein the display instructions are configured to cause the input-output device system to display a plurality of between graphical elements, each of the plurality of between graphical elements associated with a region of space between the transducers of a respective one of a plurality of groups of adjacent ones of the transducers of the plurality of transducers, each region of space not including any transducer.

12. The transducer-activation system of claim 11
wherein the display instructions are configured to cause the input-output device system to display the selected transducer graphical elements in a manner different than the display of others of the transducer graphical elements, and wherein the display instructions are configured to cause the input-output device system to display the respective between graphical elements between respective groups of adjacent ones of the selected transducer graphical elements in a manner different than the display of others of the between graphical elements.

13. The transducer-activation system of claim 11 wherein the transducer-activation system comprises the transducer-based device, which comprises the plurality of transducers, and wherein at least one of the between graphical elements is associated with a region of space that is not associated with any physical part of the transducer-based device.

14. The transducer-activation system of claim 13
wherein the distribution is an array-based distribution comprising a plurality of intersecting rows and columns, adjacent ones of the rows separated from each other at least by a physical portion of the transducer-based system, and adjacent ones of the columns separated from each other at least by a non-physical portion of the transducer-based system, and wherein the region of space that is not associated with any physical part of the transducer-based device is between the transducers of a particular one of the plurality of groups of adjacent ones of the transducers that comprises one transducer located on a first particular one of the columns and another transducer located on a second particular one of the columns.

15. The transducer-activation system of claim 1 wherein the activation instructions are configured to cause, via the input-output device system, each of the selected transducers to transmit energy sufficient for tissue ablation during the activation according to the sequence.

16. The transducer-activation system of claim 1 wherein the activation instructions are configured to cause, via the input-output device system, the selected transducers to transmit energy during the activation according to the sequence, the energy sufficient to form a series of ablated regions in the bodily cavity during a state in which the distribution is positioned in the bodily cavity, the series of ablated regions arranged along an ablation path that surrounds the at least one of the one or more ports.

17. The transducer-activation system of claim 16, wherein the display instructions are configured to cause the input-output device system to display a representation of the ablation path surrounding the at least one of the one or more ports depicted in the map.

18. The transducer-activation system of claim 16, wherein the display instructions are configured to cause the input-output device system to display a representation of the ablation path surrounding the at least one of the one or more ports depicted in the map at least prior to the activation according to the sequence.

19. The transducer-activation system of claim 1 wherein the activation instructions are configured to cause, via the input-output device system, the selected transducers to transmit energy during the activation according to the sequence, the energy sufficient to form an electrophysiological conduction block arranged to continuously surround the at least one of the one or more ports during a state in which the distribution is positioned in the bodily cavity.

20. The transducer-activation system of claim 1 wherein the activation instructions are configured to cause, via the input-output device system, the first transducer to transmit energy sufficient for tissue ablation during each activation of the first transducer during the activation according to the sequence.

21. The transducer-activation system of claim 1 wherein the first transducer set comprises the first transducer and a second transducer, and the second transducer set comprises the first transducer and a third transducer other than the second transducer, wherein the activation instructions are configured to cause, via the input-output device system, concurrent activation of both the first transducer and the second transducer during the activation of the first transducer set during the activation according to the sequence, and wherein the activation instructions are configured to cause, via the input-output device system, concurrent activation of both the first transducer and the third transducer during the activation of the second transducer set during the activation according to the sequence.

22. The transducer-activation system of claim 1 wherein the selection instructions are configured to cause a first concurrent selection, via the input-output device system, of a first transducer graphical element corresponding to the first transducer and a second transducer graphical element corresponding to a second transducer, and the selection instructions are configured to cause a second concurrent selection, via the input-output device system, of the first transducer graphical element and a third transducer graphical element corresponding to a third transducer other than the second transducer, the second concurrent selection occurring after the first concurrent selection.

* * * * *